(12) United States Patent
Fraser et al.

(10) Patent No.: US 9,504,718 B2
(45) Date of Patent: *Nov. 29, 2016

(54) METHODS OF USING ADIPOSE DERIVED REGENERATIVE CELLS IN THE TREATMENT OF RENAL DISEASES AND DISORDERS

(71) Applicant: CYTORI THERAPEUTICS, INC., San Diego, CA (US)

(72) Inventors: John K. Fraser, San Diego, CA (US); Marc H. Hedrick, Encinitas, CA (US); Eric Daniels, Encinitas, CA (US)

(73) Assignee: Cytori Therapeutics, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/849,900

(22) Filed: Mar. 25, 2013

(65) Prior Publication Data
US 2013/0344035 A1    Dec. 26, 2013

Related U.S. Application Data

(63) Continuation of application No. 10/884,639, filed on Jul. 1, 2004, now Pat. No. 8,404,229, which is a continuation-in-part of application No. 10/316,127, filed on Dec. 9, 2002, now abandoned.

(60) Provisional application No. 60/338,856, filed on Dec. 7, 2001.

(51) Int. Cl.
| | | |
|---|---|---|
| C12N 5/00 | (2006.01) | |
| A61K 35/35 | (2015.01) | |
| A61L 27/38 | (2006.01) | |
| A61L 27/54 | (2006.01) | |
| A61M 1/36 | (2006.01) | |
| C12N 5/0775 | (2010.01) | |
| A61K 35/22 | (2015.01) | |
| A61K 35/28 | (2015.01) | |
| A61K 35/44 | (2015.01) | |

(52) U.S. Cl.
CPC ............... *A61K 35/35* (2013.01); *A61K 35/22* (2013.01); *A61K 35/28* (2013.01); *A61K 35/44* (2013.01); *A61L 27/3834* (2013.01); *A61L 27/3886* (2013.01); *A61L 27/54* (2013.01); *A61M 1/3693* (2013.01); *C12N 5/0667* (2013.01); *A61L 2300/414* (2013.01); *A61L 2300/416* (2013.01); *A61L 2430/26* (2013.01); *A61M 2202/0437* (2013.01); *A61M 2202/08* (2013.01)

(58) Field of Classification Search
None
See application file for complete search history.

(56) References Cited

U.S. PATENT DOCUMENTS

| | | | |
|---|---|---|---|
| 8,404,229 B2 * | 3/2013 | Fraser et al. ............... | 424/93.7 |
| 2007/0116674 A1 | 5/2007 | Casteilla et al. | |
| 2007/0274960 A1 | 11/2007 | Harman et al. | |
| 2008/0206208 A1 | 8/2008 | Casteilla et al. | |
| 2013/0108592 A1 | 5/2013 | Pinkernell et al. | |
| 2013/0121974 A1 | 5/2013 | Fraser et al. | |

FOREIGN PATENT DOCUMENTS

| | | |
|---|---|---|
| EP | 1 678 295 | 3/2013 |
| JP | 2004-99471 | 4/2004 |
| KR | 10-2004-0063167 | 7/2004 |
| WO | WO 03/073998 | 9/2003 |
| WO | WO 2005/025584 | 3/2005 |
| WO | WO 2006/014156 | 2/2006 |
| WO | WO 2007/135284 | 11/2007 |
| WO | WO 2009/076548 | 6/2009 |

OTHER PUBLICATIONS

BD Biosciences, Feb. 15, 2002, Product Specification Sheet: BD Matrigel™ Basement Membrane Matrix, 3 pp.
Cousin et al., Jul. 2009, Adult stromal cells dervied from human adipose tissue provoke pancreatic cancer cell death both in vitro and in vivo, PLoS One, 4(7), e6278.
Gimble et al., 2007, Adipose-derived stem cells for regenerative medicine, Circulation Research, 100:1249-1260.
Gronthos et al., 2001, Surface protein characterization of human adipose tissue-derived stromal cells, Journal of Cellular Physiology, 189:54-63.
Haynes, 1988, Principles of flow cytometery, Cytometry Supplement, 3:7-17.
Herzenberg et al., 2002, The history and future of the fluorescence activated cell sorter and flow cytometry: a view from Stanford, Clinical Chemistry, 48(10)1819-1827.
Kawamoto et al., 2001, Therapeutic potential of ex vivo expanded endothelial progenitor cells for myocardial ischemia, Circulation, 103:634-637.
Kim et al., 2007, Systemic transplantation of human adipose stem cells attenuated cerebral inflammation and degeneration in a hemorrhagic stroke model, Brain Research, 1183:42-50.
Rehman et al., 2007, Human adipose stromal cells express the angiogenic factor VEGF and its receptor VEGFR-2, Arterioscler Thromb Vasc Biol, 22:878, Poster Presentation P111, p. a-19.
Rivard et al., 1998, Angiogenesis and vasculogenesis in treatment of cardiovascular disease, Molecular Medicine, 4:429-440.
Tondreau et al., 2004, Isolation of BM mesenchymal stem cells by plastic adhesion or negative selection: phenotype, proliferation kinetics and differentiation potential, Cytotherapy, 6(4):372-379.

* cited by examiner

*Primary Examiner* — Blaine Lankford
(74) *Attorney, Agent, or Firm* — Knobbe Martens Olson & Bear LLP

(57) ABSTRACT

Cells present in processed lipoaspirate tissue are used to treat patients, including patients with renal conditions, diseases or disorders. Methods of treating patients include processing adipose tissue to deliver a concentrated amount of stem cells obtained from the adipose tissue to a patient. The methods may be practiced in a closed system so that the stem cells are not exposed to an external environment prior to being administered to a patient. Accordingly, in a preferred method, cells present in processed lipoaspirate are placed directly into a recipient along with such additives necessary to promote, engender or support a therapeutic renal benefit.

19 Claims, 22 Drawing Sheets

TANGENTIAL CROSS-FLOW FILTRATION
(HIGH PERMEATE RATE)

DEAD-END FILTRATION
(LOW PERMEATE RATE)

UEA-1 Staining of ADC-derived EPC Colony

METHODS OF USING ADIPOSE DERIVED REGENERATIVE CELLS IN THE TREATMENT OF RENAL DISEASES AND DISORDERS

RELATED APPLICATIONS

This application is continuation of U.S. application Ser. No. 10/884,639 to Fraser et al, entitled "METHODS OF USING REGENERATIVE CELLS IN THE TREATMENT OF RENAL DISEASES AND DISORDERS," filed Jul. 1, 2004, which is a continuation-in-part application of U.S. application Ser. No. 10/316,127, to Fraser, et al., entitled SYSTEMS AND METHODS FOR TREATING PATIENTS WITH PROCESSED LIPOASPIRATE CELLS, filed Dec. 9, 2002, which claims the benefit of U.S. Provisional Application No. 60/338,856, filed Dec. 7, 2001. The contents of each of the aforementioned applications are expressly incorporated herein by this reference.

BACKGROUND OF THE INVENTION

1. Field of the Invention

This invention generally relates to regenerative cells derived from a wide variety of tissues, and more particularly, to adipose-derived regenerative cells (e.g., stem and/or progenitor cells), methods of using adipose-derived regenerative cells, compositions containing adipose-derived regenerative cells, and systems for preparing and using adipose-derived regenerative cells which are used to treat renal diseases and disorders, e.g., acute tubular necrosis related diseases and disorders.

2. Description of the Related Art

Acute renal failure (ARF) is defined as an abrupt or rapid decline in renal (kidney) function. ARF occurs when high levels of uremic toxins, i.e., waste products of the body's metabolism, accumulate in the blood, and the kidneys are unable to excrete the requisite amount of the toxins through the urine. Since only one kidney is required to adequately filter blood, the onset of ARF generally indicates that both kidneys are failing to perform as needed.

ARF can occur in three clinical settings which are named for their location within the renal system, i.e., prerenal ARF, intrinsic ARF and postrenal ARF. Prerenal ARF is an adaptive response to severe volume depletion and hypotension and is characterized by structurally and functionally intact nephrons. Postrenal ARF is the result of an obstruction to the passage of urine. Intrinsic ARF is generally the most harmful form of ARF because it is a response to cytotoxic insults to the kidney and results in structural and functional damage that may be irreversible.

In the hospital setting, the most common cause of intrinsic ARF is acute tubular necrosis (ATN). ATN is the death of tubular cells. Tubules are extremely active structures in the kidney. They transport urine to the ureters and, in the process, alter the urine and its chemicals. Studies have shown that for every 200 liters of fluid that is filtered across the glomeruli, 99% is reabsorbed by the tubules. ATN, or death of tubular cells, occurs when the cells do not get enough oxygen (ischemic ATN) or when the cells have been exposed to a toxic drug or molecule (nephrotoxic ATN). Ischemic ATN is the most common cause of ARF in the hospital setting because hospital patients often have acute medical problems that limit the oxygen supplied to the tubules or that cause tubular hypoperfusion (decreased blood flow) (Thadhani R, Pascual M, Bonventre J V. Acute Renal Failure. N. Engl J. Med. 334:1448-1460).

ARF is the most common cause of death in hospitalized patients in the United States. Part of the reason for this mortality rate lies in the limited ability of the kidney tubular cells to repair themselves following ischemic damage. Thus, ARF patients often suffer from irreversibly damaged kidneys. Although, renal replacement therapies (RRTs), i.e., dialysis, can effectively treat life-threatening complications of ARF such as seizures, bleeding and coma, other risk factors prevalent in hospitalized patients (such as advanced age and underlying diseases) continue to cause a high mortality rate despite the availability of RRTs.

An alternative to transplant therapy is the use of regenerative medicine to repair and regenerate damaged renal cells, e.g., tubular cells. Regenerative medicine harnesses, in a clinically targeted manner, the ability of stem cells (i.e., the unspecialized master cells of the body) to renew themselves indefinitely and develop into mature specialized cells. For example, adult stem cells (ASCs) from bone marrow have been used in preclinical studies for the treatment of ATN (Kale S. et al. Bone Marrow Stem Cells Contribute to Repair of the Ischemically Injured Renal Tubule. JCI. 112:42-49, 2003; Poulsom R, et al. Bone marrow contributes to renal parenchymal turnover and regeneration. J Pathol; 195:229-235. 2001).

However, although ASC populations have been shown to be present in one or more of bone marrow, skin, muscle, liver and brain (Jiang et al., 2002b; Alison, 1998; Crosby and Strain, 2001), their frequency in these tissues is low. For example, mesenchymal stem cell frequency in bone marrow is estimated at between 1 in 100,000 and 1 in 1,000,000 nucleated cells (D'Ippolito et al., 1999; Banfi et al., 2001; Falla et al., 1993). Similarly, extraction of ASCs from skin involves a complicated series of cell culture steps over several weeks (Toma et al., 2001) and clinical application of skeletal muscle-derived ASCs requires a two to three week culture phase (Hagege et al., 2003). Thus, any proposed clinical application of ASCs from such tissues requires increasing cell number, purity, and maturity by processes of cell purification and cell culture.

Although cell culture steps may provide increased cell number, purity, and maturity, they do so at a cost. This cost can include one or more of the following technical difficulties: loss of cell function due to cell aging, loss of potentially useful non-stem cell populations, delays in potential application of cells to patients, increased monetary cost, and increased risk of contamination of cells with environmental microorganisms during culture. Recent studies examining the therapeutic effects of bone-marrow derived ASCs have used essentially whole marrow to circumvent the problems associated with cell culturing (Horwitz et al., 2001; Orlic et al., 2001; Stamm et al., 2003; Strauer et al., 2002). The clinical benefits, however, have been suboptimal, an outcome almost certainly related to the limited ASC dose and purity inherently available in bone marrow.

Recently, adipose tissue has been shown to be a source of ASCs (Zuk et al., 2001; Zuk et al., 2002). Adipose tissue (unlike marrow, skin, muscle, liver and brain) is comparably easy to harvest in relatively large amounts with low morbidity (Commons et al., 2001; Katz et al., 2001b). Suitable methods for harvesting adipose derived ASCs, however, are lacking in the art. The existing methods suffer from a number of shortcomings. For example, the existing methods lack partial or full automation, a partial or completely closed system, disposability of components, etc.

Given the tremendous therapeutic potential of adipose derived ASCs for regenerating and repairing renal cells, there exists a need in the art for a method for harvesting cells from adipose tissue that produces a population of adult stem cells with increased yield, consistency and/or purity and does so rapidly and reliably with a diminished or non-existent need for post-extraction manipulation.

SUMMARY OF THE INVENTION

The present invention relates to regenerative cells, e.g., adult stem and progenitor cells, that can be used to treat renal diseases or disorders. The present invention also relates to systems and methods for separating and concentrating regenerative cells from tissue, e.g., adipose tissue. The present invention further relates to compositions of regenerative cells to treat renal conditions, diseases or disorders. Accordingly, in a general embodiment, the present invention is directed to compositions, methods, and systems for using regenerative cells derived from tissue that are placed directly into a recipient along with such additives necessary to promote, engender, or support a therapeutic renal benefit.

In specific embodiments, the present invention is directed to methods for treating renal diseases and disorders, including both ischemic and nephrotoxic acute tubular necrosis (ATN), by administering a concentration of regenerative cells. The regenerative cells may be comprised of, e.g., stem cells, progenitor cells or combination thereof. In certain embodiments, administration of multiple doses of regenerative cells may be needed to derive a therapeutic benefit. In addition, additives such as one or more growth factors may be administered with the regenerative cells. In a preferred embodiment, the regenerative cells are administered with angiogenic growth factors alone or in combination with other additives. The regenerative cells may also be administered with one or more immunosuppressive drugs.

The routes of administration for the regenerative cells are known in the art and include intravenous, intra-arterial or intra-parenchymal administration routes. The cells may be administered to, for example the patient's renal vasculature. The cells may also be administered via a scaffold, e.g., a resorbable scaffold known in the art.

Prior to administration to a patient, the regenerative cells may be grown in cell culture to, for example, promote differentiation towards a renal and/or endothelial phenotype. The cell culture may be performed on a scaffold material, e.g., a resorbable scaffold, to generate a two or three dimensional construct that can be placed on or within the patient. Prior to administration to a patient, the cells could also be modified by gene transfer such that expression of one or more genes, e.g., an angiogenic gene or an apoptotic gene, in the modified regenerative cells is altered.

The present invention also relates to highly versatile systems and methods capable of separating and concentrating regenerative cells, e.g., stem and progenitor cells, from a given tissue that are suitable for re-infusion into a subject. In a preferred embodiment, the system is automated. The system of the present invention generally includes one or more of a collection chamber, a processing chamber, a waste chamber, an output chamber and a sample chamber. The various chambers are coupled together via one or more conduits such that fluids containing biological material may pass from one chamber to another in a closed, sterile fluid/tissue pathway. In certain embodiments, the waste chamber, the output chamber and the sample chamber are optional. In one embodiment, the entire procedure from tissue extraction through processing and placement of the device into the recipient would all be performed in the same facility, indeed, even within the same room of the patient undergoing the procedure.

Accordingly, in one embodiment, a method of treating a patient with a renal disease or disorder includes steps of: a) providing a tissue removal system; b) removing adipose tissue from a patient using the tissue removal system, the adipose tissue having a concentration of stem cells; c) processing at least a part of the adipose tissue to obtain a concentration of regenerative cells other than the concentration of regenerative cells of the adipose tissue before processing; and d) administering the regenerative cells to a patient without removing the regenerative cells from the tissue removal system before being administered to the patient, to thereby treat the renal disease or disorder.

Any feature or combination of features described herein are included within the scope of the present invention provided that the features included in any such combination are not mutually inconsistent as will be apparent from the context, this specification, and the knowledge of one of ordinary skill in the art. Additional advantages and aspects of the present invention are apparent in the following detailed description.

DETAILED DESCRIPTION OF THE INVENTION

Figure 1:
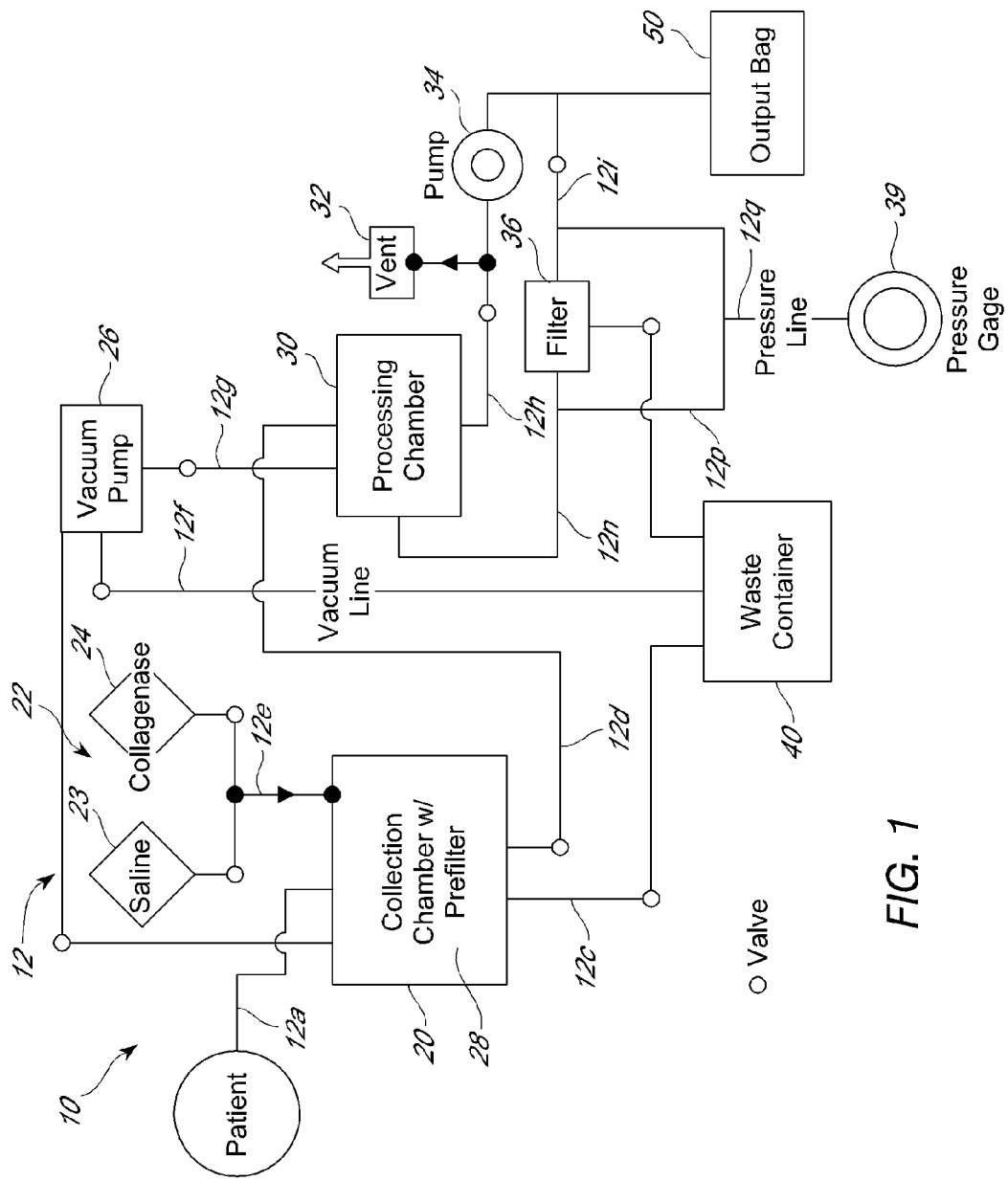
FIG. 1. is an illustration of a system for separating regenerative cells from tissue which includes one filter assembly.

The present invention provides methods for treating renal diseases and disorders, e.g., ATN, using adipose derived regenerative cells ("ADCs"). The present invention is based, in part, on the discovery that the regenerative cells of the invention (1) express angiogenic growth factors and cytokines, including PIGF, VEGF, bFGF, IGF-II, Eotaxin, G-CSF, GM-CSF, IL-12 p40/p70, IL-12 p70, IL-13, IL-6, IL-9, Leptin, MCP-1, M-CSF, MIG, PF-4, TIMP-1, TIMP-2, TNF-α, and Thrombopoetin, (2) comprise endothelial progenitor cells (EPC) which have a well-established function in blood vessel formation, (3) develop into blood vessels in vitro, and (4) support ischemic tissue survival in vivo. Studies have shown that capillary loss in the kidney correlates with alterations in VEGF expression. (see e.g., Kang, D. H. et al. Impaired angiogenesis in the aging kidney: vascular endothelial growth factor and thrombospondin-1 in renal disease. Am J Kidney Dis. 200137 (3): 601-11.) These and other findings indicate that impaired angiogenesis associated with progressive loss in renal microvasculature promotes renal failure. Accordingly, the regenerative cells of the present invention are useful for the treatment of renal diseases and disorders, e.g. ATN related diseases and disorders, by for example, promoting angiogenesis in the renal vasculature, e.g., the tubules.

The present invention also relates to rapid and reliable systems and methods for separating and concentrating regenerative cells, e.g., stem cells and/or progenitor cells, from a wide variety of tissues, including but not limited to, adipose, bone marrow, blood, skin, muscle, liver, connective tissue, fascia, brain and other nervous system tissues, blood vessels, and other soft or liquid tissues or tissue components or tissue mixtures (e.g., a mixture of tissues including skin, blood vessels, adipose, and connective tissue). In a preferred embodiment, the system separates and concentrates regenerative cells from adipose tissue. In another preferred embodiment, the system is automated such that the entire method may be performed with minimal user intervention or expertise. In a particularly preferred embodiment, the regenerative cells obtained using the systems and methods of the present invention are suitable for direct placement into a recipient suffering from a renal disease or disorder from whom the tissue was extracted.

Preferably, the entire procedure from tissue extraction through separating, concentrating and placement of the regenerative cells into the recipient would all be performed in the same facility, indeed, even within the same room of the patient undergoing the procedure. The regenerative cells may be used in a relatively short time period after extraction and concentration. For example, the regenerative cells may be ready for use in about one hour from the harvesting of tissue from a patient, and in certain situations, may be ready for use in about 10 to 40 minutes from the harvesting of the tissue. In a preferred embodiment, the regenerative cells may be ready to use in about 20 minutes from the harvesting of tissue. The entire length of the procedure from extraction through separating and concentrating may vary depending on a number of factors, including patient profile, type of tissue being harvested and the amount of regenerative cells required for a given therapeutic application. The cells may also be placed into the recipient in combination with other cells, tissue, tissue fragments, scaffolds or other stimulators of cell growth and/or differentiation in the context of a single operative procedure with the intention of deriving a therapeutic, structural, or cosmetic benefit to the recipient. It is understood that any further manipulation of the regenerative cells beyond the separating and concentrating phase of the system will require additional time commensurate with the manner of such manipulation.

In order that the present invention may be more readily understood, certain terms are first defined. Additional definitions are set forth throughout the detailed description.

As used herein, "regenerative cells" refers to any heterogeneous or homologous cells obtained using the systems and methods of the present invention which cause or contribute to complete or partial regeneration, restoration, or substitution of structure or function of an organ, tissue, or physiologic unit or system to thereby provide a therapeutic, structural or cosmetic benefit. Examples of regenerative cells include: ASCs, endothelial cells, endothelial precursor cells, endothelial progenitor cells, macrophages, fibroblasts, pericytes, smooth muscle cells, preadipocytes, differentiated or de-differentiated adipocytes, keratinocytes, unipotent and multipotent progenitor and precursor cells (and their progeny), and lymphocytes.

One mechanism by which the regenerative cells may provide a therapeutic, structural or cosmetic benefit is by incorporating themselves or their progeny into newly generated, existing or repaired tissues or tissue components. For example, ASCs and/or their progeny may incorporate into newly generated bone, muscle, or other structural or functional tissue and thereby cause or contribute to a therapeutic, structural or cosmetic improvement. Similarly, endothelial cells or endothelial precursor or progenitor cells and their progeny may incorporate into existing, newly generated, repaired, or expanded blood vessels to thereby cause or contribute to a therapeutic, structural or cosmetic benefit.

Another mechanism by which the regenerative cells may provide a therapeutic, structural or cosmetic benefit is by expressing and/or secreting molecules, e.g., growth factors, that promote creation, retention, restoration, and/or regeneration of structure or function of a given tissue or tissue component. For example, regenerative cells may express and/or secrete molecules which result in enhanced growth of tissues or cells that then participate directly or indirectly in improved structure or function. Regenerative cells may express and/or secrete growth factors, including, for example, Vascular Endothelial Growth Factor (VEGF), Placental Growth factor (PIGF), bFGF, IGF-II, Eotaxin, G-CSF, GM-CSF, IL-12 p40/p70, IL-12 p70, IL-13, IL-6, IL-9, Leptin, MCP-1, M-CSF, MIG, PF-4, TIMP-1, TIMP-2, TNF-α, Thrombopoetin, and their isoforms, which may perform one or more of the following functions: stimulate development of new blood vessels, i.e., promote angiogenesis; improve oxygen supply of pre-existent small blood vessels (collaterals) by expanding their blood carrying capacity; induce mobilization of regenerative cells from sites distant from the site of injury to thereby enhance the homing and migration of such cells to the site of injury; stimulate the growth and/or promote the survival of cells within a site of injury thereby promoting retention of function or structure; deliver molecules with anti-apoptotic properties thereby reducing the rate or likelihood of cell death and permanent loss of function; and interact with endogenous regenerative cells and/or other physiological mechanisms.

The regenerative cells may be used in their 'native' form as present in or separated and concentrated from the tissue using the systems and methods of the present invention or they may be modified by stimulation or priming with growth factors or other biologic response modifiers, by gene transfer (transient or stable transfer), by further sub-fractionation of the resultant population on the basis or physical properties (for example size or density), differential adherence to a solid phase material, expression of cell surface or intracellular molecules, cell culture or other ex vivo or in vivo manipulation, modification, or fractionation as further described herein. The regenerative cells may also be used in combination with other cells or devices such as synthetic or biologic scaffolds, materials or devices that deliver factors, drugs, chemicals or other agents that modify or enhance the relevant characteristics of the cells as further described herein.

As used herein, "regenerative cell composition" refers to the composition of cells typically present in a volume of liquid after a tissue, e.g., adipose tissue, is washed and at least partially disaggregated. For example, a regenerative cell composition of the invention comprises multiple different types of regenerative cells, including ASCs, endothelial cells, endothelial precursor cells, endothelial progenitor cells, macrophages, fibroblasts, pericytes, smooth muscle cells, preadipocytes, differentiated or de-differentiated adipocytes, keratinocytes, unipotent and multipotent progenitor and precursor cells (and their progeny), and lymphocytes. The regenerative cell composition may also contain one or more contaminants, such as collagen, which may be present in the tissue fragments, or residual collagenase or other enzyme or agent employed in or resulting from the tissue disaggregation process described herein.

As used herein, "regenerative medicine" refers to any therapeutic, structural or cosmetic benefit that is derived from the placement, either directly or indirectly, of regenerative cells into a subject. As used herein, "renal condition, disease or disorder" is intended to include all disorders characterized by insufficient, undesired or abnormal renal function. Treatment of a renal condition, disease or disorder is within the ambit of regenerative medicine. The phrase is also intended to mean any disease, disorder, syndrome, anomaly, pathology, or abnormal condition of the kidney or of the structure or function of its constituent parts., e.g., acute renal failure (ARF), acute tubular necrosis (ATN) (both ischemic ATN and nephrotoxic ATN), acute glomeruloneophritis (AGN), acute interstitial nephritis (AIN), chronic renal failure, diabetic nephropathy, hematuria, ischemic nephropathy, kidney cancer, nephrotic syndrome (NS), renal artery stenosis (RAS) and renal vascular hypertension. Insufficient or abnormal renal function can be the result of disease, injury and/or aging.

As used herein, the term "ischemia" refers to any localized tissue ischemia due to reduction of the inflow of blood. The term "ischemic ATN" refers to the death of the kidney's tubular cells due to the lack of oxygen. Certain medical and surgical situations are associated with a high risk for developing ischemic ATN, e.g., hypotension (low blood pressure), obstetric complications, obstructive jaundice (yellow-tinged skin caused by choked flow of bile), prolonged pre-renal state, sepsis (infection in the blood or tissues) and surgery. Diagnosis of ischemic ATN is generally supported by a positive history of risk factors.

As used herein, the term "nephrotoxic ATN" refers to the death of the kidney's tubular cells due to exposure to a toxic drug or molecule. Some medications and clinical materials that can cause nephrotoxic ATN include, e.g., aminoglycosides (antibacterial antibiotics such as streptomycin and gentamicin), amphotericin B (antibiotic used to treat some forms of meningitits and systemic fungal infections), cisplatin (anticancer agent used to treat late stage ovarian and testicular cancers) and radioisotopic contrast media (agent used in certain imaging studies). ATN can also occur in persons who suffer significant muscle trauma, such as during a crush injury. Suring such an injury, the muscle enzyme creatinine phophokinase (CPK) spills into the blood. If enough CPK is filtered through the glomeruli, it (via the protein myoglobulin) ultimately causes nephrotoxic ATN. ATN can also result from rhabdomyolysis following a significant muscle crush injury.

As used herein, the term "angiogenesis" refers to the process by which new blood vessels are generated from existing vasculature and tissue (Folkman, 1995). The phrase "repair or remodeling" refers to the reformation of existing vasculature. The alleviation of tissue ischemia is critically dependent upon angiogenesis. The spontaneous growth of new blood vessels provides collateral circulation in and around an ischemic area, improves blood flow, and alleviates the symptoms caused by the ischemia. Angiogenesis mediated diseases and disorders include acute myocardial infarction, ischemic cardiomyopathy, peripheral vascular disease, ischemic stroke, acute tubular necrosis, ischemic wounds-including AFT, sepsis, ischemic bowel disease, diabetic retinopathy, neuropathy and nephropathy, vasculitidies, ischemic encephalopathy, erectile dysfunction-physiologic, ischemic or traumatic spinal cord injuries, multiple organ system failure, ischemic gum disease, and transplant related ischemia.

As used herein, "stem cell" refers to a multipotent regenerative cell with the potential to differentiate into a variety of other cell types, which perform one or more specific functions and have the ability to self-renew. Some of the stem cells disclosed herein may be multipotent.

As used herein, "progenitor cell" refers to a multipotent regenerative cell with the potential to differentiate into more than one cell type and has limited or no ability to self-renew. "Progenitor cell", as used herein, also refers to a unipotent cell with the potential to differentiate into only a single cell type, which performs one or more specific functions and has limited or no ability to self-renew. In particular, as used herein, "endothelial progenitor cell" refers to a multipotent or unipotent cell with the potential to differentiate into vascular endothelial cells.

As used herein, "precursor cell" refers to a unipotent regenerative cell with the potential to differentiate into one cell type. Precursor cells and their progeny may retain extensive proliferative capacity, e.g., lymphocytes and endothelial cells, which can proliferate under appropriate conditions.

As used herein, the term "angiogenic factor" or "angiogenic protein" refers to any known protein, peptide or other agent capable of promoting growth of new blood vessels from existing vasculature ("angiogenesis"). Suitable angiogenic factors for use in the invention include, but are not limited to, Placenta Growth Factor (Luttun et al., 2002), Macrophage Colony Stimulating Factor (Aharinejad et al., 1995), Granulocyte Macrophage Colony Stimulating Factor (Buschmann et al., 2003), Vascular Endothelial Growth Factor (VEGF)-A, VEGF-A, VEGF-B, VEGF-C, VEGF-D, VEGF-E (Mints et al., 2002), neuropilin (Wang et al., 2003), fibroblast growth factor (FGF)-1, FGF-2(bFGF), FGF-3, FGF4, FGF-5, FGF-6 (Botta et al., 2000), Angiopoietin 1, Angiopoietin 2 (Sundberg et al., 2002), erythropoietin (Ribatti et al., 2003), BMP-2, BMP4, BMP-7 (Carano and Filvaroff, 2003), TGF-beta (Xiong et al., 2002), IGF-1 (Shigematsu et al., 1999), Osteopontin (Asou et al., 2001), Pleiotropin (Beecken et al., 2000), Activin (Lamouille et al., 2002), Endothelin-1 (Bagnato and Spinella, 2003) and combinations thereof. Angiogenic factors can act independently, or in combination with one another. When in combination, angiogenic factors can also act synergistically, whereby the combined effect of the factors is greater than the sum of the effects of the individual factors taken separately. The term "angiogenic factor" or "angiogenic protein" also encompasses functional analogues of such factors. Functional analogues include, for example, functional portions of the factors. Functional analogues also include anti-idiotypic antibodies which bind to the receptors of the factors and, thus, mimic the activity of the factors in promoting angiogenesis and/or tissue remodeling. Methods for generating such anti-idiotypic antibodies are well known in the art and are described, for example, in WO 97/23510, the contents of which are incorporated by reference herein.

Angiogenic factors used in the present invention can be produced or obtained from any suitable source. For example, the factors can be purified from their native sources, or produced synthetically or by recombinant expression. The factors can be administered to patients as a protein composition. Alternatively, the factors can be administered in the form of an expression plasmid encoding the factors. The construction of suitable expression plasmids is well known in the art. Suitable vectors for constructing expression plasmids include, for example, adenoviral vectors, retroviral vectors, adeno-associated viral vectors, RNA vectors, liposomes, cationic lipids, lentiviral vectors and transposons.

As used herein, the term "arteriogenesis" refers to the process of enhancing growth of collateral arteries and/or other arteries from pre-existing arteriolar connections (Carmeliet, 2000; Scholz et al., 2001; Scholz et al., 2002). More particularly, arteriogenesis is the in situ recruitment and expansion of arteries by proliferation of endothelial and smooth muscle cells from pre-existing arteriolar connections supplying blood to ischemic tissue, tumor or site of inflammation. These vessels largely grow outside the affected tissue and are important for the delivery of nutrients to the ischemic territory, the tumor or the site of inflammation. Arteriogenesis is part of the normal response to myocardial ischemia (Mills et al., 2000; Monteiro et al., 2003). In addition, the common surgical technique of a coronary artery bypass graft (CABG) is, in effect, no more than creation of an artificial collateral vessel (Sergeant et al., 1997). Thus, processes which enhance arteriogenesis following an infarct will improve blood flow to ischemic tissue resulting in decreased cell death and decreased infarct size. These improvements will result in improved cardiac function and therapeutic benefit.

As used herein "stem cell number" or "stem cell frequency" refers to the number of colonies observed in a clonogenic assay in which adipose derived cells (ADC) are plated at low cell density (<10,000 cells/well) and grown in growth medium supporting MSC growth (for example, DMEM/F12 medium supplemented with 10% fetal calf serum, 5% horse serum, and antibiotic/antimycotic agents). Cells are grown for two weeks after which cultures are stained with hematoxylin and colonies of more than 50 cells are counted as CFU-F. Stem cell frequency is calculated as the number of CFU-F observed per 100 nucleated cells plated (for example; 15 colonies counted in a plate initiated with 1,000 nucleated regenerative cells gives a stem cell frequency of 1.5%). Stem cell number is calculated as stem cell frequency multiplied by the total number of nucleated ADC cells obtained. A high percentage (~100%) of CFU-F grown from regenerative cells express the cell surface molecule CD105 which is also expressed by marrow-derived stem cells (Barry et al., 1999). CD105 is also expressed by adipose tissue-derived stem cells (Zuk et al., 2002).

As used herein, the term "adipose tissue" refers to fat including the connective tissue that stores fat. Adipose tissue contains multiple regenerative cell types, including ASCs and endothelial progenitor and precursor cells.

As used herein, the term "unit of adipose tissue" refers to a discrete or measurable amount of adipose tissue. A unit of adipose tissue may be measured by determining the weight and/or volume of the unit. Based on the data identified above, a unit of processed lipoaspirate, as removed from a patient, has a cellular component in which at least 0.1% of the cellular component is stem cells; that is, it has a stem cell frequency, determined as described above, of at least 0.1%. In reference to the disclosure herein, a unit of adipose tissue may refer to the entire amount of adipose tissue removed from a patient, or an amount that is less than the entire amount of adipose tissue removed from a patient. Thus, a unit of adipose tissue may be combined with another unit of adipose tissue to form a unit of adipose tissue that has a weight or volume that is the sum of the individual units.

As used herein, the term "portion" refers to an amount of a material that is less than a whole. A minor portion refers to an amount that is less than 50%, and a major portion refers to an amount greater than 50%. Thus, a unit of adipose tissue that is less than the entire amount of adipose tissue removed from a patient is a portion of the removed adipose tissue.

As used herein, the term "processed lipoaspirate" refers to adipose tissue that has been processed to separate the active cellular component (e.g., the component containing regenerative) from the mature adipocytes and connective tissue. This fraction is referred to herein as "adipose-derived cells" or "ADC." Typically, ADC refers to the pellet of regenerative cells obtained by washing and separating and concentrating the cells from the adipose tissue. The pellet is typically obtained by centrifuging a suspension of cells so that the cells aggregate at the bottom of a centrifuge chamber or cell concentrator.

As used herein, the terms "administering," "introducing," "delivering," "placement" and "transplanting" are used interchangeably herein and refer to the placement of the regenerative cells of the invention into a subject by a method or route which results in at least partial localization of the regenerative cells at a desired site. The regenerative cells can be administered by any appropriate route which results in delivery to a desired location in the subject where at least a portion of the cells or components of the cells remain viable. The period of viability of the cells after administration to a subject can be as short as a few hours, e.g., twenty-four hours, to a few days, to as long as several years.

As used herein, the term "treating" includes reducing or alleviating at least one adverse effect or symptom of a disease or disorder As used herein, "therapeutically effective dose of regenerative cells" refers to an amount of regenerative cells that are sufficient to bring about a beneficial or desired clinical effect. Said dose could be administered in one or more administrations. However, the precise determination of what would be considered an effective dose may be based on factors individual to each patient, including, but not limited to, the patient's age, size, type or extent of disease, stage of the disease, route of administration of the regenerative cells, the type or extent of supplemental therapy used, ongoing disease process and type of treatment desired (e.g., aggressive vs. conventional treatment).

As used herein, the term "subject" includes warm-blooded animals, preferably mammals, including humans. In a preferred embodiment, the subject is a primate. In an even more preferred embodiment, the subject is a human.

As previously set forth herein, regenerative cells, e.g., stem and progenitor cells, can be harvested from a wide variety of tissues. The system of the present invention may be used for all such tissues. Adipose tissue, however, is an especially rich source of regenerative cells. Accordingly, the system of the present invention is illustrated herein using adipose tissue as a source of regenerative cells by way of example only and not limitation.

Adipose tissue can be obtained by any method known to a person of ordinary skill in the art. For example, adipose tissue may be removed from a patient by liposuction (syringe or power assisted) or by lipectomy, e.g., suction-assisted lipoplasty, ultrasound-assisted lipoplasty, and excisional lipectomy or combinations thereof. The adipose tissue is removed and collected and may be processed in accordance with any of the embodiments of a system of the invention described herein. The amount of tissue collected depends on numerous factors, including the body mass index and age of the donor, the time available for collection, the availability of accessible adipose tissue harvest sites, concomitant and pre-existing medications and conditions (such as anticoagulant therapy), and the clinical purpose for which the tissue is being collected. For example, the regenerative cell percentage of 100 ml of adipose tissue extracted from a lean individual is greater than that extracted from an obese donor (Table I). This likely reflects a dilutive effect of the increased fat content in the obese individual. Therefore, it may be desirable, in accordance with one aspect of the invention, to obtain larger amounts of tissue from over-weight donors compared to the amounts that would be withdrawn from leaner patients. This observation also indicates that the utility of this invention is not limited to individuals with large amounts of adipose tissue.

TABLE I

Effect of Body Mass Index on Tissue and Cell Yield

| Body Mass Index Status | Amount of Tissue Obtained (g) | Total Regenerative Cell Yield ($\times 10^7$) |
| --- | --- | --- |
| Normal | 641 ± 142 | 2.1 ± 0.4 |
| Obese | 1,225 ± 173 | 2.4 ± 0.5 |
| p value | 0.03 | 0.6 |

After the adipose tissue is processed, the resulting regenerative cells are substantially free from mature adipocytes and connective tissue. Accordingly, the system of the present invention generates a heterogeneous plurality of adipose derived regenerative cells which may be used for research and/or therapeutic purposes. In a preferred embodiment, the cells are suitable for placement or re-infusion within the body of a recipient. In other embodiments, the cells may be used for research, e.g., the cells can be used to establish stem or progenitor cell lines which can survive for extended periods of time and be used for further study.

Reference will now be made in detail to the presently preferred embodiments of the invention, examples of which are illustrated in the accompanying drawings. Wherever possible, the same or similar reference numbers are used in the drawings and the description to refer to the same or like parts. It should be noted that the drawings are in simplified form and are not to precise scale. In reference to the disclosure herein, for purposes of convenience and clarity only, directional terms, such as, top, bottom, left, right, up, down, over, above, below, beneath, rear, front, distal, and proximal are used with respect to the accompanying drawings. Such directional terms should not be construed to limit the scope of the invention in any manner.

Although the disclosure herein refers to certain illustrated embodiments, it is to be understood that these embodiments are presented by way of example and not by way of limitation. The intent of the following detailed description, although discussing exemplary embodiments, is to be construed to cover all modifications, alternatives, and equivalents of the embodiments as may fall within the spirit and scope of the invention as defined by the appended claims. The present invention may be utilized in conjunction with various medical procedures that are conventionally used in the art.

Referring now to the Figures, a system 10 of the present invention is generally comprised of one or more of a tissue collection chamber 20, a processing chamber 30, a waste chamber 40, an output chamber 50 and a sample chamber 60. The various chambers are coupled together via one or more conduits 12 such that fluids containing biological material may pass from one chamber to another while maintaining a closed, sterile fluid/tissue pathway. The conduits may comprise rigid or flexible bodies referred to interchangeably herein as lumens and tubing, respectively. In certain embodiments, the conduits are in the form of flexible tubing, such as polyethylene tubing conventionally used in clinical settings, silicone or any other material known in the art. The conduits 12 can vary in size depending on whether passage of fluid or tissue is desired. The conduits 12 may also vary in size depending on the amount of tissue or fluid that is cycled through the system. For example, for the passage of fluid, the conduits may have a diameter ranging from about 0.060 to about 0.750 inches and for the passage of tissue, the conduits may have a diameter ranging from 0.312 to 0.750 inches. Generally, the size of the conduits is selected to balance the volume the conduits can accommodate and the time required to transport the tissue or fluids through said conduits. In automated embodiments of the system, the foregoing parameters, i.e., volume and time for transport, must be identified such that the appropriate signals can be transmitted to the processing device of the system. This allows the device to move accurate volumes of liquid and tissue from one chamber to another. The flexile tubing used should be capable of withstanding negative pressure to reduce the likelihood of collapse. The flexible tubing used should also be capable of withstanding positive pressure which is generated by, for example, a positive displacement pump, which may be used in the system.

All the chambers of the system may be comprised of one or more ports, e.g., outlet 22 or inlet 21 ports, which accept standard IV, syringe and suction tubing connections. The ports may be a sealed port such as a rubber septum closed syringe needle access port 51. The inlet ports may be coupled to one or more cannulas (not shown) by way of conduits. For example, a tissue inlet port 21 may be coupled to an integrated single use liposuction cannula and the conduit may be a flexible tubing. The conduits are generally positioned to provide fluid passageways from one chamber of the system to another. Towards this end, the conduits and ports may be coupled to, for example, a suction device (not shown) which may be manually or automatically operated. The suction device may be, e.g., a syringe or an electric pump. The suction device should be capable of providing sufficient negative pressure to aspirate tissue from a patient. Generally, any suitable suction device known to one of ordinary skill in the art, e.g., a surgeon, may be used.

The conduits 12 may further comprise one or more clamps (not shown) to control the flow of material among various components of the system. The clamps are useful for maintaining the sterility of the system by effectively sealing different regions of the system. Alternatively, the conduits 12 may comprise one or more valves 14 that control the flow of material through the system. The valves 14 are identified as open circles in the Figures. In preferred embodiments, the valves may be electromechanical pinch valves. In another embodiment, the valves may be pneumatic valves. In yet other embodiments, the valves may be hydraulic valves or mechanical valves. Such valves are preferably activated by a control system which may be coupled to levers. The levers may be manually manipulated such that the levers are activated. In automated embodiments, the control system may be coupled to the levers as well as to a processing device which may activate the valves at pre-determined activation conditions. In certain automated embodiments, activation of the valves may be partially automated and partially subject to the user's preference such that the process may be optimized. In yet other embodiments, certain valves may be activated manually and others automatically through the processing device. The valves 14 may also be used in conjunction with one or more pumps, e.g., peristaltic pumps 34 or positive displacement pumps (not shown). The conduits 12 and/or the valves 14 may also be comprised of sensors 29, e.g., optical sensors, ultrasonic sensors, pressure sensors or other forms of monitors known in the art that are capable of distinguishing among the various fluid components and fluid levels that flow through the system. In a preferred embodiment, the sensors 29 may be optical sensors.

The system may also include a plurality of filters 36. In certain embodiments, the filters may be within a chamber of the system 28. Different chambers within the system may be comprised of different filters. The filters are effective to separate the regenerative cells, e.g., stem cells and/or progenitor cells, from undesirable cells and disaggregation agents that may be used in accordance with the system. In one embodiment, a filter assembly 36 includes a hollow fiber filtration device. In another embodiment, a filter assembly 36 includes a percolative filtration device, which may or may not be used with a sedimentation process. In a further embodiment, the filter assembly 36 comprises a centrifugation device, which may or may not be used with an elutriation device and process. In yet another embodiment, the system comprises a combination of these filtering devices. The filtration functions of the present invention can be two-fold, with some filters removing things from the final concentration such as collagen, free lipid, free adipocytes and residual collagenase, and with other filters being used to concentrate the final product. The filters of the system may be comprised of a plurality of pores ranging in diameters and/or length from 20 to 800 µm. In a preferred embodiment, the collection chamber 20 has a prefixed filter 28 with a plurality of pores ranging from 80 to 400 µm. In another preferred embodiment, the collection chamber 20 has a prefixed filter 28 with a plurality of 265 µm pores. In other embodiments, the filters may be detachable and/or disposable.

The system may also be comprised of one or more temperature control devices (not shown) that are positioned to adjust the temperature of the material contained within one or more chambers of the system. The temperature control device may be a heater, a cooler or both, i.e., it may be able to switch between a heater and a cooler. The temperature device may adjust the temperature of any of the material passing through the system, including the tissue, the disaggregation agents, the resuspension agents, the rinsing agents, the washing agents or the additives. For example, heating of adipose tissue facilitates disaggregation whereas the cooling of the regenerative cell output is desirable to maintain viability. Also, if pre-warmed reagents are needed for optimal tissue processing, the role of the temperature device would be to maintain the pre-determined temperature rather than to increase or decrease the temperature.

To maintain a closed, sterile fluid/tissue pathway, all ports and valves may comprise a closure that maintains the sealed configuration of the system. The closure may be a membrane that is impermeable to fluid, air and other contaminants or it may be any other suitable closure known in the art. Furthermore, all ports of the system may be designed such that they can accommodate syringes, needles or other devices for withdrawing the materials in the chambers without compromising the sterility of the system.

As set forth herein, tissue may be extracted from a patient via any art recognized method. The aspirated tissue may be extracted prior to being placed in the system for processing. The aspirated tissue is typically transferred to the collection chamber 20 through conduits 12 via a sealed entry port, such as a rubber septum closed syringe needle access port (not shown on collection chamber). Alternatively, the tissue extraction step may be part of the system. For example, the collection chamber 20 may be comprised of a vacuum line 11 which facilitates tissue removal using a standard cannula inserted into the patient. Thus, in this embodiment, the entire system is attached to the patient. The tissue may be introduced into the collection chamber 20 through an inlet port 21 via a conduit such as 12a which are part of a closed sterile pathway. The collection chamber 20 may be comprised of a plurality of flexible or rigid canisters or cylinders or combinations thereof. For example, the collection chamber 20 may be comprised of one or more rigid canisters of varying sizes. The collection chamber 20 may also be comprised of one or more flexible bags. In such systems, the bag is preferably provided with a support, such as in internal or external frame, that helps reduce the likelihood that the bag will collapse upon the application of suction to the bag. The collection chamber 20 is sized to hold the requisite amount of saline to appropriately wash and disaggregate the tissue prior to the wash and concentrate stage of the process performed in the processing chamber 30. Preferably, the volume of tissue or fluid present in the collection chamber 20 is easily ascertainable to the naked eye. For example, to obtain regenerative cells from adipose tissue, a suitable collection chamber has the capacity to hold 800 ml of lipoaspirate and 1200 ml of saline. Accordingly, in one embodiment, the collection chamber 20 has a capacity of at least 2 liters. In another embodiment, to separate and concentrate red blood cells from blood, the collection chamber 20 has a capacity of at least 1.5 liters. Generally, the size of the collection chamber 20 will vary depending on the type and amount of tissue collected from the patient. The collection chamber 20 may be sized to hold as little as about 5 ml to up to about 2 liters of tissue. For smaller tissue volumes, e.g., 5 mls to 100 mls, the tissue may be gathered in a syringe prior to transfer to the collection chamber 20.

The collection chamber 20 may be constructed using any suitable biocompatible material that can be sterilized. In a preferred embodiment, the collection chamber 20 is constructed of disposable material that meets biocompatibility requirements for intravascular contact as described in the ISO 10993 standard. For example, polycarbonate acrylic or ABS may be used. The fluid path of the collection chamber 20 is preferably pyrogen free, i.e., suitable for blood use without danger of disease transmittal. In one embodiment, the collection chamber 20 is constructed of a material that allows the user to visually determine the approximate volume of tissue present in the chamber. In other embodiments, the volume of tissue and/or fluid in the collection chamber 20 is determined by automated sensors 29. The collection chamber 20 is preferably designed such that in an automated embodiment, the system can determine the volume of tissue and/or fluid within the chamber with a reasonable degree of accuracy. In a preferred embodiment, the system senses the volume within the collection chamber with an accuracy of plus or minus fifteen percent.

Figure 5:
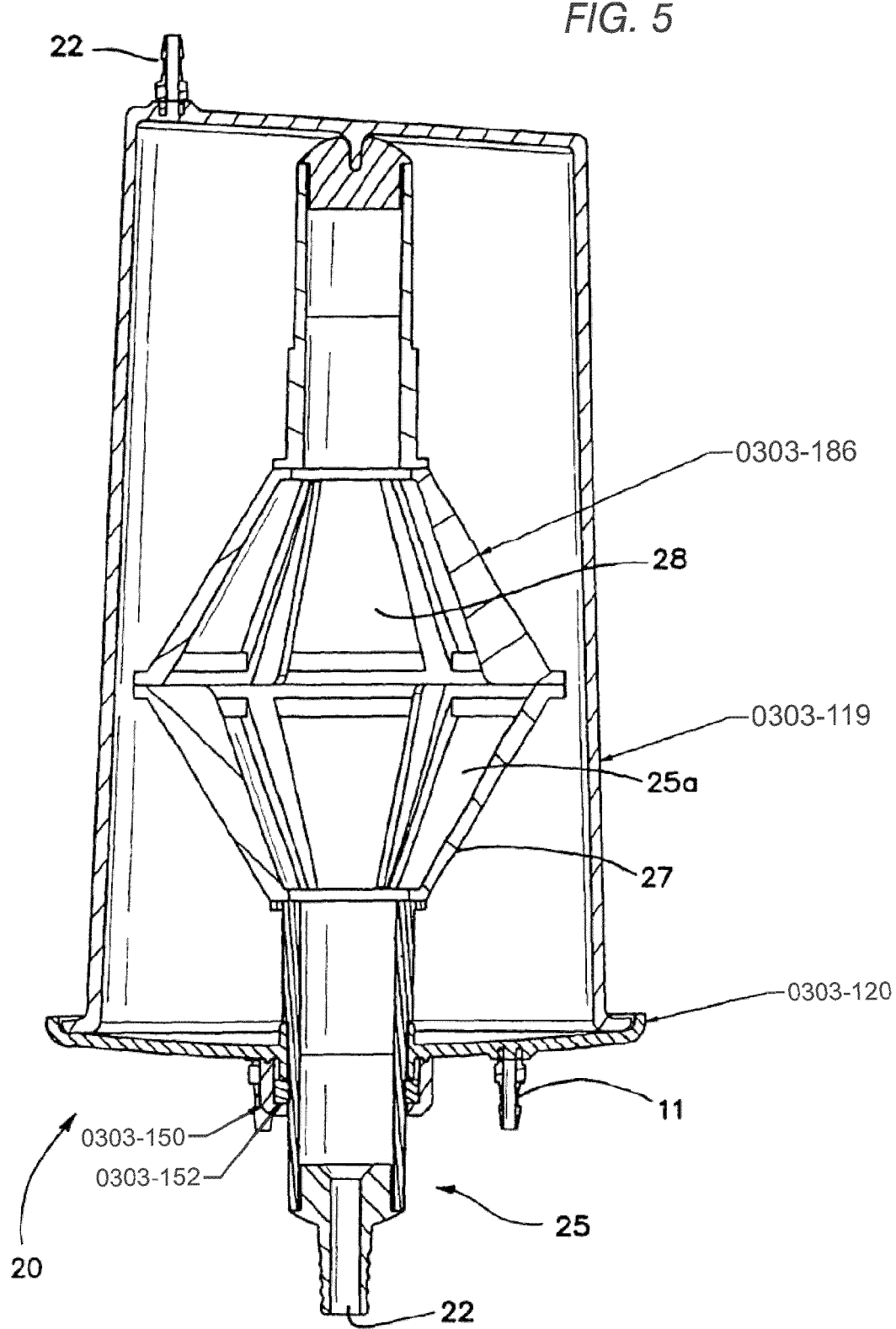
FIG. 5 is a sectional view of a collection chamber including a prefixed filter utilized in a system for separating regenerative cells from tissue.

In a particular embodiment provided by way of example only, the collection chamber 20 is in the form of a rigid chamber, for example, a chamber constructed of a medical grade polycarbonate containing a roughly conical prefixed filter 28 of medical grade polyester with a mesh size of 265 µm (see FIG. 5). The rigid tissue collection container may have a size of approximately eight inches high and approximately five inches in diameter; the wall thickness may be about 0.125 inches. The interior of the cylinder may be accessed through, for example, one or more ports for suction tubing, one or more ports with tubing for connection through sterile docking technology, and/or one or more ports for needle puncture access through a rubber septum. The prefixed filter 28 in the interior of the collection chamber 20 is preferably structured to retain adipose tissue and to pass non-adipose tissue as, for example, the tissues are removed from the patient. More specifically, the filter 28 may allow passage of free lipid, blood, and saline, while retaining fragments of adipose tissue during, or in another embodiment after, the initial harvesting of the adipose tissue. In that regard, the filter 28 includes a plurality of pores, of either the same or different sizes, but ranging in size from about 20 µm to 5 mm. In a preferred embodiment, the filter 28 includes a plurality of 400 µm pores. In a preferred embodiment, the filter 28 is a medical grade polyester mesh of around 200 µm thickness with a pore size of around 265 µm and around 47% open area. This material holds the tissue during rinsing but allows cells to pass out through the mesh following tissue disaggregation. Thus, when the tissues are aspirated from the patient, non-adipose tissue may be separated from adipose tissue. The same functionality could be achieved with different materials, mesh size, and the number and type of ports. For example, mesh pore sizes smaller than 100 µm or as large as several thousand microns would achieve the same purpose of allowing passage of saline and blood cells while retaining adipose tissue aggregates and fragments. Similarly, the same purpose could be achieved by use of an alternative rigid plastic material, or by many other modifications that would be known to those skilled in the art.

The system 10 may also be comprised of one or more solution sources 22. The solution source may comprise a washing solution source 23, and a tissue disaggregation agent source 24, such as collagenase. The collection chamber 20 is comprised of closed fluid pathways that allows for the washing and disaggregating solutions or agents to be added to the tissue in an aseptic manner.

The containers for the washing solution 23 and the disaggregation agents 24 may be any suitable container that can hold their contents in a sterile manner, e.g., a collapsible bag, such as an IV bag used in clinical settings. These containers may have conduits 12, such as conduit 12e, coupled to the collection chamber 20 so that the washing solution and the disaggregation agent may be delivered to the interior of the collection chamber 20. The washing solution and the disaggregation agent may be delivered to the interior of the collection chamber 20 through any art-recognized manner, including simple gravity pressure applied to the outside of the containers for the saline 23 and/or the disaggregation agents 24 or by placement of a positive displacement pump on the conduits, e.g., conduit 12d in FIG. 4. In automated embodiments, the processing device of the system calculates various parameters, e.g., the volume of saline and time or number of cycles required for washing as well as the concentration or amount of disaggregation agent and the time required for disaggregation based on information initially entered by the user (e.g., volume of tissue being processed). Alternatively, the amounts, times etc. can be manually manipulated by the user.

The tissue and/or fluid within the collection chamber should be maintained at a temperature ranging from 30 degrees Celsius to 40 degrees Celsius. In a preferred embodiment, the temperature of the suspension inside the collection chamber is maintained at 37 degrees Celsius. In certain embodiments, if the surgical procedure or therapeutic application needs to be delayed, the selected tissue may be stored in the collection chamber for later use. The tissue may be stored at or about room temperature or at about 4 degrees Celsius for up to 96 hours.

The washing solution may be any solution known to one of skill in the art, including saline or any other buffered or unbuffered electrolyte solution. The types of tissue being processed will dictate the types or combinations of washing solutions used. Typically, the washing solution, such as saline, enters the collection chamber 20 after the adipose tissue has been removed from the patient and placed in the collection chamber. However, the washing solution may be delivered to the collection chamber 20 before the adipose tissue is extracted, or may be delivered to the collection chamber 20 concurrently with the adipose tissue. In the collection chamber 20, the washing solution and the extracted adipose tissue may be mixed by any means including the methods described below.

For example, the tissue may be washed by agitation (which maximizes cell viability and minimizes the amount of free lipid released). In one embodiment, the tissue is agitated by rotating the entire collection chamber 20 through an arc of varying degrees (e.g., through an arc of about 45 degrees to about 90 degrees) at varying speeds, e.g., about 30 revolutions per minute. In other embodiments, the tissue is agitated by rotating the entire collection chamber 20, wherein the collection chamber 20 is comprised of one or more paddles or protrusions rigidly attached to an inside surface of the collection chamber, through an arc of varying degrees (e.g., through an arc of about 45 degrees to about 90 degrees) at varying speeds, e.g., about 30 revolutions per minute. The rotation of the collection chamber 20 described above may be accomplished by a drive mechanism attached to or in proximity with the collection chamber 20. The drive mechanism may be a simple belt or gear or other drive mechanism known in the art. The speed of the rotation may be, for example, 30 revolutions per minute. Generally, higher speeds have been found to generate larger volumes of free lipids and may not be optimal.

In other embodiments, the tissue is agitated by placing a rotatable shaft 25 inside the collection chamber 20, wherein the rotatable shaft is comprised of one or more paddles 25a or protrusions rigidly attached to the rotatable shaft 25 which pass through the mixture as the shaft is being rotated. In certain embodiments, the rotatable shaft 25 with rigidly attached 25a paddles may be rested on the bottom of the collection chamber 20. This may be accomplished, for example, by placing the paddle-like device into a spinning magnetic field (e.g., magnetic stirrer). Alternatively, agitating of the tissue may be accomplished using a simple agitator known in the art, i.e. a device implementing shaking up and down without rotation. The tissue may also be washed using any other art-recognized means including rocking, stirring, inversion, etc.

After a desired amount of wash cycles, a tissue disaggregation agent may be delivered to the collection chamber 20 to separate the regenerative cells from the remaining adipose tissue components. The disaggregation agent may be any disaggregation agent known to one of skill in the art. Disaggregation agents that may be used include neutral proteases, collagenase, trypsin, lipase, hyaluronidase, deoxyribonuclease, members of the Blendzyme enzyme mixture family, e.g., Liberase H1, pepsin, ultrasonic or other physical energy, lasers, microwaves, other mechanical devices and/or combinations thereof. A preferred disaggregation agent of the invention is collagenase. The disaggregation agents may be added with other solutions. For example, saline, such as saline delivered from a saline source 23 as described above, may be added to the adipose tissue along with or immediately followed by addition of collagenase. In one embodiment, the washed adipose tissue is mixed with a collagenase-containing enzyme solution at or around 37° C. for about 20-60 minutes. In other embodiments, a higher concentration of collagenase or similar agent may be added to decrease the digestion time. The washed adipose tissue and the tissue disaggregation agent may then be agitated in manners similar to the agitation methods described above, until the washed adipose tissue is disaggregated. For example, the washed adipose tissue and the tissue disaggregation agent may be agitated by rotating the entire collection chamber through an arc of approximately 90 degrees, by having a shaft which contains one or more paddles which pass through the solution as the shaft is being rotated, and/or by rotating the entire collection chamber which contains paddles or protrusions on the inside surface of the collection chamber.

Depending on the purpose for which the adipose derived cells will be used, the adipose tissue may either be partially disaggregated, or completely disaggregated. For example, in embodiments in which the adipose derived cells are to be combined with a unit of adipose tissue, it may be desirable to partially disaggregate the harvested adipose tissue, to remove a portion of the partially disaggregated adipose tissue, and then continue disaggregating the remaining portion of adipose tissue remaining in the collection chamber. Alternatively, a portion of washed adipose tissue may be removed and set aside in a sample container prior to any digestion. In another embodiment, harvested adipose tissue is partially disaggregated to concentrate cells before being reintroduced back into the patient. In one embodiment, the adipose tissue is mixed with a tissue disaggregation agent for a period of time generally less than about 20 minutes. A portion of the partially disaggregated tissue may then be removed from the collection chamber, and the remaining partially disaggregated tissue may be further disaggregated by mixing the adipose tissue with a tissue disaggregation agent for another 40 minutes. When the adipose derived cells are to be used as an essentially pure population of regenerative cells, the adipose tissue may be fully disaggregated.

After digestion, the tissue and disaggregation agent solution is allowed to settle for a period of time sufficient to allow the buoyant and non-buoyant components of the solution to differentiate within the collection chamber. Typically, the time ranges from about 15 seconds to several minutes but other times may be implemented in modified embodiments. The buoyant layer is comprised of the regenerative cells that require further washing and concentrating. The non-buoyant layer comprises blood, collagen, lipids and other non-regenerative cell components of the tissue. The non-buoyant layer must be removed to the waste chamber.

Accordingly, the collection chamber 20 is preferably comprised of an outlet port 22 at the lowest point of the chamber such that blood and other non-buoyant components of the tissue may be drained to one or more waste containers 40 via one or more conduits 12. The collection chamber 20 is generally in (or may be placed in) an upright position such that the outlet ports 22 are located at the bottom of the collection chamber. The draining may be passive or active. For example, the non-buoyant components described above could be drained using gravity, by applying positive or negative pressure, by use of pumps 34 or by use of vents 32. In automated embodiments, the processing device can signal certain valves and/or pumps to drain the non-buoyant layer from the collection chamber 20. The automated embodiments may also be comprised of sensors 29 which can detect when the interface between the buoyant and non-buoyant liquids has been reached. The automated embodiments may also be comprised of a sensor 29, e.g., an optical sensor, which may be capable of detecting a change in the light refraction of the effluent which is flowing in the conduit leading out of the collection chamber. The appropriate change in the light refraction may signal the presence of the buoyant layer in the outgoing conduits which indicates that the non-buoyant layer has been drained. The sensor 29 can then signal the processing device to proceed with the next step.

In certain embodiments however, the tissue may be processed to retrieve the non-regenerative cell component of the tissue. For example, in certain therapeutic or research applications, collagen, proteins, matrix or stromal components, lipids, adipocytes or other components of the tissue may be desired. In such embodiments, it is the buoyant layer comprising the regenerative cells that must be removed as described above to the waste chamber. The non-buoyant layer is then retained in the system for further processing as needed.

Once the non-buoyant layer is removed, the buoyant layer comprising the regenerative cells may be washed one or more times to remove residual contaminants. Accordingly, the collection chamber 20 typically includes one or more ports 21 for permitting the washing solution to be delivered to the interior of the chamber, and one or more ports 22 for permitting waste and other materials to be directed out from the collection chamber 20. For example, the collection chamber may include one or more sealed entry ports as described herein. The collection chamber 20 may also include one or more caps (not shown), such as a top cap and a bottom cap to further ensure that the system remains sterile while washing solution is delivered into the collection chamber and/or waste is transported out. The ports 21 may be provided on the caps of the collection chamber or on a sidewall of the collection chamber.

The process of washing with fresh wash solution may be repeated until the residual content of non-buoyant contaminants in the solution reaches a pre-determined level. In other words, the remaining material in the collection chamber 20, which comprises the buoyant material of the mixture described above, including adipose tissue fragments, may be washed one or more additional times until the amount of undesired material is reduced to a desired pre-determined level. One method of determining the end point of the washing is to measure the amount of red blood cells in the tissue solution. This can be accomplished by measuring the light absorbed on the 540 nm wavelength. In a preferred embodiment, a range between about 0.546 and about 0.842 is deemed acceptable.

During the washing and/or disaggregation, one or more additives may be added to the various containers as needed to enhance the results. Some examples of additives include agents that optimize washing and disaggregation, additives that enhance the viability of the active cell population during processing, anti-microbial agents (e.g., antibiotics), additives that lyse adipocytes and/or red blood cells, or additives that enrich for cell populations of interest (by differential adherence to solid phase moieties or to otherwise promote the substantial reduction or enrichment of cell populations). Other possible additives include those that promote recovery and viability of regenerative cells (for example, caspase inhibitors) or which reduce the likelihood of adverse reaction on infusion or emplacement (for example, inhibitors of re-aggregation of cells or connective tissue).

After a sufficient settling time has elapsed, the non-buoyant fraction of the resulting mixture of washed adipose tissue fragments and tissue disaggregation agents will contain regenerative cells, e.g., stem cells and other adipose derived progenitor cells. As discussed herein, the non-buoyant fraction containing the regenerative cells will be transferred to the processing chamber 30 wherein the regenerative cells of interest, such as the adipose derived stem cells, will be separated from other cells and materials present in the non-buoyant fraction of the mixture. This non-buoyant fraction is referred to herein as the regenerative cell composition and comprises multiple different types of cells, including stem cells, progenitor cells, endothelial precursor cells, adipocytes and other regenerative cells described herein. The regenerative cell composition may also contain one or more contaminants, such as collagen and other connective tissue proteins and fragments thereof, which were present in the adipose tissue fragments, or residual collagenase from the tissue disaggregation process.

The processing chamber 30 of the invention is preferably positioned within the system such that the regenerative cell composition moves from the collection chamber 20 to the processing chamber 30 by way of tubing 12, valves 14 and pump 34 in a sterile manner. The processing chamber is sized to accommodate tissue/fluid mixtures ranging from 10 mL to 1.2 L. In a preferred embodiment, the processing chamber is sized to accommodate 800 mLs. In certain embodiments, the entire regenerative cell composition from the collection chamber 20 is directed to the processing chamber 30. However, in other embodiments, a portion of the regenerative cell composition is directed to the processing chamber 30, and another portion is directed to a different region of the system, e.g., the sample chamber 60, to be recombined with cells processed in the processing chamber 30 at a later time.

Figure 6:
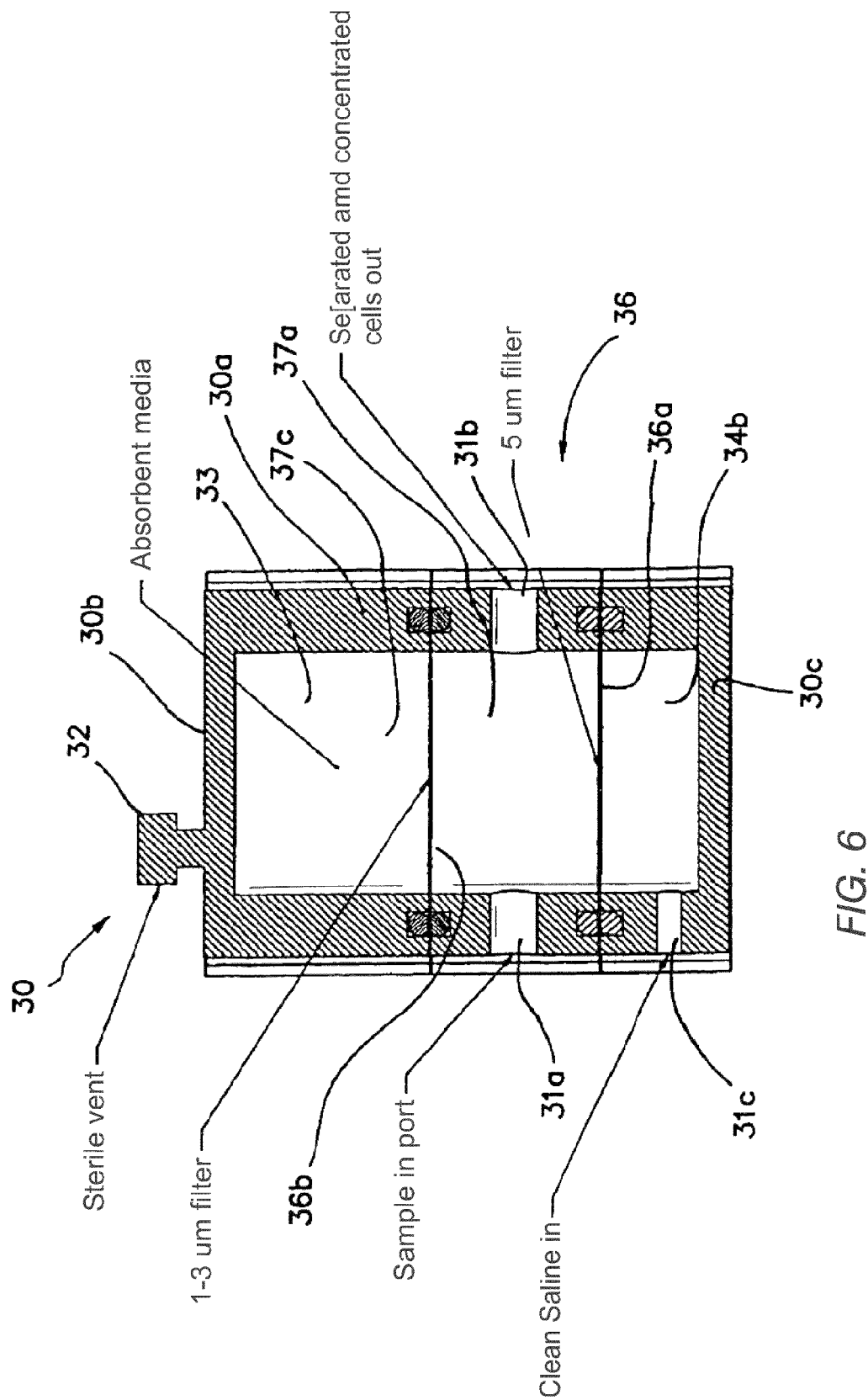
FIG. 6 is a sectional view of a processing chamber of a system for separating regenerative cells from tissue utilizing a percolative filtration system.

The processing chamber 30 may be constructed using any suitable biocompatible material that can be sterilized. In a preferred embodiment, the processing chamber 30 is constructed of disposable material that meets biocompatibility requirements for intravascular contact, as described in the ISO 10993 standard. For example, polycarbonate, acrylic, ABS, ethylene vinyl acetate or styrene-butadiene copolymers (SBC) may be used. In another embodiment, the fluid path of the disposable processing chamber is pyrogen free. The processing chamber may be in the form of a plastic bag, such as those conventionally used in processing blood in blood banks; or in other embodiments, it may be structurally rigid (FIG. 6). In one embodiment, the processing chamber 30 may be similar to the processing chamber disclosed in commonly owned U.S. application Ser. No. 10/316,127, filed Dec. 7, 2001 and U.S. application Ser. No. 10/325,728, filed Dec. 20, 2002, the contents of which in their entirety are hereby incorporated by reference.

The processing chamber 30 may be constructed in any manner suitable for separating and concentrating cells, including filtration and centrifugation and/or combinations thereof. In certain embodiments, the regenerative cell composition from the collection chamber 20 is introduced into the processing chamber 30 where the composition can be filtered to separate and/or concentrate a particular regenerative cell population. Cell filtration is a method of separating particular components and cells from other different components or types of cells. For example, the regenerative cell composition of the invention comprises multiple different types of cells, including stem cells, progenitor cells and adipocytes, as well as one or more contaminants, such as collagen, which was present in the adipose tissue fragments, or residual collagenase from the tissue disaggregation process. The filters 36 present in the processing chamber 30 may allow for separation and concentration of a particular subpopulation of regenerative cells, e.g., stem cells or endothelial progenitors cells etc.

Some variables which are associated with filtration of cells from a liquid include, but are not limited to, pore size of the filter media, geometry (shape) of the pore, surface area of the filter, flow direction of the solution being filtered, trans-membrane pressure, dilution of the particular cell population, particulate size and shape as well as cell size and cell viability. In accordance with the disclosure herein, the particular cells that are desired to be separated or filtered are typically adipose derived stem cells. However, in certain embodiments, the particular cells may include adipose derived progenitor cells, such as endothelial precursor cells, alone or in combination with the stem cells.

Figure 2:
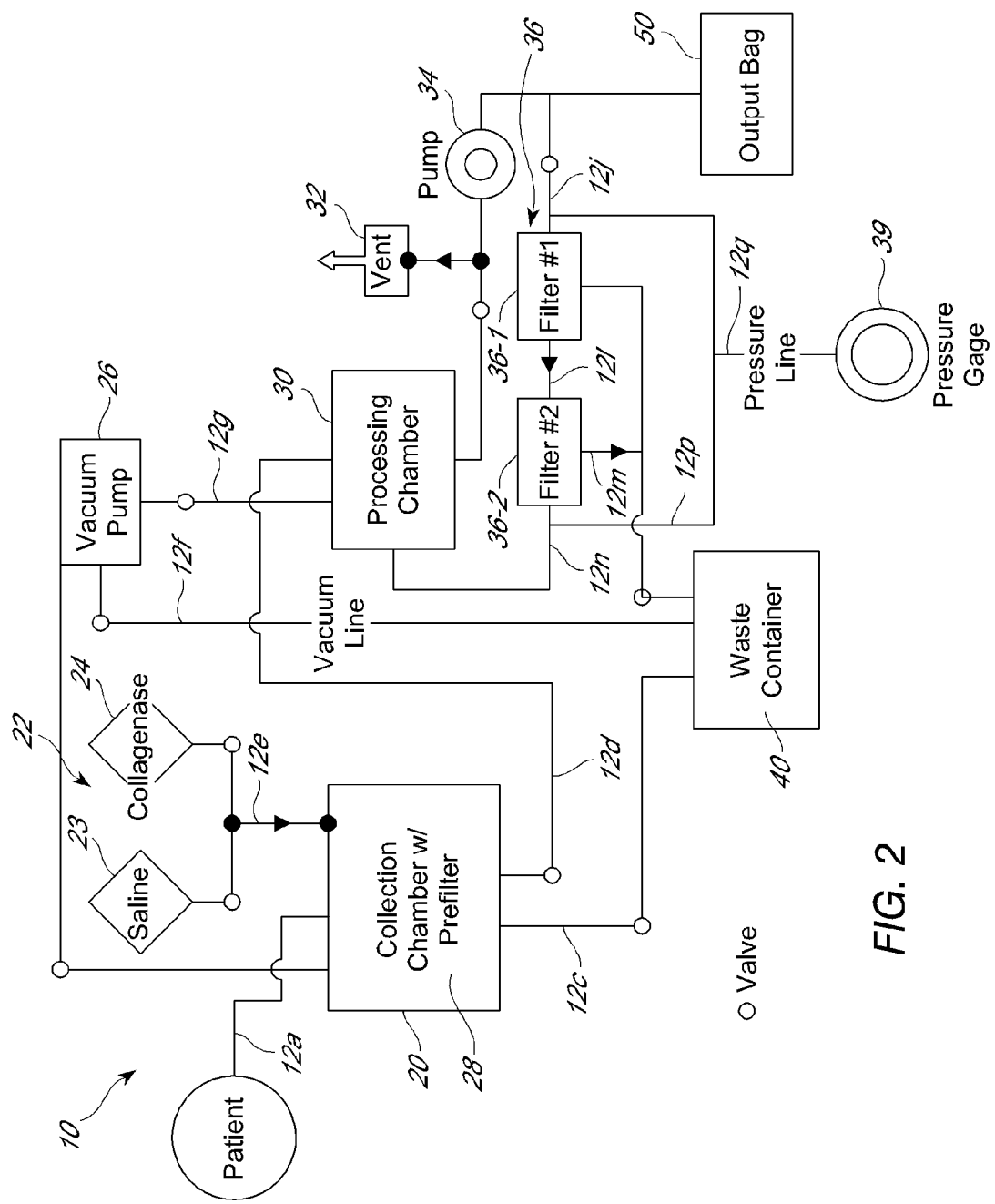
FIG. 2 is an illustration of a system similar to FIG. 1 having a plurality of filter assemblies in a serial configuration.
Figure 3:
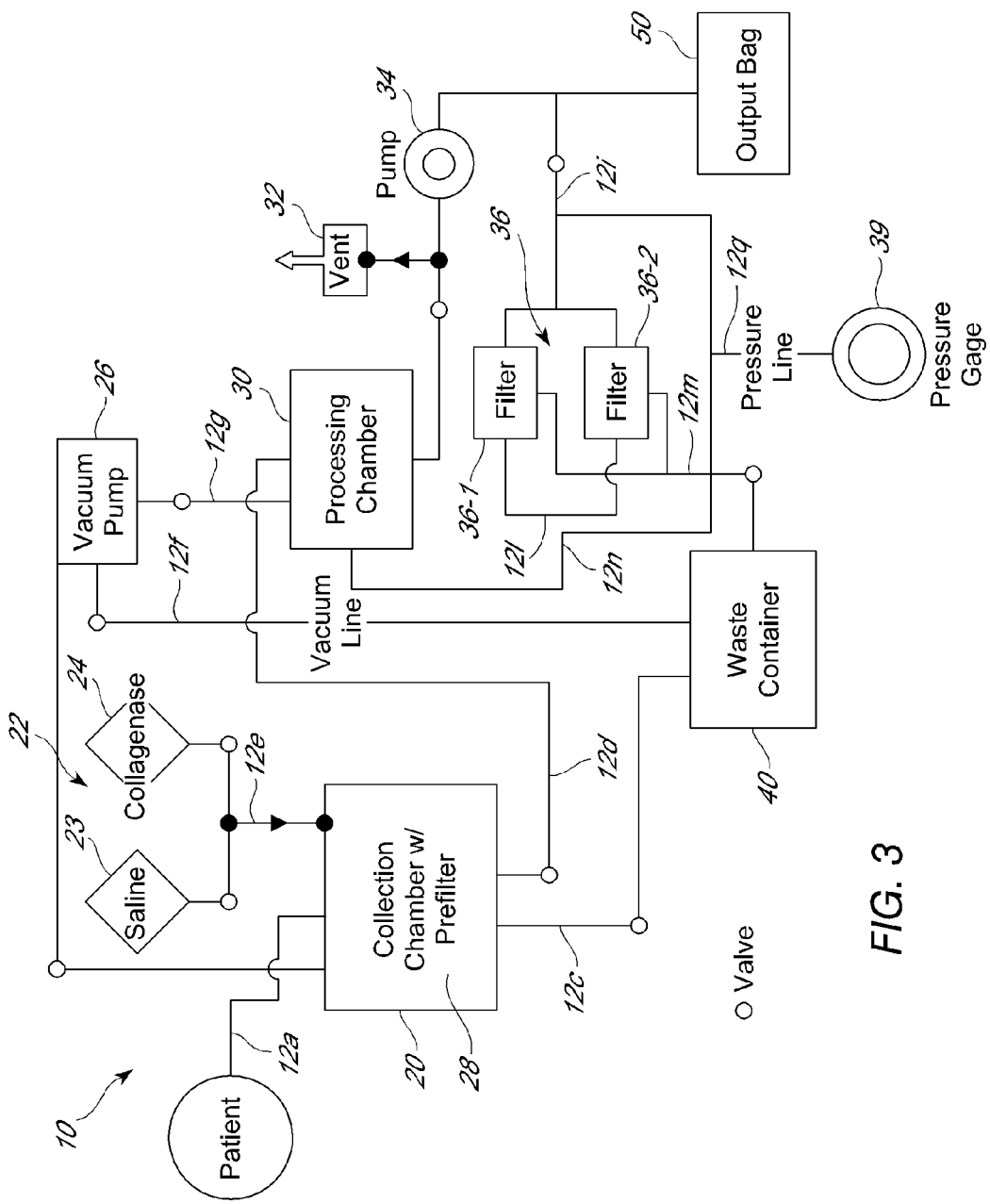
FIG. 3 is an illustration of a system similar to FIG. 1 having a plurality of filter assemblies in a parallel configuration.

The regenerative cell composition may be directed through a filter assembly, such as filter assembly 36. In certain embodiments, the filter assembly 36 comprises a plurality of filters which are structured to perform different functions and separate the regenerative cell composition into distinct parts or components. For example, one of the filters may be configured to separate collagen from the regenerative cell composition, one of the filters may be configured to separate adipocytes and/or lipid components from the regenerative cell composition, and one of the filters may be configured to separate residual enzymes, such as the tissue disaggregation agent, from the regenerative cell composition. In certain embodiments, one of the filters is capable of performing two functions, such as separating collagen and the tissue disaggregation agent from the composition. The plurality of filters are typically serially arranged; however, at least a portion of the filters may be arranged in parallel, as well. A serial arrangement of the filters of the filter assembly 36 is shown in FIG. 2. A parallel arrangement of the filters of the filter assembly 36 is shown in FIG. 3.

In one embodiment, the filter assembly 36 comprises a first filter, a second filter, and a third filter. The first filter is configured to remove collagen particles present in the regenerative cell composition. These collagen particles are typically approximately 0.1 microns in diameter and can be up to 20 microns long. The collagen particles may be of varying sizes depending on the digestion. They also may be fibrils, meaning they have twists and turns. Any of the filters described herein may be made 25 from polyethersulfone, polyester, PTFE, polypropylene, PVDF, or possibly cellulose. There are two possibilities for filtering the collagen. One is to try to remove the larger particles first, letting the cells go through, which would require for example a filter probably in the 10 micron range. The second method is to use a smaller size filter, such as 4.5 micron, with the intent that the collagen would be well digested, so as to trap the cells, and let the collagen pass through. This would require a means to float the cells back 30 off the filter. There may also be a possibility of implementing a filter which would attract and hold the collagen fibers.

The second filter is configured to remove free immature adipocytes which are not buoyant in the regenerative cell composition. In one embodiment the second filter can be constructed of polyester and have a pore size between about 30 and about 50 microns with a preferred pore size being about 40 microns. Although referred to as a second filter, placement of such a device may be in a first, rather than second, position to facilitate an initial removal of larger cells and particles. The third filter is configured to remove the unused or residual collagenase or other tissue disaggregation agent present in the composition. In a preferred implementation, the collagenase may degenerate over time. In one embodiment, the third filter comprises a plurality of pores having a diameter, or length less than 1 μm. In certain embodiments, the pores may have diameters that are smaller than 1 μm. In other embodiments, the pores have diameters between 10 kD and 5 microns. In certain embodiments, the third filter may be configured to concentrate the regenerative cell population into a small volume of saline or other washing solution, as discussed herein. As presently preferred, only the final filter is the hollow fiber unit. It is not necessary for any of the filters to be of the hollow fiber type. The hollow fiber unit is used for the final filter in a preferred implementation because it is the most efficient in removing the collagenase with the smallest detrimental effect to the regenerative cells. In an embodiment wherein the device is a collection of off the shelf items, the three filters are in separate housings. It is feasible to have the first and second filters combined into one housing if a hollow fiber unit is used for the third filter. If the final filter is not a hollow fiber set-up then all three filters can be contained in one housing.

The filters of the filter assembly 36 may be located in the processing chamber 30 or may be provided as components separate from the processing chamber 30. In addition, the filters of the filter assembly 36 may be provided in multiple processing chambers or in an inline fashion. In certain embodiments, the conduits or tubing may act as a processing chamber or chambers. The processing chamber can be reduced in size such that it becomes the inside volume of the conduits which connect the filters. This type of system will function correctly if the-volume of tissue solution is sized appropriately. Thus, the conduits may act as the processing chamber by containing the fluid with cells as it is being run through the filters. Care may be taken to minimize the volume of the conduits so that cells/tissue are not unnecessarily lost in the process of priming and running the system.

Referring to the embodiment described above, the regenerative cell composition, containing the washed cells and residual collagen, adipocytes, and/or undigested tissue disaggregation agent, may be directed through the first filter to remove at least a portion of and preferably substantially all of the collagen particles from the composition so that fewer, and preferably no, collagen particles are present in the filtered solution. The filtered regenerative cell composition containing the adipocytes and/or undigested tissue disaggregation agent, may then be directed through the second filter to remove at least a portion of and preferably substantially all of the free adipocytes from the filtered regenerative cell composition. Subsequently, the twice filtered regenerative cell composition, containing the undigested tissue disaggregation agent, may be directed through the third filter, such as a hollow fiber filtration device, as discussed herein, to remove or reduce the undigested tissue disaggregation agent from the regenerative cell composition.

The thrice-filtered regenerative cell composition (i.e., the composition remaining after being passed through the first, second, and third filters) may then be directed to multiple outlets, which may include a portion of the processing chamber 30 comprising multiple outlets. These outlets can serve to maintain the necessary pressure, as well as to provide connections via conduits to other containers which may include the collection chamber 20, the output chamber 50, and/or the waste container 40.

In one embodiment, a filter of the filter assembly 36 comprises a hollow-fiber filtration member. Or, in other words, the filter comprises a collection of hollow tubes formed with the filter media. Examples of filter media which can be used with the disclosed system 10 include polysulfone, polyethersulfone or a mixed ester material, and the like. These hollow fibers or hollow tubes of filter media may be contained in a cylindrical cartridge of the filter assembly 36. The individual tubes or fibers of filter media typically have an inside diameter which ranges from about 0.1 mm to about 1 mm with a preferred value being about 0.5 mm. The diameter and length of a suitable cylindrical cartridge will determine the number of individual tubes of filter media which can be placed inside the cartridge. One example of a suitable hollow fiber filter cartridge is the FiberFlo® Tangential Flow Filter, catalog #M-C-050-K(Minntech, Minneapolis, Minn.). Pore sizes of the filter media can range between about 10 kiloDaltons and about 5 microns with a preferred pore size being about 0.5 microns.

Figure 12A:
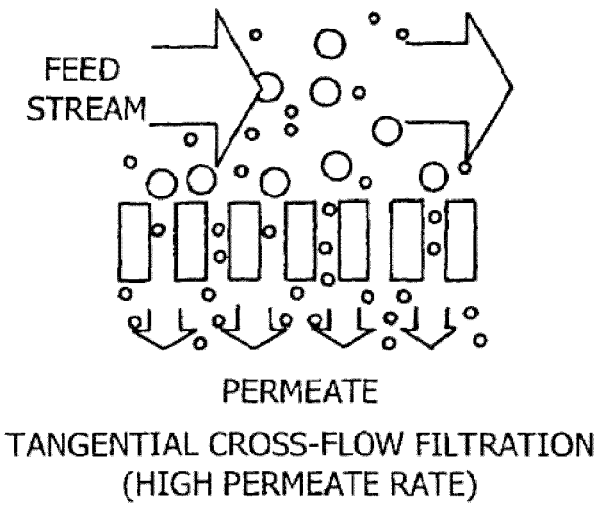
FIG. 12A illustrates a filtration process in which the feed stream of fluid flows tangentially to the pores of the filter.

In the hollow-fiber filter, each hollow tube has a body with a first end, a second end, and a lumen located in the body and extending between the first end and second end. The body of each hollow tube includes a plurality of pores. The pores are generally oriented in the body so that a regenerative cell composition is filtered by flowing through the lumen of the body, and the products to be filtered tangentially pass through the pores, as shown in FIG. 12A. In other words, the smaller particles in the liquid pass tangentially through the pores relative the flow of fluid through the lumen of the body. The composition with the regenerative cells passes through the lumen of each hollow tube when the composition is being filtered. Preferably, the flow of the composition is tangential to the pores of the body of each hollow tube.

Figure 12B:
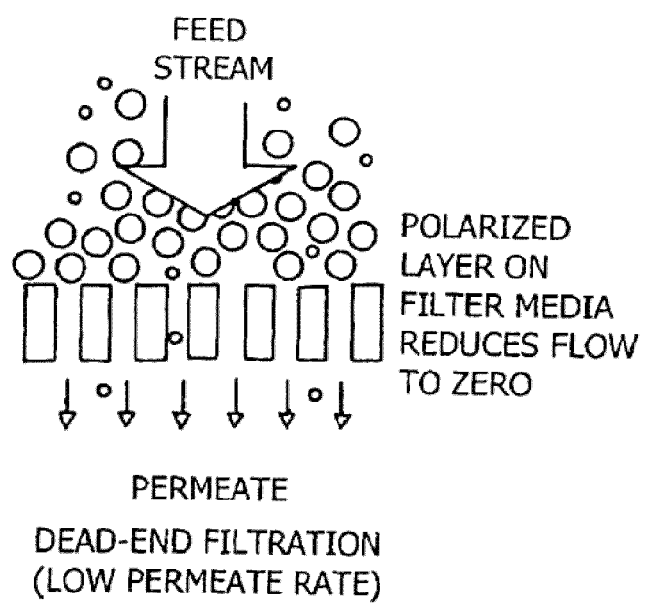
FIG. 12B illustrates a filtration process in which the feed stream of fluid flows perpendicular to the pores of the filter.

By using a tangential flow of fluid, the efficiency of filtration of the stem cells may be enhanced relative to other filtration techniques. For example, in accordance with some filtration techniques, the pores of the filter media are placed in such a manner that the filter is orientated perpendicular to the flow of the fluid so that the Filter media blocks the path of the fluid being filtered, as illustrated in FIG. 12B. In this type of filtration, the particles which are being filtered out of the regenerative cell composition, e.g., the stem cells, tend to build up on one side of the filter and block the flow of the fluid through the pores. This blockage can reduce the efficiency of the filter. In addition, the cells are constantly compressed by the pressure of the fluid flow as well as the weight of the cells accumulating on the upstream side of the filter. This can lead to increased lysis of stem cells. Thus, in such filtration techniques wherein the flow of fluid is parallel to the orientation of the pores in the filter, both large cells and small particles can be undesirably directed against the filter media as the fluid is passed through the pores. Consequently, larger products in the liquid such as cells may block the pores, thereby decreasing the filtering effect and increasing an occurrence of cell rupture or injury.

In contrast, in the hollow fiber configuration of the present system 10, the fluid which is being filtered flows inside the lumen of the hollow tube. The portion of the fluid which has the ability to pass through the pores of the body of the filter does so with the aid of the positive pressure of the fluid on the inside of the body as well as a negative pressure which is applied on the outside of the body. In this embodiment, the cells typically are not subjected to the pressure of the fluid flow or the weight of other cells, and therefore, the shear forces on the stem cells are reduced Thus, the efficiency and effectiveness of the filtration can be enhanced by the reduction in clogging rates and the reduction in regenerative cell lysis. Due to the size of the saline and unwanted protein molecules, during filtration, these molecules and other small components pass through the pores of the bodies of the hollow tubes to the outside of the hollow tubes and are directed to the waste container 40. In one embodiment, filtration is enhanced by generating a vacuum on the outside of the hollow tube filter media. Due to the size of the regenerative cells, e.g., stem cells or progenitor cells, these cells typically cannot pass through the pores of the body and therefore remain on the inside of the hollow tube filter (e.g., in the lumens of the tubes) and are directed back to the processing chamber 30 via a conduit between the filter and the processing chamber, or to the output chamber 50.

In one specific embodiment, the hollow fiber filter has about a 0.05 micron pore size, and contains approximately 550 cm$^2$ surface area of filter media. An individual media tube typically has a diameter of about 0.5 mm. In processing 130 ml of the regenerative cell composition, approximately 120 ml of additional saline may be added to the composition. The processing or filter time may be approximately 8 minutes. The differential of the pressures on either side of the body of the hollow fiber tube (e.g., the pressure inside the lumen of the body, and outside the body) is considered the trans-membrane pressure. The trans-membrane pressure can range from about 1 mmHg to about 500 mmHg with a preferred pressure being about 200 mmHg. The average nucleated cell recovery and viability using hollow fiber filtration can be approximately 80% of viable cells.

The amount of collagenase which is typically removed in such a system equates to a three log reduction. For example if the initial concentration of collagenase in the regenerative cell composition which is transferred from the collection chamber to the processing chamber is 0.078 U/ml the collagenase concentration of the final regenerative cell composition would be 0.00078 U/ml. The collagenase is removed in the hollow fiber filter, and the hollow fiber filter corresponds to the third filter discussed above.

Processing chambers illustrating one or more cell filtration methods described above are shown in the Figures, particularly FIGS. 1-3. With reference to FIGS. 1-3, between the processing chamber 30 and the filtering chamber of the filter assembly 36, a pump may be provided, such as pump 34. In addition, vent and pressure sensors, such as vent 32, and pressure sensor 39, may be provided in line with the processing chamber 30 and the filter assembly 36. Fittings for the output chamber 50 may also be provided. These optional components (e.g., the pump 34, the vent 32, the pressure sensor 39, and the fittings for the output chamber 50) may be provided between the processing chamber 30 and the filter assembly 36 so that liquid contained in the processing chamber 30 may flow to one or more of these optional components before flowing through the filter assembly 36. For example, liquid may flow through the pump 34 before it is passed to the filter assembly 36. Or, liquid may pass through the pressure sensor 39 before passing through the filter assembly to obtain a pre-filter liquid pressure in the system. In certain situations, one or more of these components may also be provided as an element of the processing chamber 30, such as the vent 32 as illustrated in FIG. 6. In the illustrated embodiment, the pressure sensor 39 is in line to determine the pressure of the regenerative cell composition which is generated by the pump 34 as it enters the filtering chamber of the filter assembly 36. This construction can facilitate monitoring of the trans-membrane pressure across the filter membrane. Additional saline or other buffer and washing solution can be added to the regenerative cell composition to assist in the removal of unwanted proteins as the composition is being filtered through the filter assembly 36. This repeated washing can be performed multiple times to enhance the purity of the regenerative cells. In certain embodiments, the saline can be added at any step as deemed necessary to enhance filtration.

In one specific embodiment, which is provided by way of example and not limitation, the unwanted proteins and saline or other washing solution is removed in the following manner. The composition with the regenerative cells, as well as collagen and connective tissue particles or fragments, adipocytes, and collagenase, is cycled through a series of filters until a minimum volume is reached. The minimum volume is a function of the total hold up volume of the system and some predetermined constant. The hold up volume is the volume of liquid which is contained in the tubing and conduits if all of the processing chambers are empty. In one embodiment, the minimum volume is 15 ml. When the minimum volume is reached, a predetermined volume of washing solution is introduced into the system to be mixed with the regenerative cell composition. This mixture of washing solution and the regenerative cell composition is then cycled through the filters until the minimum volume is reached again. This cycle can be repeated multiple times to enhance the purity of the regenerative cells, or in other words, to increase the ratio of regenerative cells in the composition to the other materials in the composition. See FIGS. 10 and 11.

After it has been determined that the regenerative cell composition has been cleansed of unwanted proteins and concentrated sufficiently (in exemplary embodiments, minimum concentrations within a range of about $1 \times 10^5$ to about $1 \times 10^7$ cells/ml can be used and, in a preferred embodiment the minimum concentration can be about $1 \times 10^7$ cells/ml), an output chamber 50, such as an output bag, may be connected to an outlet port of the processing chamber 30 and/or the filter assembly 36, depending on the specific embodiment. A vent, such as the vent 32, may then be opened to facilitate the output of the concentrated regenerative cells. In one implementation, this determination of when a minimum concentration has been reached is made empirically after experiments have been run and programmed into the electronic controls of the device. The determination can be an input into the process of what is desired to yield, i.e., how many stem/progenitor cells are desired, or range of cell concentration. Based on scientific data, a predefined amount of adipose tissue needs to be obtained and placed into the system to achieve the desired output. With the vent 32 open, a pump, such as the pump 34, can function to transfer the concentrated regenerative cells into the output bag. In one embodiment, the output bag 50 is similar to an empty blood bag which has a tube with a fitting on one end. In a sterile fashion, the fitting on the output bag may be attached to the outlet port, and the concentrated regenerative cells may be transferred to the output bag.

As illustrated in FIGS. 1-3, a vacuum pump 26 may be provided in the system 10 to change the pressure in the system, among other things. For example, the vacuum pump 26 may be coupled to the collection chamber 20 via a conduit, such as conduit 12b, to cause a decrease in pressure within the collection chamber 20. Vacuum pump 26 may also be coupled to the processing chamber 30 by way of a conduit, such as conduit 12g. Regarding the operation of vacuum pump 26 in connection with pump 34, two separate vacuum pumps or sources may be implemented, or a single one may be implemented by using valves which direct the vacuum pull to the different conduits that need it at specific points in the process. In addition, vacuum pump 26 may be coupled to the waste container 40 via a conduit, such as conduit 12f.

Figure 10:
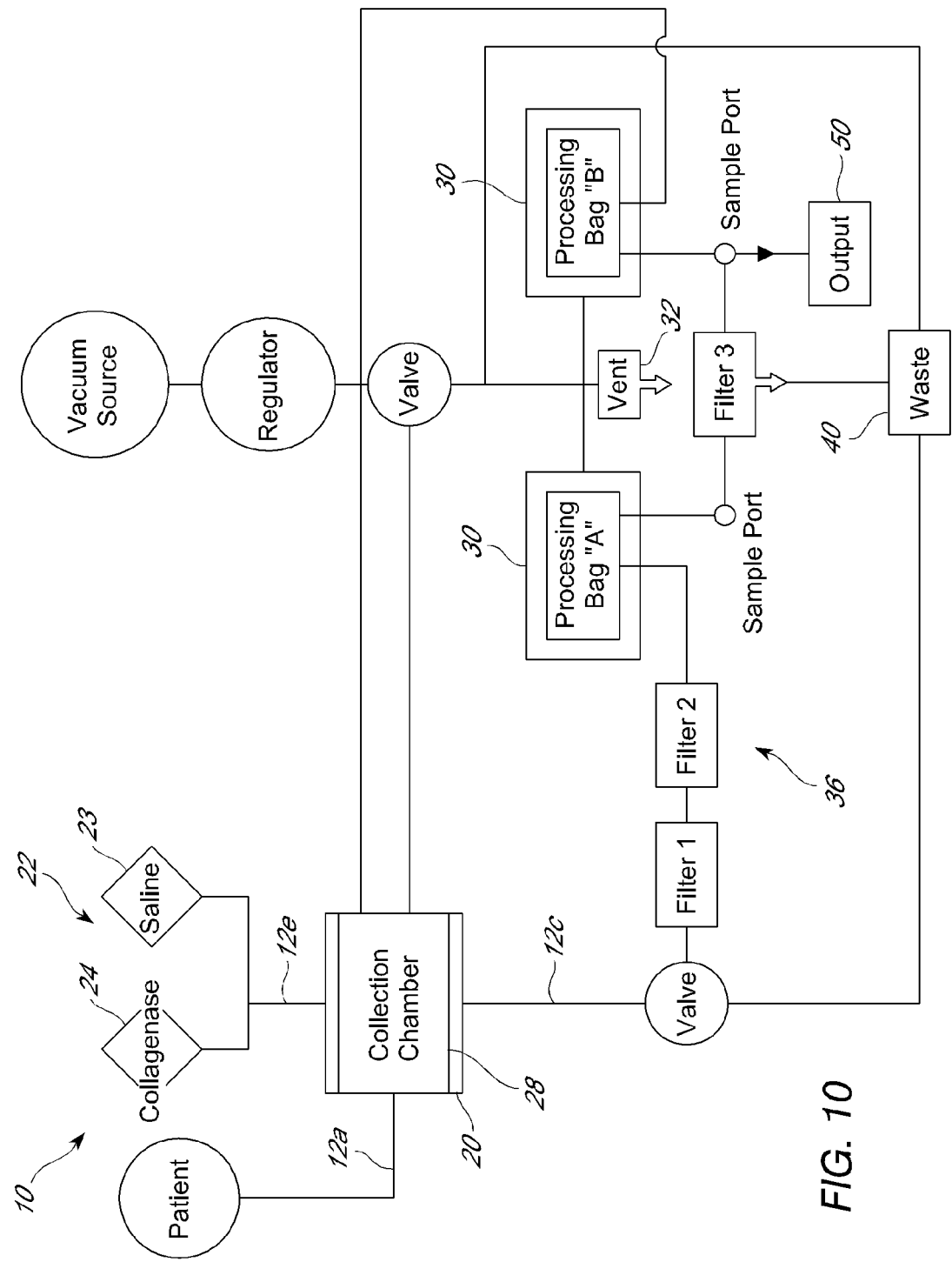
FIG. 10 is an illustration of a system for separating regenerative cells from tissue utilizing vacuum pressure to move fluids through the system. A vacuum system can be constructed by applying a vacuum pump or vacuum source to the outlet of the system, controlled at a predetermined rate to pull tissue and fluid through, using a system of stopcocks, vents, and clamps to control the direction and timing of the flow.
Figure 11:
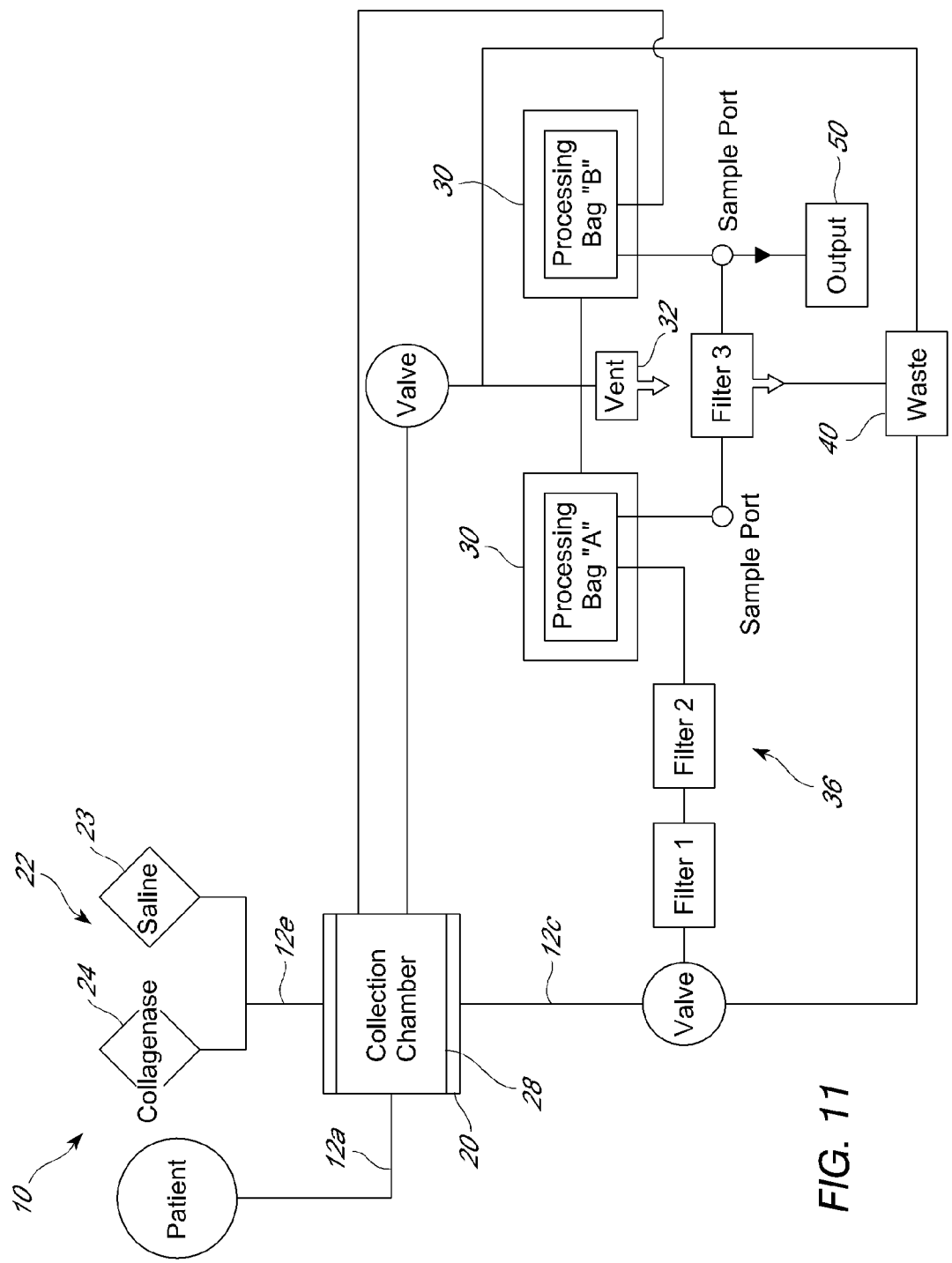
FIG. 11 is an illustration of a system for separating regenerative cells from tissue utilizing positive pressure to move fluids through the system. A positive pressure system uses a mechanical means such as a peristaltic pump to push or propel the fluid and tissue through the system at a determined rate, using valves, stopcocks, vents, and clamps to control the direction and timing of the flow.

With reference to FIGS. 10 and 11, the pressure generated by the vacuum pump 26 can be used to direct the flow of fluids, including the regenerative cells, through the conduits 12. This pressure can be supplied in multiple directions, for example, by automatically or manually controlling the position of one or more valves 14 in the system 10. The system 10 can be made to function properly with the use of positive pressure or through the use of negative pressure, or combinations thereof. For instance, the regenerative cells can be pulled through the first and second filters described above into a soft sided container which is connected to the third filter. The soft-sided container can be in line (serial) connected ahead of the third filter. The final output chamber may be a soft sided container which is on the other side (e.g., the downstream side) of the third filter. In this embodiment, pressure is used to move the regenerative cells from one soft sided container to a second soft sided container through the filter.

In another embodiment of the system 10, the filtration of the stem cells and/or adipose derived progenitor cells may be accomplished using a combination of percolative filtration and sedimentation. For example, such a system uses saline that is passed through a tissue regenerative cell composition (e.g., the composition containing the stem cells and/or adipose derived progenitor cells) and then through a filter. Some of the variables which are associated with percolative filtration of cells from a regenerative cell composition include, but are not limited to, pore size of the filter media, pore geometry or shape, surface area of the filter, flow direction of the regenerative cell composition being filtered, flow rate of the infused saline, trans-membrane pressure, dilution of the cell population, cell size and viability.

In one embodiment of the system 10, the processing chamber 30 uses a filter assembly 36 which implements percolative filtration and sedimentation to separate and concentrate the regenerative cells. By way of example, and not by way of limitation, the processing chamber 30 is defined as a generally cylindrical body having a sidewall 30a, a top surface 30b, and a bottom surface 30c, as shown in FIG. 6. A sterile vent 32 is provided in the top surface 30b.

In the embodiment of FIG. 6, the processing chamber 30 is illustrated as including a filter assembly 36, which includes two filters, such as large pore filter 36a, and small pore filter 36b. The pore sizes of the filters 36a and 36b typically are in a range between about 0.05 microns and about 10 microns. The large pore filter 36a may comprise pores with a diameter of about 5 µm, and the small pore filter 36b may comprise pores with a diameter of about 1-3 µm. In one embodiment, the filters have a surface area of about 785 mm². Filters 36a and 36b divide an interior of the processing chamber 30 to include a first chamber 37a, a second chamber 37b, and a third chamber 37c. As shown in FIG. 6, first chamber 37a is located between second chamber 37b and third chamber 37c. In addition, first chamber 37a is shown as being the region of the processing chamber 30 having an inlet port 31a and an outlet port 31b. The illustrated processing chamber 30 includes a plurality of ports providing communication paths from an exterior of the processing chamber 30 to the interior of the processing chamber 30, such as ports 31a, 31b, and 31c. The ports 31a, 31b, and 31c, are illustrated as being disposed in the sidewall 30a of a body of the processing chamber 30. However, the ports 31a, 31b, and 31c could be positioned in other regions, as well. Port 31a is illustrated as a sample inlet port, which is constructed to be coupled to a conduit so that a composition containing regenerative cells can be passed into the interior of the processing chamber 30. Port 31b is illustrated as an outlet port constructed to be coupled to a conduit so that the separated and concentrated cells may be removed from the interior of the processing chamber 30. Port 31c is illustrated as an inlet port constructed to be coupled to a conduit for delivery of a fresh washing solution, such as saline into the interior of the processing chamber 30.

In use, the regenerative cells may be introduced into the central chamber 37a via inlet port 31a. Saline or other buffer is introduced into the bottom chamber 37b through inlet port 31c. The saline may be directed through the regenerative cell composition in chamber 37a at a rate of about 10 ml/min. The flow rate of the saline is such that it counteracts the force of gravity. The flow of saline gives the cells in the chamber the ability to separate based on the density of the cells.

Typically, as the saline is forced up through the composition the larger cells in the composition will settle to the bottom of the central chamber 37a, and the smaller cells and proteins will be carried away through the second filter 36b into the top chamber 37c. This filtering is accomplished by adjusting the flow rate of the saline such that the larger cells are rolled in place which allows the smaller particles to be liberated and carried off with the saline. The sterile vent 32 is included in the chamber 30 to ensure that the correct pressure gradient is maintained in the three chambers within the processing unit. The upper chamber 37c can comprise an absorbent media 33. The purpose of the absorbent media is to trap the unwanted proteins in the solution to ensure that they do not cross the filter media back into the processing solution, if, for example, the saline flow rate decreases. An absorbent media can be a type of filter material that is absorbent, or attracts materials or components to be filtered out. An outflow port can be added above the top filter to help draw off the waste. Another embodiment of this may be to apply a gentle vacuum from the top to help pull off waste. Absorbent media can be implemented when, as in the illustrated embodiment, the flow rates are relatively small. Excess saline and proteins are then carried away to a waste container.

When the larger cells, (e.g., the adipose derived stem cells and/or progenitor cells) have been sufficiently separated from smaller cells and proteins, the composition containing the separated cells may be concentrated, as discussed herein. The composition may be further concentrated after it has been removed from chamber 37a through outlet port 31b, or while it is in the chamber 37a. In one embodiment, the concentration of cells in the composition is increased in the following manner. After the cells have been sufficiently separated the filters, such as filters 36a and 36b, may be moved towards each other. This movement has the effect of reducing the volume between the two filters (e.g., the volume of chamber 37a). A vibrating member may also be provided in connection with the processing chamber 30 to facilitate concentrating of the cells in the composition. In one embodiment, the vibrating member may be coupled to the filter 36b (e.g., the small pore filter). Vibrating can reduce an incidence of cells becoming trapped in the filters. The reduction in volume of the composition allows the excess saline to be removed as waste and the cells to be concentrated in a smaller volume.

In another embodiment, the concentration of the regenerative cells is accomplished in the following manner. After the cells have been sufficiently separated, the regenerative cell composition can be transferred to another chamber (not shown) which uses gravity to filter out the excess saline. In a preferred embodiment, the sedimentation can occur at the same time as the percolation. This sedimentation may be accomplished by introducing the composition on top of a filter which has a pore size ranging from about 10 kD to about 2 microns. In one embodiment, a suitable filter has a pore size of about 1 micron. The force of gravity will allow the saline and smaller particles to be passed through the filter while preventing the cells in the composition to flow through the filter. After the desired concentration of cells has been obtained, and after the filtered smaller particles have been removed from below the filter, the regenerative cell composition may be agitated to remove the cells from the filter and, subsequently, the concentrated regenerative cells may be transferred to the output bag. The smaller particles can be drawn off as waste through an outlet.

Figure 7:
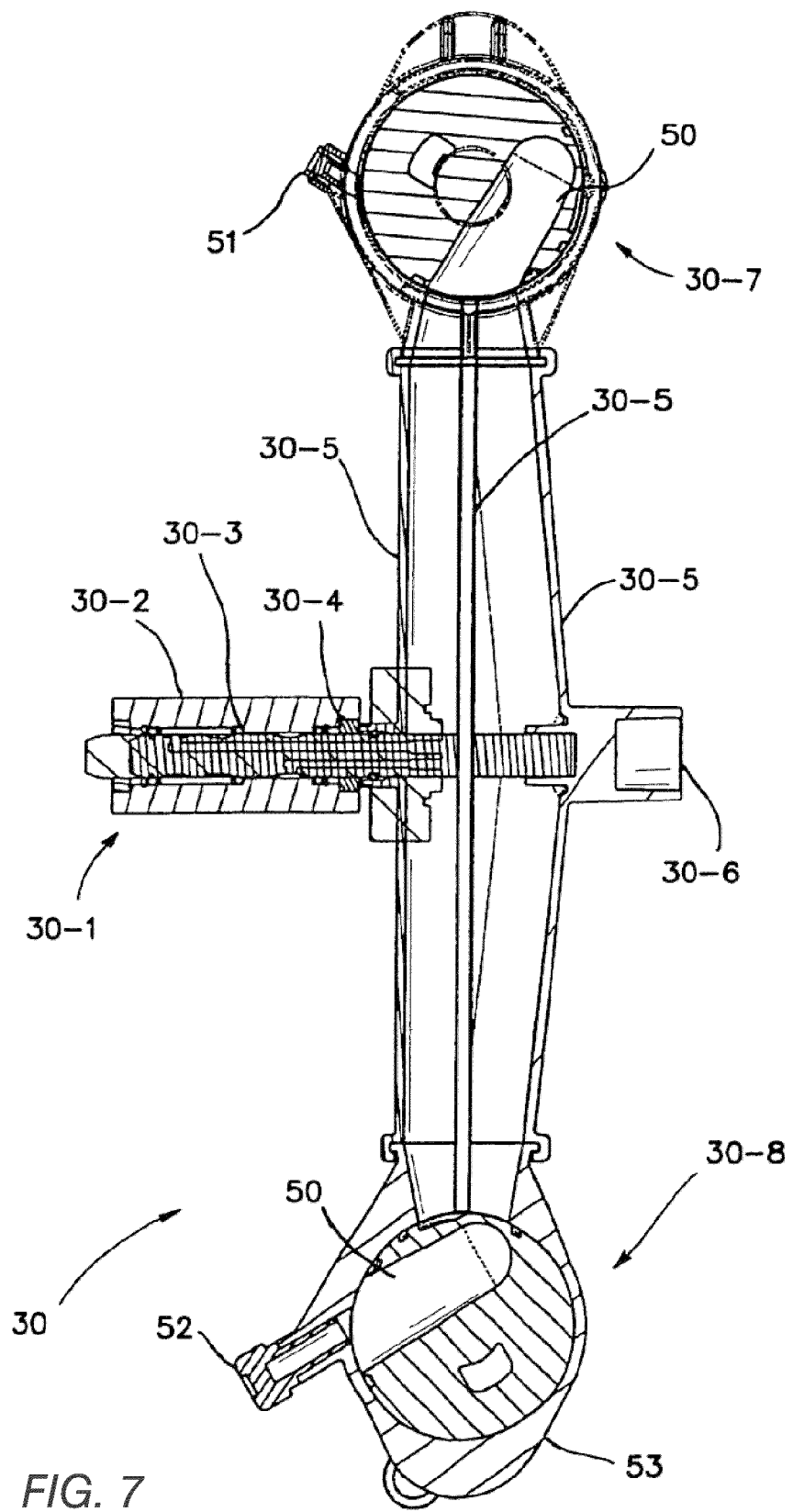
FIG. 7 is a sectional view of a processing chamber of a system for separating regenerative cells utilizing a centrifuge device for concentrating the regenerative cells.
Figure 8:
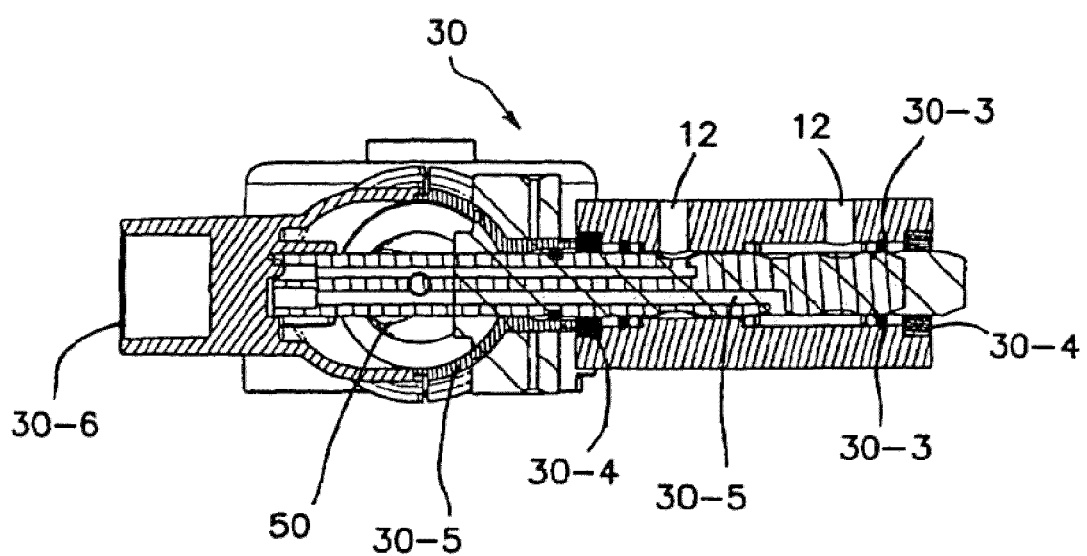
FIG. 8 is another sectional view of the processing chamber of FIG. 7.

In a particular embodiment, the regenerative cell composition from the collection chamber 20 is transported to the processing chamber 30 wherein the composition can be centrifuged to separate and concentrate regenerative cells. Centrifugation principles are well know in the art and will be not be repeated herein in the interest of brevity. Standard, art-recognized centrifugation devices, components and parameters are utilized herein. An exemplary processing chamber for use as part of a centrifuge device is shown in FIGS. 7 and 8. Typically, a centrifuge device causes a centrifuge chamber (such as the one shown in FIG. 7) to spin around an axis to thereby increasing the force on the cells in the solution to be greater than gravity. The denser or heavier materials in the solution typically settle to one end of the centrifuge chamber, i.e., an output chamber 50 of FIG. 7, to form a regenerative cell pellet. The pellet may then be re-suspended to obtain a solution with a desired concentration of cells and/or a desired volume of cells and medium. The processing chamber shown in FIG. 7 is constructed to separate and concentrate cells using both centrifugal and gravitational forces. Specifically, during centrifugation, centrifugal force directs the denser components of the regenerative cell composition, e.g., the regenerative cells, towards the outermost ends of the centrifuge chamber. As the centrifuge chamber slows down and eventually stops, gravitational force helps the regenerative cells to remain in the outermost ends of the centrifuge chamber and form a cell pellet. Accordingly, the unwanted components of the regenerative cell composition, i.e., the waste, can be removed without disturbing the cell pellet.

In yet another embodiment of the invention, the processing chamber may be comprised of a cell concentrator in the form of a spinning membrane filter. In a further embodiment of the centrifugation process, centrifugal elutriation may also be applied. In this embodiment, the cells may be separated based on the individual cell sedimentation rate such that the directional (e.g., outward) force applied by centrifugation causes cells and solutes to sediment at different rates. In elutriation, the sedimentation rate of the target cell population is opposed by an opposite (e.g., inward) flow rate applied by pumping solution in the opposite direction to the centrifugal force. The counterflow is adjusted so that the cells and particles within the solution are separated. Elutriation has been applied in many instances of cell separation (Inoue, Carsten et al. 1981; Hayner, Braun et al. 1984; Noga 1999) and the principles and practices used to optimize flow and centrifugal parameters can be applied herein in light of the present disclosure by one skilled in the art.

Figure 9:
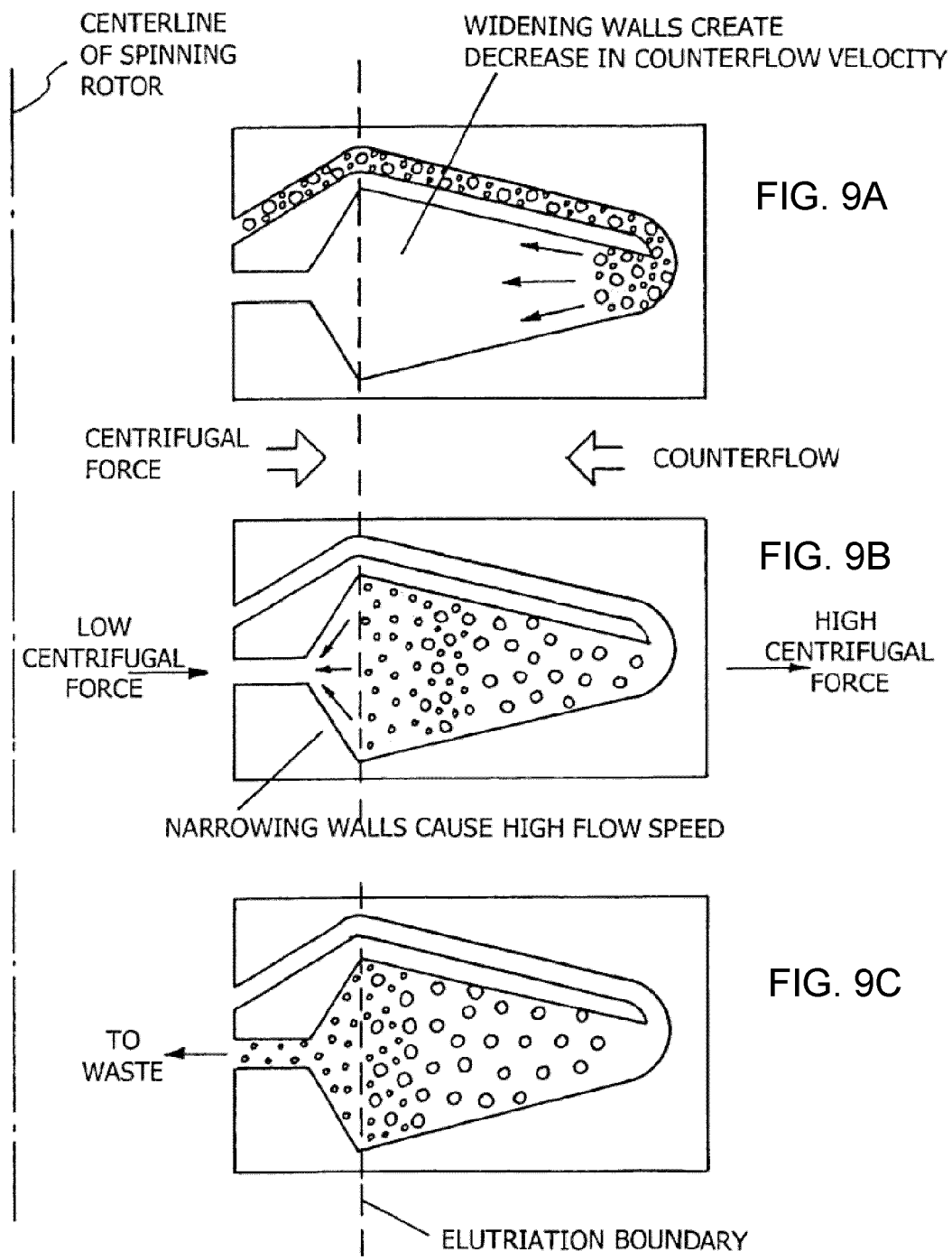
FIGS. 9A, 9B and 9C illustrate an elutriation component in use with the system of the invention.

FIG. 9 illustrates principles associated with an elutriation implementation in accordance with the present invention. The elutriation embodiment can be similar to a centrifugation implementation to the extent that a force is applied to the solution using a spinning rotor. Some of the variables which are associated with the presently embodied elutriation separation include, but are not limited to, the size and shape of the spinning chamber, the diameter of the rotor, the speed of the rotor, the diameter of the counter flow tubing, the flow rate of the counter flow, as well as the size and density of the particles and cells which are to be removed from solution. As in centrifugation, the regenerative cells can be separated based on individual cell densities.

In one embodiment the regenerative cell composition, e.g., the solution containing the regenerative cells and the collagenase, is introduced into a chamber of a spinning rotor, as shown in FIG. 9A. After the solution is added to the chamber additional saline is added to the chamber at a predetermined flow rate. The flow rate of the saline can be predetermined as a function of the speed of the rotor, the cell diameter, and the chamber constant which has been established empirically. The flow rate will be controlled for example with a device similar to an IV pump. A purpose of the additional saline is to provide a condition inside the rotor chamber where the larger particles will move to one side of the chamber and the smaller particles will move to the other, as illustrated in FIG. 9B. The flow is adjusted so that, in this application, the smaller particles will exit the chamber and move to a waste container, as shown in FIG. 9C. This movement results in the solution in the rotor chamber having a substantially homogenous population of cells, such as stem cells. After it has been determined that the stem cells have been separated from the rest of the items in the solution (with unwanted proteins and free lipids having been removed from the chamber), the counter flow is stopped. The cells inside the chamber will then form a concentrated pellet on the outside wall of the chamber. The counter flow is reversed and the cell pellet is transferred to the output bag.

As previously set forth herein, the processing chamber 30 or the output chamber 50 may include one or more ports, e.g., ports 51 or 52. One or more of these ports may be designed to transport the regenerative cells obtained using any combination of methods described above, or a portion thereof, via conduits to other surgical devices, cell culturing devices, cell marinading devices, gene therapy devices or purification devices. These ports may also be designed to transport the regenerative cells via conduits to additional chambers or containers within the system or as part of another system for the same purposes described above. The ports and conduits may be also be used to add one or more additives, e.g., growth factors, re-suspension fluids, cell culture reagents, cell expansion reagents, cell preservation reagents or cell modification reagents including agents that transfer genes to the cells. The ports and conduits may also be used to transport the regenerative cells to other targets such as implant materials (e.g., scaffolds or bone fragments) as well as other surgical implants and devices.

Further processing of the cells may also be initiated by reconfiguring the interconnections of the disposable sets of the existing system, re-programming the processing device of the existing system, by providing different or additional containers and/or chambers for the existing system, by transporting the cells to a one or more additional systems or devices and/or any combinations thereof. For example, the system can be reconfigured by any of the means described above such that the regenerative cells obtained using the system may be subject to one or more of the following: cell expansion (of one or more regenerative cell types) and cell maintenance (including cell sheet rinsing and media changing); sub-culturing; cell seeding; transient transfection (including seeding of transfected cells from bulk supply); harvesting (including enzymatic, non-enzymatic harvesting and harvesting by mechanical scraping); measuring cell viability; cell plating (e.g., on microtiter plates, including picking cells from individual wells for expansion, expansion of cells into fresh wells); high throughput screening; cell therapy applications; gene therapy applications; tissue engineering applications; therapeutic protein applications; viral vaccine applications; harvest of regenerative cells or supernatant for banking or screening, measurement of cell growth, lysis, inoculation, infection or induction; generation of cells lines (including hybridoma cells); culture of cells for permeability studies; cells for RNAi and viral resistance studies; cells for knock-out and transgenic animal studies; affinity purification studies; structural biology applications; assay development and protein engineering applications.

For example, if expansion of a regenerative cell population is required for a particular application, an approach using culture conditions to preferentially expand the population while other populations are either maintained (and thereby reduced by dilution with the growing selected cells) or lost due to absence of required growth conditions could be used. Sekiya et al have described conditions which might be employed in this regard for bone marrow-derived stem cells (Sekiya et al., 2002). This approach (with or without differential adherence to the tissue culture plastic) could be applied to a further embodiment of this invention. In this embodiment the final regenerative cell pellet is removed from the output chamber and placed into a second system providing the cell culture component. This could be in the form of a conventional laboratory tissue culture incubator or a Bioreactor-style device such as that described by Tsao et al., U.S. Pat. No. 6,001,642, or by Armstrong et al., U.S. Pat. No. 6,238,908. In an alternative embodiment, the cell expansion or cell culture component could be added to the existing system, e.g., into the output chamber, allowing for short-term adherence and/or cell culture of the adipose derived cell populations. This alternate embodiment would permit integration of the cell culture and/or cell expansion component to the system and remove the need for removing the cells from this system and placement within another.

During the processing, one or more additives may be added to or provided with the various chambers or containers as needed to enhance the results. These additives may also be provided as part of another system associated with the existing system or separate from the existing system. For example, in certain embodiments, the additives are added or provided without the need for removing the regenerative cells from the system. In other embodiments, the additives are added or provided by connecting a new container or chamber comprising the additives into an unused port of the system in a sterile manner. In yet other embodiments, the additives are added or provided in a second system or device that is not connected to the system of the present invention. Some examples of additives include agents that optimize washing and disaggregation, additives that enhance the viability of the active cell population during processing, anti-microbial agents (e.g., antibiotics), additives that lyse adipocytes and/or red blood cells, or additives that enrich for cell populations of interest (by differential adherence to solid phase moieties or to otherwise promote the substantial reduction or enrichment of cell populations) as described herein.

For example, to obtain a homogenous regenerative cell population, any suitable method for separating and concentrating the particular regenerative cell type may be employed, such as the use of cell-specific antibodies that recognize and bind antigens present on, for example, stem cells or progenitor cells, e.g., endothelial precursor cells. These include both positive selection (selecting the target cells), negative selection (selective removal of unwanted cells), or combinations thereof. Intracellular markers such as enzymes may also be used in selection using molecules which fluoresce when acted upon by specific enzymes. In addition, a solid phase material with adhesive properties selected to allow for differential adherence and/or elution of a particular population of regenerative cells within the final cell pellet could be inserted into the output chamber of the system.

An alternate embodiment of this differential adherence approach would include use of antibodies and/or combinations of antibodies recognizing surface molecules differentially expressed on target regenerative cells and unwanted cells. Selection on the basis of expression of specific cell surface markers (or combinations thereof) is another commonly applied technique in which antibodies are attached (directly or indirectly) to a solid phase support structure (Geiselhart et al., 1996; Formanek et al., 1998; Graepler et al., 1998; Kobari et al., 2001; Mohr et al., 2001).

In another embodiment the cell pellet could be re-suspended, layered over (or under) a fluid material formed into a continuous or discontinuous density gradient and placed in a centrifuge for separation of cell populations on the basis of cell density. In a similar embodiment continuous flow approaches such as apheresis (Smith, 1997), and elutriation (with or without counter-current) (Lasch et al., 2000) (Ito and Shinomiya, 2001) may also be employed.

Other examples of additives may include additional biological or structural components, such as cell differentiation factors, growth promoters, immunosuppressive agents, medical devices, or any combinations thereof, as discussed herein. For example, other cells, tissue, tissue fragments, growth factors such as VEGF and other known angiogenic or arteriogenic growth factors, biologically active or inert compounds, resorbable scaffolds, or other additives intended to enhance the delivery, efficacy, tolerability, or function of the population of regenerative cells may be added. The regenerative cell population may also be modified by insertion of DNA or by placement in a cell culture system (as described herein or known in the art) in such a way as to change, enhance, or supplement the function of the regenerative cells for derivation of a structural or therapeutic purpose. For example, gene transfer techniques for stem cells are known by persons of ordinary skill in the art, as disclosed in (Morizono et al., 2003; Mosca et al., 2000), and may include viral transfection techniques, and more specifically, adeno-associated virus gene transfer techniques, as disclosed in (Walther and Stein, 2000) and (Athanasopoulos et al., 2000). Non-viral based techniques may also be performed as disclosed in (Muramatsu et al., 1998). A gene encoding one or more cellular differentiating factors, e.g., a growth factor(s) or a cytokine(s), could also be added. Examples of various cell differentiation agents are disclosed in (Gimble et al., 1995; Lennon et al., 1995; Majumdar et al., 1998; Caplan and Goldberg, 1999; Ohgushi and Caplan, 1999; Pittenger et al., 1999; Caplan and Bruder, 2001; Fukuda, 2001; Worster et al., 2001; Zuk et al., 2001). Genes encoding anti-apoptotic factors or agents could also be added. Addition of the gene (or combination of genes) could be by any technology known in the art including but not limited to adenoviral transduction, "gene guns," liposome-mediated transduction, and retrovirus or lentivirus-mediated transduction, plasmid, adeno-associated virus. These regenerative cells could then be implanted along with a carrier material bearing gene delivery vehicle capable of releasing and/or presenting genes to the cells over time such that transduction can continue or be initiated in situ.

When the cells and/or tissue containing the cells are administered to a patient other than the patient from whom the cells and/or tissue were obtained, one or more immunosuppressive agents may be administered to the patient receiving the cells and/or tissue to reduce, and preferably prevent, rejection of the transplant. As used herein, the term "immunosuppressive drug or agent" is intended to include pharmaceutical agents which inhibit or interfere with normal immune function. Examples of immunosuppressive agents suitable with the methods disclosed herein include agents that inhibit T-cell/B-cell costimulation pathways, such as agents that interfere with the coupling of T-cells and B-cells via the CTLA4 and B7 pathways, as disclosed in U.S. patent Pub. No. 20020182211. A preferred immunosuppressive agent is cyclosporine A. Other examples include myophenylate mofetil, rapamicin, and anti-thymocyte globulin. In one embodiment, the immunosuppressive drug is administered with at least one other therapeutic agent. The immunosuppressive drug is administered in a formulation which is compatible with the route of administration and is administered to a subject at a dosage sufficient to achieve the desired therapeutic effect. In another embodiment, the immunosuppressive drug is administered transiently for a sufficient time to induce tolerance to the regenerative cells of the invention.

In these embodiments, the regenerative cells may be contacted, combined, mixed or added to the additives through any art recognized manner, including devices such as the agitation devices and associated methods described herein. For example, rocking, inversion, compression pulsed or moving rollers may be used.

In another aspect, the cell population could be placed into the recipient and surrounded by a resorbable plastic sheath or other materials and related components such as those manufactured by MacroPore Biosurgery, Inc. (see e.g., U.S. Pat. Nos. 6,269,716; 5,919,234; 6,673,362; 6,635,064; 6,653,146; 6,391,059; 6,343,531; 6,280,473).

In all of the foregoing embodiments, at least a portion of the separated and concentrated regenerative cells may be cryopreserved, as described in U.S. patent application Ser. No. 10/242,094, entitled PRESERVATION OF NON EMBRYONIC CELLS FROM NON HEMATOPOIETIC TISSUES, filed Sep. 12, 2002, which claims the benefit of U.S. Provisional Patent Application 60/322,070 filed Sep. 14, 2001, which is commonly assigned, and the contents of which in their entireties are expressly incorporated herein by reference.

At the end of processing, the regenerative cells may be manually retrieved from the output chamber. The cells may be loaded into a delivery device, such as a syringe, for placement into the recipient by either, subcutaneous, intramuscular, or other technique allowing delivery of the cells to the target site within the patient. In other words, cells may be placed into the patient by any means known to persons of ordinary skill in the art. Preferred embodiments include placement by needle or catheter, or by direct surgical implantation. In other embodiments, the cells may be automatically transported to an output chamber which may be in the form of a container, syringe or catheter etc., which may be used to place the cells in the patient. The container may also be used to store the cells for later use or for cryopreservation. All retrieval methods are performed in a sterile manner. In the embodiment of surgical implantation, the cells could be applied in association with additives such as a preformed matrix or scaffold as described herein.

In preferred embodiments of the invention (e.g., the embodiment shown in FIG. 4), the system is automated. In another embodiment, the system has both automated and manual components. The system may be comprised of one or more disposable components connected to or mounted on a re-usable hardware component or module. The automated systems of the invention provide screen displays (see FIG. 16) that prompt proper operation of the system. The automated systems may also provide a screen that provides status of the procedure and/or the step by step instructions as to the proper setup of the disposable components of the system. The screen may also indicate problems or failures in the system if they occur and provide "troubleshooting" guidance if appropriate. In one embodiment, the screen is a user interface screen that allows the user to input parameters into the system through, e.g., a touch screen.

The partial and fully automated systems may include a processing device (e.g., microprocessor or personal computer) and associated software programs that provide the control logic for the system to operate and to automate one or more steps of the process based on user input. In certain embodiments, one or more aspects of the system may be user-programmable via software residing in the processing device. The processing device may have one or more pre-programmed software programs in Read Only Memory (ROM). For example, the processing device may have pre-programmed software tailored for processing blood, another program for processing adipose tissue to obtain small volumes of regenerative cells and another program for processing adipose tissue to obtain larger volumes of regenerative cells. The processing device may also have pre-programmed software which provides the user with appropriate parameters to optimize the process based on the user's input of relevant information such as the amount of regenerative cells required, the type of tissue being processed, the type of post-processing manipulation required, the type of therapeutic application, etc.

The software may also allow automation of steps such as controlling the ingress and egress of fluids and tissues along particular tubing paths by controlling pumps and valves of the system; controlling the proper sequence and/or direction of activation; detecting blockages with pressure sensors; mixing mechanisms, measuring the amount of tissue and/or fluid to be moved along a particular pathway using volumetric mechanisms; maintaining temperatures of the various components using heat control devices; and integrating the separation and concentration process with timing and software mechanisms. The processing device can also control centrifuge speeds based on the tissue type being processed and/or the cell population or sub-population being harvested, and the types of procedures to be performed (e.g., tissue enhancement using adipose tissue augmented with regenerative cells, or processing of cells for bone repair applications using regenerative cell coated bone grafts). The processing device may also include standard parallel or serial ports or other means of communicating with other computers or networks. Accordingly, the processing device can be a stand alone unit or be associated one or more additional devices for the further processing methods described herein.

The software may allow for automated collection of "run data" including, for example, the lot numbers of disposable components, temperature and volume measurements, tissue volume and cell number parameters, dose of enzyme applied, incubation time, operator identity, date and time, patient identity, etc. In a preferred embodiment of the device a character recognition system, such as a bar code reading system would be integrated to permit data entry of these variables (for example disposable set lot number and expiration date, lot number and expiration date of the Collagenase, patient/sample identifiers, etc.) into the processing device as part of documentation of processing. This would reduce the opportunity for data entry errors. Such a bar code reading system could be easily incorporated into the processing device using a USB or other interface port and system known to the art. In this way the device would provide integrated control of the data entry and documentation of the process. A print-out report of these parameters would be part of the user-defined parameters of a programmed operation of the system. Naturally this would require integration of a printer component (hardware and driver) or printer driver in software plus an interface output connector for a printer (e.g., a USB port) in the hardware of the device.

In certain embodiments, the system is a fully automated system. For example, the user may initially select the amount of tissue to be processed, attach the system to the patient and the system may automatically aspirate the required tissue and separate and concentrate regenerative cells in an uninterrupted sequence without further user input. The user may also input the amount of regenerative cells required and allow the system to aspirate the requisite amount of tissue and process the tissue. A fully automated system also includes a system which is capable of being reconfigured based on a number of (e.g., two or more) user input parameters, e.g., number of wash cycles, speed of centrifugation etc. The system can also be run in semi-automatic mode during which the system goes through certain steps without user intervention but requires user intervention before certain processes can occur. In other embodiments, the system is a single integrated system that displays instructions to guide the user to perform predetermined operations at predetermined times. For example, the processing device may prompt users through the steps necessary for proper insertion of tubing, chambers and other components of the system. Accordingly, the user can ensure that the proper sequence of operations is being performed. Such a system can additionally require confirmation of each operational step by the user to prevent inadvertent activation or termination of steps in the process. In a further embodiment, the system may initiate automated testing to confirm correct insertion of tubing, chambers, absence of blockages etc. In yet another embodiment, the system of the present invention is capable of being programmed to perform multiple separation and concentration processes through automated control of tissue flow through the system. This feature may be important, for example, during surgery on a patient where tissue that would otherwise be lost is collected into the system, and regenerative cells from the tissue are separated and concentrated and returned to the patient.

Figure 13:
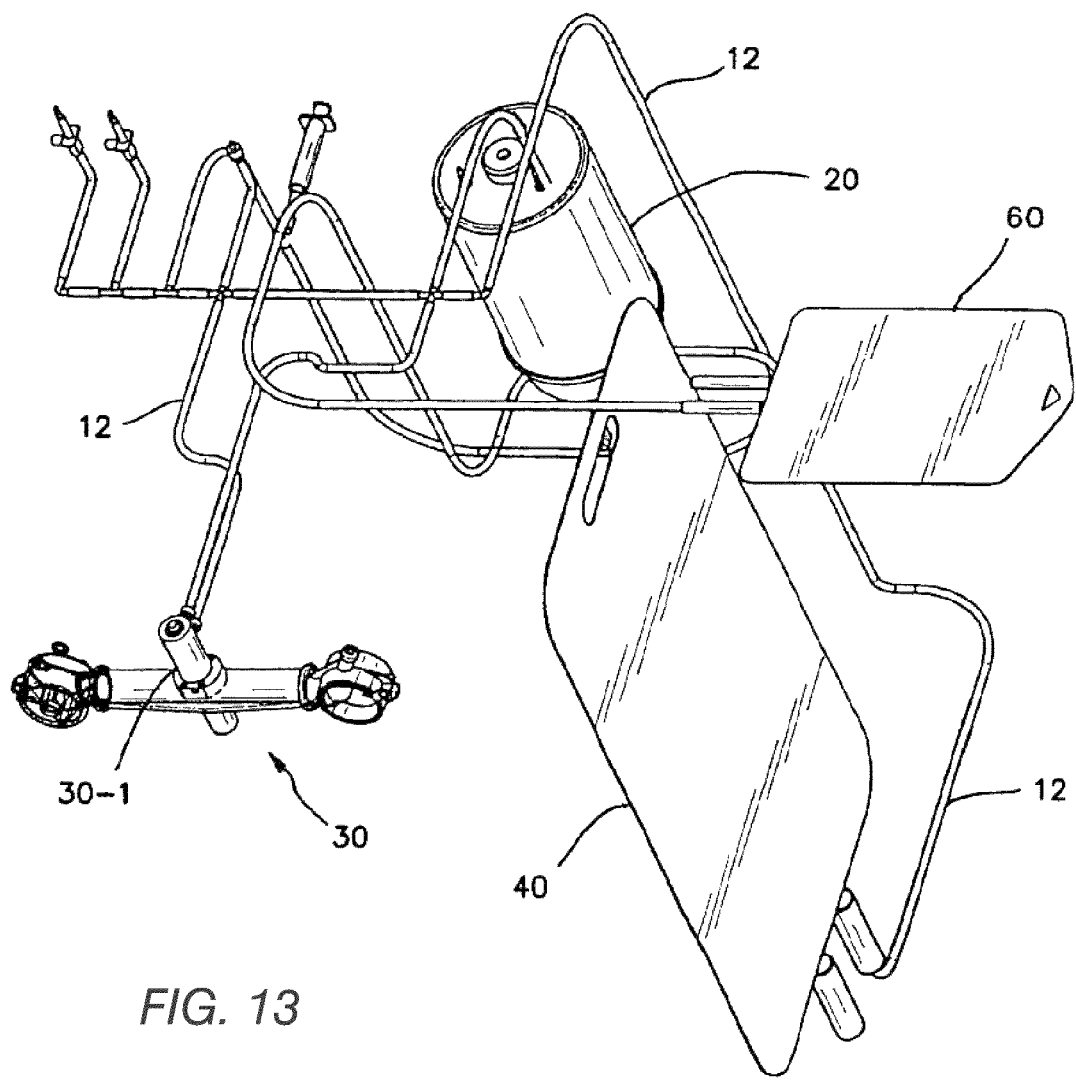
FIG. 13 is an illustration of an exemplary disposable set for a system of the invention.

As set forth above, components of the system may be disposable (referred to herein as "disposable set(s)"), such that portions of the system can be disposed of after a single use. This implementation can help ensure that any surface which comes in contact with the patient's tissue will be disposed of properly after being used. An exemplary disposable set is illustrated in FIG. 13. In a preferred embodiment, the disposable components of the system are pre-sterilized and packaged so as to be usable "off the shelf" that are easy to use and easy to load and that eliminate the need for many tubing connections and complex routing of tubing connections. Such disposable components are relatively inexpensive to manufacture, and therefore, do not create a substantial expense due to their disposal. In one embodiment, the disposable system (referred to interchangeably herein as "disposable set(s)") comprises, consists essentially of, or consists of, the collection chamber 20, the processing chamber 30, the waste chamber 40, the output chamber 50, the filter assemblies 36, the sample bag 60 and the associated conduits 12 or tubing. In preferred embodiments of the disposable sets of the system, the collection chamber 20 and the processing chamber 30 are connected by way of conduits 12 that are housed in a rigid frame. The rotating seal network (FIGS. 7 & 8) of a processing chamber 30 may also be housed in the same rigid frame. In another preferred embodiment, the various chambers and containers of the disposable set are comprised of the necessary interfaces that are capable of communicating with the processing device of the system such that the pumps, valves, sensors and other devices that automate the system are appropriately activated or de-activated as needed without user intervention. The interfaces also reduce the time and expertise required to set up the system and also reduce errors by indicating how to properly set up the system and alerting the user in the event of an erroneous setup.

Most of the disposable sets of the invention will have many common elements. However, the ordinarily skilled artisan will recognize that different applications of the system may require additional components which may be part of the disposable sets. Accordingly, the disposable sets may further comprise one or more needles or syringes suitable for obtaining adipose or other tissue from the patient and returning regenerative cells to the patient. The type number and variety of the needles and syringes included will depend on the type and amount of tissue being processed. The disposable sets may further comprise one or more rigid or flexible containers to hold washing fluids and other processing reagents used in the system. For example, the disposable sets may comprise containers to hold saline, enzymes and any other treatment or replacement fluids required for the procedure. In addition, suitable washing solutions, re-suspension fluids, additives, agents or trans-plant materials may be provided with the disposable sets for use in conjunction with the systems and methods of the invention.

Any combination of system components, equipment or supplies described herein or otherwise required to practice the invention may be provided in the form of a kit. For example, a kit of the invention may include, e.g., the optimal length and gage needle for the syringe based liposuction and sterile syringes which contain the preferred filter media which allows for the processing of small volumes of tissue. Other exemplary equipment and supplies which may be used with the invention and may also be included with the kits of the invention are listed in Tables II and III.

Table II below identifies examples of supplies that can be used in to obtain adipose derived regenerative cell in accordance with the systems and methods of the present invention:

TABLE II

| Description | Vendor | Quantity | Note |
| --- | --- | --- | --- |
| 10 ml syringe | Becton-Dickinson | as req'd | Optional, used for liposuction |
| 14 GA blunt tip needle | | as req'd | Optional, used for liposuction |
| Single Blood Pack (600 ml) | Baxter Fenwal | 1 | Main cell processing bag; bag has spike adaptor on line and two free spike ports |
| Transfer pack with coupler (150 ml) | Baxter Fenwal | 1 | Quad bag set |
| Transfer pack with coupler (1 L) | Baxter Fenwal | 1 | Waste bag |
| Sample Site Coupler | Baxter Fenwal | 2 | |
| 0.9% saline (for injection) | Baxter Fenwal | 1 | |
| 14 GA sharp needle | Monoject | as req'd | For adding liposuction tissue to bag |
| 20 GA sharp needle | Monoject | 3 | For adding collagenase and removing PLA cells |
| 0.2 µm Sterflip filter | Millipore | 1 | For filtering collagenase |
| Teruflex | Terumo | 4 | ME*ACS121 for |

TABLE II-continued

| Description | Vendor | Quantity | Note |
| --- | --- | --- | --- |
| Aluminium sealing clips | | | temporary tube sealing |
| Povidone Iodine prep pad | Triadine | as req'd | 10-3201 |
| Liberase H1 Collagenase | Roche | | See Procedure Note 1 |
| TSCD wafers | Terumo | 2 | 1SC*W017 for use with TSCD Sterile Tubing Welder |

Table III, below, identifies equipment that may be used with the systems and methods disclosed herein.

TABLE III

| Description | Vendor | Quantity | Note |
| --- | --- | --- | --- |
| Sorvall Legend T Easy Set Centrifuge | Fisher Scientific | 1 | 75-004-367 |
| Rotor | Kendro/Sorvall | 1 | TTH-750 rotor |
| Rotor buckets | Kendro/Sorvall | 4 | 75006441 round buckets |
| Adaptor for 150 ml bags | Kendro/Sorvall | 4 | 00511 |
| Plasma Expressor | Baxter Fenwal | 1 | 4R4414 |
| Tube Sealer | Sebra | 1 | Model 1060 |
| TSCD Sterile Tubing Welder | Terumo | 1 | 3ME*SC201AD |
| LabLine Thermal Rocker | LabLine | 1 | 4637 |
| 'Disposable' plastic hemostate-style clamp | Davron | 3 | |
| Balance Bags Sets | | 2 | Water-filled bags used to balance centrifuge |
| Biohazard Sharps Chamber | | 1 | |
| Biohazard Waste Chamber | | 1 | |

Figure 14B:
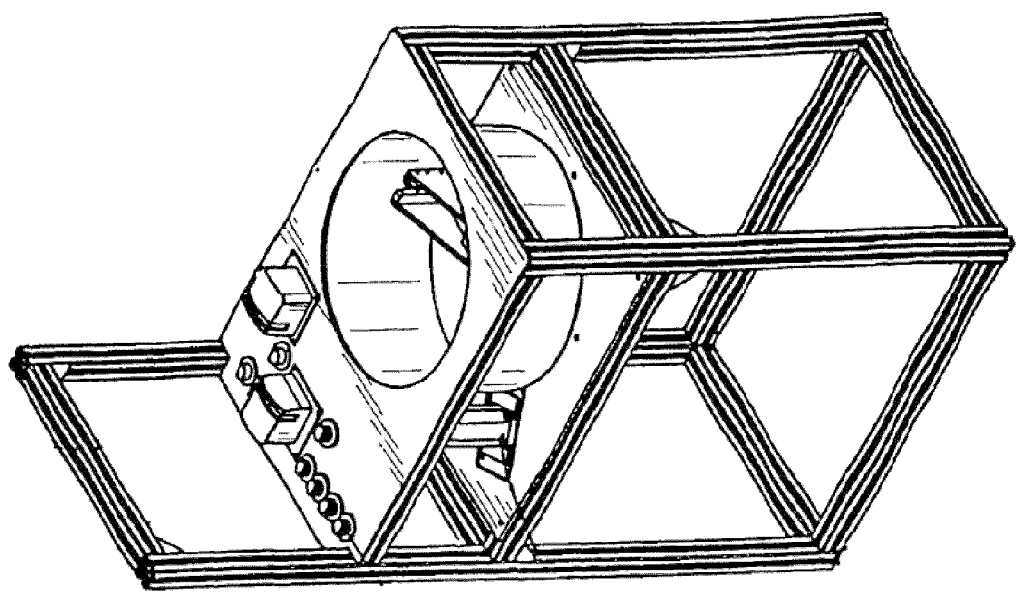
FIGS. 14A and 14B are front and back perspective views, respectively, of an exemplary re-usable component for a system of the invention.
Figure 14A:
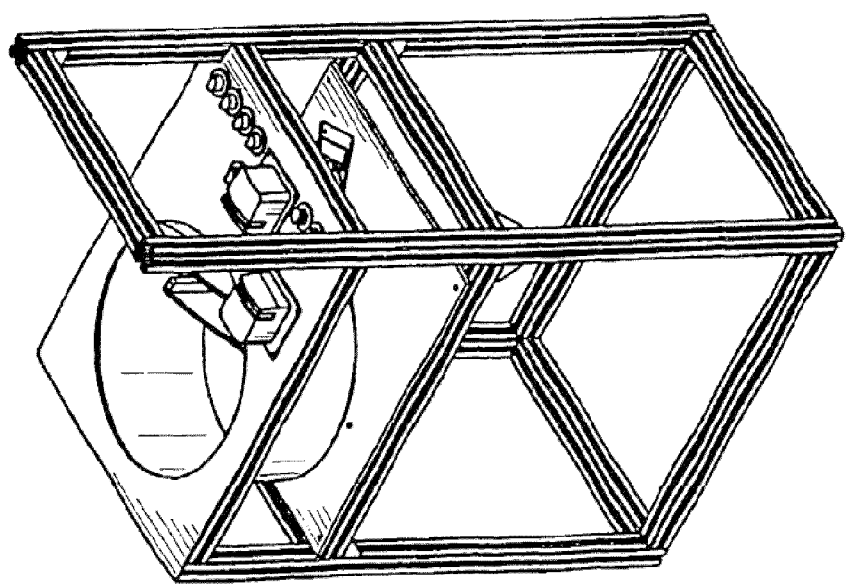
Figure 15B:
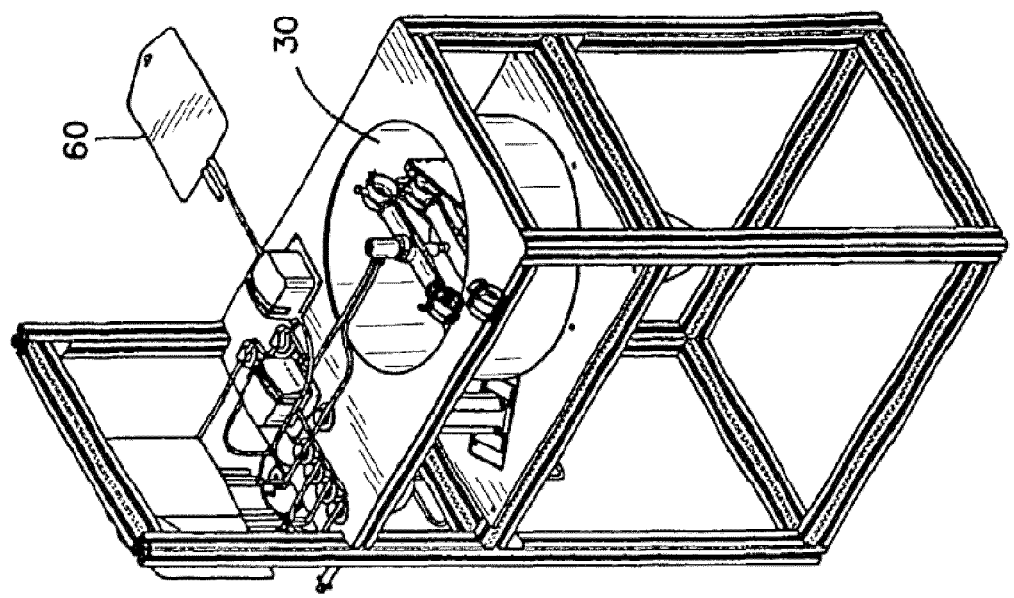
FIGS. 15A and 15B are front and back perspective views, respectively, of an exemplary device of the invention assembled using the disposable set of FIG. 13 and a re-usable component of FIGS. 14A and 14B.
Figure 15A:
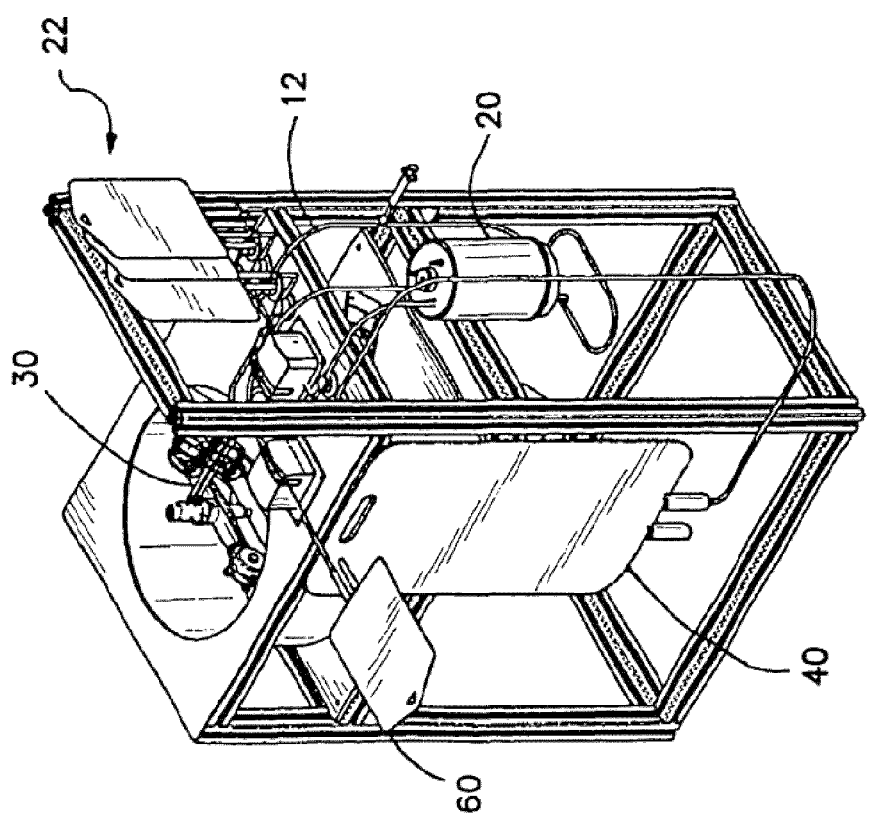
Figure 15C:
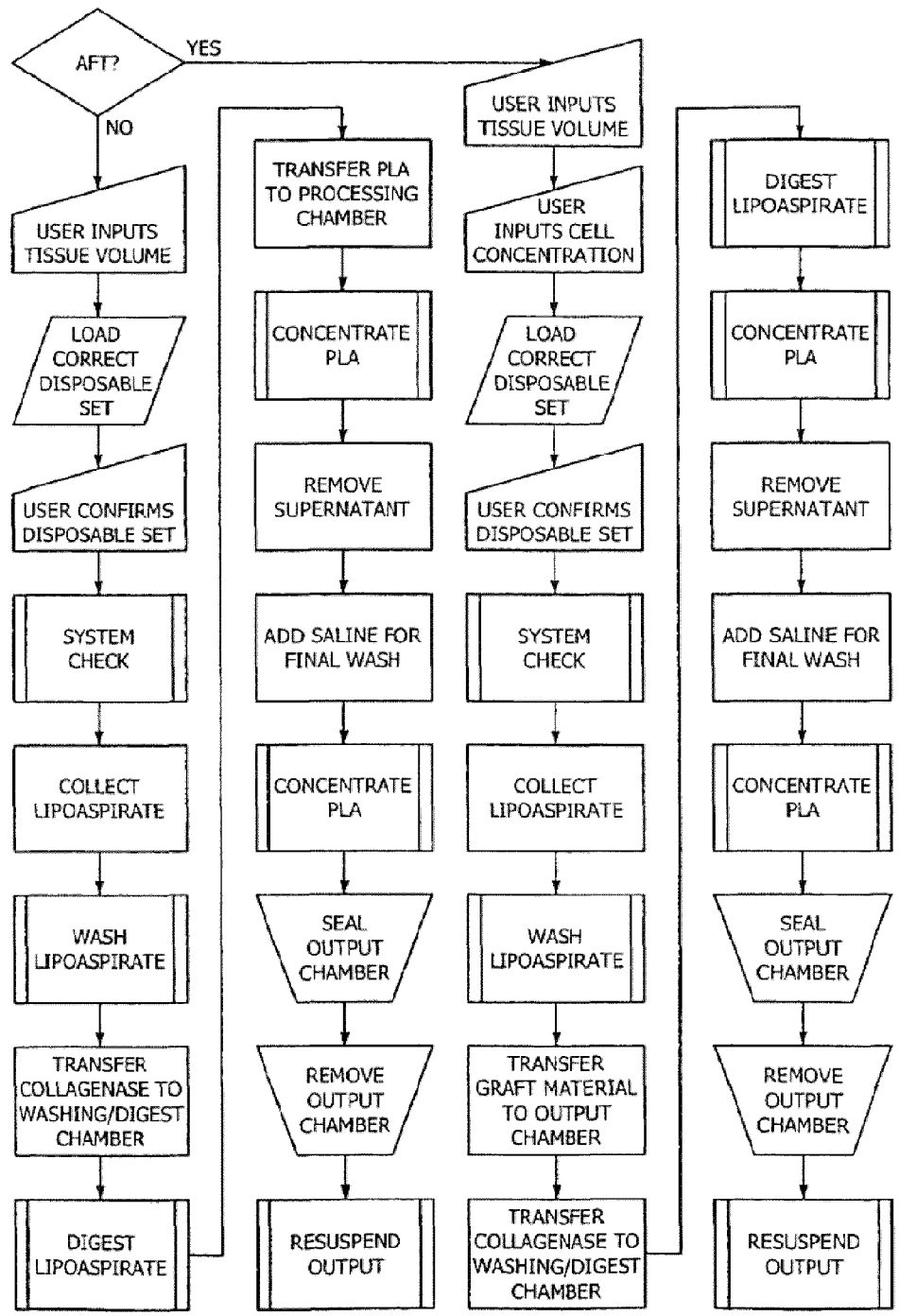
FIG. 15C is a flowchart depicting exemplary pre-programmed steps, implemented through a software program, that control automated embodiments of a system of the present invention. Two alternative processing parameters are shown indicating the versatility of the system.

The re-usable component of the system comprises, consists essentially of, or consists of the agitation mechanism for the collection chamber, the pump, and assorted sensors which activate valves and pump controls, the centrifuge motor, the rotating frame of the centrifuge motor, the user interface screen and USB ports, an interlocking or docking device or configuration to connect the disposable set such that the disposable set is securely attached to and interface with the re-usable hardware component and other associated devices. An exemplary re-usable component is illustrated in FIG. 14. In preferred embodiments, the re-usable component includes a means for separating and concentrating the regenerative cells from the regenerative cell composition, e.g., a rotating centrifuge. In this embodiment, the re-usable component is designed connect to and interface with a portion of the processing chamber (comprising a centrifuge chamber) of the disposable set as shown in FIG. 15A. It is understood that the means for separating and concentrating regenerative cells in the re-usable component is not limited to a rotating centrifuge but may also include any other configuration described herein, including a spinning membrane filter. The re-usable component may also house the processing device described herein which contains pre-programmed software for carrying out several different tissue processing procedures and selectively activating the various pumps and valves of the system accordingly. The processor may also include data storage capability for storing donor/patient information, processing or collection information and other data for later downloading or compilation. The re-usable component may be used with a variety of disposable sets. The disposable set is connected to the re-usable component through, e.g., an interlocking device or configuration to connect the disposable set such that the disposable set is securely attached to and interfaces with the re-usable hardware component in a manner that the processing device present on the re-usable component can control, i.e., send and receive signals to and from the various components of the disposable set as well as various components of the re-usable component and other associated devices and systems.

In one embodiment, a disposable set for use in the system is comprised of a collection chamber 20 which can accommodate about 800 mL of tissue; a processing chamber 30 which can process the regenerative cell composition generated by about 800 mL of tissue washed and digested in the collection chamber 20; an output chamber 50 which can accommodate at least 0.5 mL of regenerative cells; and a waster container 40 which can accommodate about 10 L of waste. In this embodiment, the hardware device is no larger than 24"L×18"W×36"H. Alternative dimensions of the various components of the disposable sets as well as the hardware device may be constructed as needed and are intended to be encompassed by the present invention without limitation.

The disposable components of the system are easy to place on the device. An illustration of a disposable set utilized assembled together with a corresponding re-usable component is illustrated in FIG. 15A. The system is preferably designed such that it can detect an improperly loaded disposable component. For example, the components of each disposable set may have color-guided marks to properly align and insert the tubing, chambers etc. into appropriate places in the system. In additional embodiments, the system disclosed herein is a portable unit. For example, the portable unit may be able to be moved from one location where adipose tissue harvesting has occurred, to another location for adipose tissue harvesting. In certain implementations, the portable unit is suitable for harvesting and processing of adipose tissue by a patient's bedside. Thus, a portable unit may be part of a system which can be moved from patient to patient. Accordingly, the portable unit may be on wheels which lock in place and, thus, can be easily placed and used in a convenient location in a stable and secure position throughout the procedure. In other embodiments, the portable unit is designed for set-up and operation on a flat surface such as a table top. The portable unit may also be enclosed in a housing unit. The portable unit may further be comprised of hangers, hooks, labels, scales and other devices to assist in the procedure. All of the herein described re-usable components of the system such as the centrifuge, processing device, display screen may be mounted on the portable unit of the system.

Alternate manual embodiments for obtaining regenerative cells are also within the scope of this invention. For example, in one embodiment, adipose tissue may be processed using any combination of the components of the system, equipment and/or supplies described herein.

A manual embodiment of the system of the invention may be practiced in accordance with the following steps and information, which are provided by way of example and not by way of limitation. First, adipose tissue is collected from a patient. A tissue retrieval line, or sampling site coupler, is opened and a spike is inserted into a side port of the 600 ml blood bag. Approximately 10 ml of adipose tissue is collected in a 10 ml syringe through the blunt cannula. The blunt cannula is replaced with a relatively sharp needle (14G). The sampling site is wiped with an iodine wipe. The adipose tissue is injected into the 600 ml bag through the sampling site. The syringe and needle are then discarded in a sharps chamber. These steps are repeated to place sufficient tissue into the bag. Sufficient tissue is determined on a case-by case basis based on the clinical specifics of the patient and application.

Second, the aspirated adipose tissue is washed. A pre-warmed (37° C.) saline bag is hooked above the work surface. A blue hempostat clamp is placed on the tubing between the 600 ml bag and the spike. The clamp is closed to seal the tubing. The spike on the 600 ml bag is used to enter the saline bag (in this setting use the needle on the 600 ml bag to enter the saline bag through the rubber septum, wipe the septum with iodine prior to insertion of needle). The blue clamp is released and approximately 150 ml of saline is allowed to enter the 600 ml bag. The blue clamp is closed when the desired volume of saline has entered the 600 ml bag. The 600 ml bag is inverted 10-15 times over approximately 15 seconds. A second blue clamp is applied to the tubing leading from the 3 L waste bag to the spike. The spike on the 3 L bag is used to enter the 600 ml bag. The 600 ml bag is hung inverted over the work surface, and is allowed to sit for approximately 1 minute. The blue clamp leading to the 3 L bag is released. Waste fluid is allowed to flow into the 3 L bag. The blue clamp is applied to stop the flow before tissue enters the tubing. The 600 ml bag is lowered to the work surface. These steps are repeated two more times. If the saline waste still appears noticeably red, a third additional cycle is indicated. A heat sealer is used to seal the tubing between the 3 L waste bag and the 600 ml bag. The seal is made at approximately the half way point on the tubing. The 3 L waste bag is removed and discarded. The 600 ml bag is returned to the work surface.

Third, the washed adipose tissue is digested. The blue clamp on the tubing between the saline and the 600 ml bag is released to allow approximately 150 ml of saline to enter the 600 ml bag. The sampling site on the 600 ml bag is wiped with an iodine wipe. Collagenase is injected through the sampling site to the 600 ml bag. The collagenase is prepared by thawing one collagenase vial in a 37° C. water bath or equivalent, other than microwaving. A 1 ml syringe with a 22 G needle is inserted into the vial. The collagenase is withdrawn into the needle. The needle is removed and replaced with a 0.2 µm filter and second 22 G needle. The collagenase is then expelled from the syringe through the 0.2 µm filter and needle. Digestion of the adipose tissue is performed at a final collagenase concentration of 0.1-0.2 Wunsch units/ml. The heating pad is placed on the rocker. During this time, the saline bag, while still attached, is set to the side of the rocker. Care is taken to ensure that the tubing leading to the saline bag is positioned in such a way that it does not get caught on the rocker when in motion. The heating pad controller is set to 37° C. The 600 ml bag is placed on the rocker. The rocker is set to maximum. The bag is observed to ensure that it is stable, and is allowed to rock for approximately 1 hour (55±10 mins).

Fourth, the regenerative cell composition is retrieved. The bag is removed from the rocker. A blue clamp is applied to the closed tubing formerly leading to the waste bag. The sterile connecting device is used to attach the quad bag set (pre-prepared according to the following instructions) to the tubing that was formerly attached to the waste bag. The quad pack can be seen as two linked quad packs. Identify the tubing splitting it into two packs, fold the tubing back on itself, and slip a metal loop over the folded tubing (over both pieces of tubing). Slide the loop down approx 0.5 inch. The crimp formed at the bend acts to seal the tubing. Use a hemostat to partially crimp the loop closed. The loop is not crimped too tightly because the loop will need to be removed during processing. The 600 ml bag is hung inverted over the work surface and is allowed to sit for approximately 3 minutes. The blue clamp on tubing leading to the quad set is released to drain the cell fraction (the layer under the yellow/orange fat layer) into the quad set. Care is taken to prevent the fat layer to enter the tubing. During this process, the tubing can be crimped manually to slow the flow as the fat layer gets close to the tubing. The tubing leading to the quad bag set is then closed with a blue clamp, the 600 ml bag is returned to the work surface, and the saline bag is hung. The blue clamp on the tubing between the saline and the 600 ml bag is released to allow approximately 150 ml of saline to enter the 600 ml bag. The 600 ml bag is inverted approximately 10-15 times over approximately 15 seconds. The 600 ml bag is then hung inverted over the work surface and is allowed to sit for about 3-5 minutes. The blue clamp on tubing leading to the quad set is released, and the cell fraction (the layer under the yellow/orange fat layer) is drained into the quad set. Care is taken to prevent the fat layer from entering the tubing. For example, the flow can be slowed as the fat layer gets close to the tubing by crimping the tubing manually. The tubing leading to the quad bag set is closed with a blue clamp. The tubing leading from the quad set to the 600 ml bag is then heat sealed. The 600 ml bag is then removed and discarded.

Fifth, the regenerative cell composition is washed. A metal clip is placed on the tubing between the two full bags to seal the tubing. The quad set is placed on a balance. Water is added to a second "dummy" quad set to balance the quad set. The quad set and balanced set are placed on opposite buckets of the centrifuge. For the hollow filter, the cells are washed and placed in the bag, and tubing is sealed between the bag and the hollow fiber filter assembly described above. Using a peristaltic pump, the fluid is run through the filter assembly and the cell concentrate is collected in a bag on the downstream end. Care is taken to make sure the quad set bags are not compressed and are upright. The centrifuge is operated at 400×g for 10 minutes. The quad set is removed from the centrifuge and placed in the plasma expressor. Care is taken to place the bags in the expresser in such a way that the hard tubing at the top of the bag is just at the top of the backplate. If the bag is too high, too much saline will be retained, if it is too low the tubing will interfere with the front plate's ability to close and again too much saline will be retained. A blue clamp is applied to each of the lines leading from the full quad set to the empty one. The metal loops and blue clamps are removed to allow supernatant to flow into the empty quad set. As much saline as possible is expressed off, but care is taken not to dislodge the cell pellet. The tubing running into each of the bags containing supernatant is heat sealed. The waste bags containing the supernatant are removed. Blue clamps are applied to the tubing leading to each of the quad set bags containing cells. The bags are taken out of the plasma expresser. A sterile connecting device is used to connect the tubing leading to the quad pack to the saline bag. The blue clamp leading to one of the quad set bags is removed to allow approximately 150 ml saline to flow into the bag, and then the clamp is reapplied to stop the flow of saline. The full quad set bag is then inverted approximately 10-15 times for approximately 15 seconds. The blue clamp leading to the empty quad set bag is then removed and all of the contents of full bag are drained into the empty bag. The metal loop clamp is reapplied to seal the tubing between two quad set bags. The tubing is then heat sealed and the saline bag is removed. The full quad set bag is then inverted approximately 10-15 times over approximately 15 seconds. Another dummy quad set is placed on a balance and is re-balanced to the cell quad set. The quad set bags (one full, one empty) are then placed into the centrifuge so that the quad set bags are not compressed and are upright.

The centrifuge is operated at about 400×g for 10 minutes. The quad set is then removed from the centrifuge and is placed carefully in the plasma expressor in such a way that the hard tubing at the top of the bag is just at the top of the backplate. If the bag is too high too much saline will be retained, if it is too low the tubing will interfere with the front plate's ability to close and again too much saline will be retained. The metal loop is removed to express all the supernatant from the full bag into the empty bag taking care not to dislodge the regenerative cell pellet. The tubing between the bags is sealed, and the full (waste) bag is removed and discarded. A new sampling site coupler is then inserted into the remaining bag. The cells of the cell pellet are then resuspended in the residual saline (if any) to obtain a concentration of regenerative cells. The resuspension can be performed by gentle manipulation of the bag (e.g., squeezing and rubbing).

Figure 4:
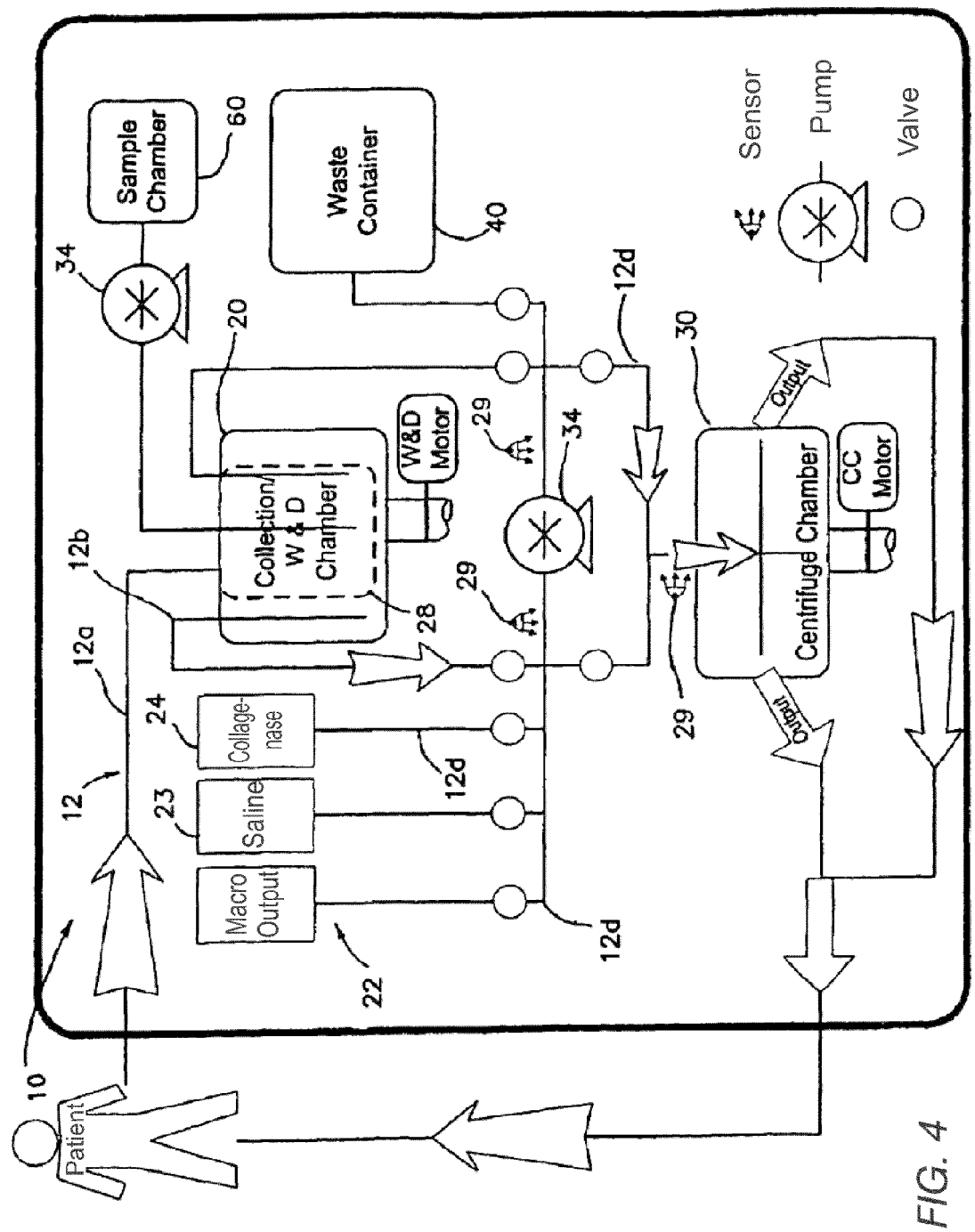
FIG. 4 is an illustration of a system for separating regenerative cells from tissue which includes a centrifuge chamber.

A particular example of the system embodying the present invention is shown in FIG. 4. FIG. 4 illustrates an automated system and method for separating and concentrating regenerative cells from tissue, e.g., adipose tissue, suitable for re-infusion within a patient. In certain embodiments of the system shown in FIG. 4, the system further includes an automated step for aspirating a given amount of tissue from the patient. The system shown in FIG. 4 is comprised of the disposable set shown in FIG. 13 which is connected to the re-usable component of the system shown in FIG. 14 to arrive at an automated embodiment of the system shown in FIG. 15A. The disposable set is connected to the re-usable component through, e.g., an interlocking or docking device or configuration, which connects the disposable set to the re-usable component such that the disposable set is securely attached to and associated with the re-usable hardware component in a manner that the processing device present on the re-usable component can control and interface with, i.e., send and receive signals to and from the various components of the disposable set as well as various components of the re-usable component and other associated devices and systems.

The user may connect the disposable set to the re-usable component, input certain parameters using the user interface, e.g., the volume of tissue being collected, attach the system to the patient, and the system automatically performs all of the steps shown in FIG. 4 in an uninterrupted sequence using pre-programmed and/or user input parameters. One such sequence is illustrated in FIG. 15B. Alternatively, the tissue may be manually aspirated from the patient by the user and transported to system for processing, i.e., separation and concentration of regenerative cells.

Specifically, as shown in FIG. 4, tissue, e.g., adipose tissue, may be withdrawn from the patient using conduit 12 and introduced into collection chamber 20. A detailed illustration of the collection chamber of FIG. 4 is shown in FIG. 5. As illustrated in FIG. 5, the collection chamber 20 may be comprised of a vacuum line 11 which facilitates tissue removal using a standard cannula. The user may enter the estimated volume of tissue directed to the collection chamber 20 at this point. The tissue is introduced into the collection chamber 20 through an inlet port 21 which is part of a closed fluid pathway that allows the tissue, saline and other agents to be added to the tissue in an aseptic manner. An optical sensor of the system, e.g., sensor 29, can detect when the user input volume of tissue is present in the collection chamber 20. In certain embodiments, if less tissue is present in the collection chamber than the user input, the user will have the option to begin processing the volume of tissue which is present in the collection chamber 20. In certain embodiments, a portion of the tissue removed from the patient may be directed to the sample chamber 60 through the use of a pump, e.g., a peristaltic pump, via a conduit, which may be activated via user input utilizing the user interface.

A sensor 29 can signal the processing device present in the re-usable component to activate the steps needed to wash and disaggregate the tissue. For example, the processing device may introduce a pre-set volume of washing agent based on the volume of tissue collected using automated valves and pumps. This cycle may be repeated in the collection chamber until the optical sensor determines that the effluent liquid is sufficiently clear and devoid of unwanted material. For example, an optical sensor 29 along the conduit leading out of the collection chamber 12b or 12d can detect that the unwanted materials have been removed and can signal the processing device to close the required valves and initiate the next step.

Next, the processing device may introduce a pre-programmed amount of disaggregation agent based on the volume of tissue collected. The processing device may also activate agitation of the tissue in the collection chamber for a preset period of time based on the initial volume of tissue collected or based on user input. In the embodiment shown in FIG. 4, once the disaggregation agent, e.g., collagenase, is added to the collection chamber 20 through the collagenase source 24, the motor in the collection chamber 20 is activated via the processing device. The motor activates the rotatable shaft 25 which is comprised of a magnetic stirrer and a paddle-like device wherein one or more paddles 25a are rigidly attached to the filter cage 27 of a filter prefixed to the collection chamber 28. The paddles agitate the in the presence of the disaggregation agent such that the regenerative cells separate from the tissue.

The solution in the collection chamber 20 is allowed to settle for a preset period of time. The buoyant portion of the solution is allowed to rise to the top of the solution. Once the preset period of time elapses, the necessary valves and pumps are activated by the processing device to remove the non-buoyant portion to the waste chamber 40. The transfer into the waste chamber 40 continues until a sensor 29 along the conduit leading out of the collection chamber 12b or 12d can detect that the buoyant fraction of the solution is about to be transferred to the waste chamber 30. For example, a sensor 29 along the conduit leading out of the collection chamber 12b or 12d can detect that the unwanted materials have been removed and can signal the processing device to close the required valves.

At this time the non-buoyant fraction of the solution, i.e., the regenerative cell composition, is moved to the processing chamber 30. This is accomplished through the use of the necessary valves and peristaltic pumps. In certain embodiments, before transfer of the regenerative cell composition to the processing chamber 30, an additional volume of saline may be added to the buoyant fraction of solution remaining in the collection chamber 20. Another wash cycle may be repeated. After this cycle, the solution is allowed to settle and the non-buoyant fraction (which contains the regenerative cells) is transported to the processing chamber 30 and the buoyant fraction is drained to the waste chamber 40. The additional wash cycle is used to optimize transfer of all the separated regenerative cells to the processing chamber 30.

Once the regenerative cell composition is transported to the processing chamber 30 by way of conduits 12, the composition may be subject to one or more additional washing steps prior to the start of the concentration phase. This ensures removal of waste and residual contaminants from the collection chamber 20. Similarly, subsequent to the concentration step, the regenerative cell composition may be subjected to one or more additional washing steps to remove residual contaminants. The unwanted materials may be removed from the processing chamber 30 to the waste chamber 40 in the same manner, i.e., control of valves and pumps via signals from the processing device, as described above.

The various embodiments of the processing chamber 30 shown in FIG. 4 are described in detail below. The processing chamber 30 shown in FIG. 4 is in the form of a centrifuge chamber. A detailed illustration of the processing chamber of FIG. 4 is shown in FIGS. 7 and 8. Such a processing chamber 30 is generally comprised of a rotating seal network 30.1 comprising an outer housing 30.2, one or more seals 30.3, one or more bearings 30.4 and an attachment point 30.6 for connecting the processing chamber to the centrifuge device present in the re-usable component of the system; one or more fluid paths 30.5 in the form of conduits extending out from the rotating seal and ending in a centrifuge chamber on each end which is in the form of an output chamber 50 housed in a frame 53 wherein the frame is comprised of one or more ports 52 and one or more handles to manually re-position the output chamber 50.

The rotating seal network 30.1 is included to ensure that the fluid pathways of the processing chamber can be maintained in a sterile condition. In addition, the fluid pathways of the processing chamber can be accessed in a sterile manner (e.g., to add agents or washing solution) at any time, even while the centrifuge chamber of the processing chamber is spinning.

The rotating seal network 30.1 shown in FIGS. 7 and 8 includes a rotating shaft comprised of two or more bearings 30.4, three or more lip seals 30.3, and an outer housing 30.2. In this embodiment, the bearings 30.4 further comprise an outer and inner shaft (not shown) referred to herein as races. These races may be separated by precision ground spheres. The races and spheres comprising the bearings are preferably fabricated with material suitable for contact with bodily fluid, or are coated with material suitable for contact with bodily fluid. In a preferred embodiment, the races and spheres are fabricated using, for example, silicone nitride or zirconia. Furthermore, in this embodiment, the three lip seals are comprised of a circular "U" shaped channel (not shown) as well as a circular spring (not shown). The circular "U" shaped channel is preferably fabricated using flexible material such that a leakage proof junction with the rotating shaft of the rotating seal network 30.1 is formed. Additionally, the lip seals are preferably oriented in a manner such that pressure from the regenerative cell composition flowing through the processing chamber causes the seal assembly to tighten its junction with the rotating shaft by way of increased tension. The seals may be secured in position by way of one or more circular clips (not shown) which are capable of expanding and/or collapsing as needed in order to engage a groove in the outer housing 30.2 of the rotating seal network 30.1. The heat generated by or near the rotating seal network 30.1 must be controlled to prevent lysis of the cells in the solution which is being moved through the passage. This may be accomplished by, for example, selecting a hard material for constructing the rotating shaft, polishing the area of the rotating shaft which comes in contact with the seals and minimizing contact between the rotating shaft and the seal.

In another embodiment the rotating seal network 30.1 is comprised of a single rubber seal 30.3 and an air gasket (not shown). This seal and gasket provide a tortuous path for any biologic matter which could compromise the sterility of the system. In another embodiment the rotating seal network 30.1 is comprised of multiple spring loaded seals 30.3 which isolate the individual fluid paths. The seals 30.3 are fabricated of a material which can be sterilized as well as seal the rotating shaft without lubricant. In another embodiment the rotating seal network 30.1 is compromised of a pair of ceramic disks (not shown) which create the different fluid paths and can withstand the rotation of the system and not cause cell lysis. In another embodiment the fluid pathway is flexible and is allowed to wind and unwind with respect to the processing chamber. This is accomplished by having the flexible fluid pathway rotate one revolution for every two revolutions of the processing chamber 30. This eliminates the need for a rotating seal altogether.

The regenerative cell composition is pumped from the collection chamber 20 along a fluid path through the axis of rotation of the rotating seal network 30.1 and then divides into a minimum of two fluid pathways 30.5 each of which radiate outward from the central axis of the processing chamber 30 and terminate near the outer ends of the processing chamber 30, i.e., within the centrifuge chambers which house the output chambers 50 (FIGS. 7 and 8). Accordingly, in a preferred embodiment, the processing chamber 30 is comprised of two or more output chambers 50 as shown in FIGS. 7 and 8. These output chambers 50 are positioned such that they are in one orientation during processing 30.7 and another orientation for retrieval of concentrated regenerative cells 30.8. For example, the output changes are tilted in one angle during processing and another angle for cell retrieval. The cell retrieval angle is more vertical than the processing angle. The two positions of the output chamber 50 may be manually manipulated through a handle 53 which protrudes out of the processing chamber 30. The regenerative cells can be manually retrieved from the output chambers 50 when they are in the retrieval orientation 30.8 using a syringe. In another embodiment, fluid path 30.5 is constructed such that it splits outside the processing chamber and then connects to the outer ends of the processing chamber 30, i.e., within the centrifuge chambers which house the output chambers 50 (not shown). In this embodiment, large volumes of regenerative cell composition and/or additives, solutions etc. may be transported to the centrifuge chamber and/or the output chambers directly.

With reference to FIGS. 4 and 7-9, between the collection chamber 20 and the processing chamber 30, a pump 34 and one or more valves 14 may be provided. In a preferred embodiment, the valves 14 are electromechanical valves. In addition, sensors, such as pressure sensor 29, may be provided in line with the processing chamber 30 and the collection chamber 20. The valves, pumps and sensors act in concert with the processing device present on the re-usable component (FIG. 14) to automate the concentration steps of the system.

The sensors detect the presence of the regenerative cell composition in the centrifuge chambers and activate the centrifuge device through communication with the processing device of the system. The regenerative cell composition is then subjected to a pre-programmed load for a pre-programmed time based on the amount of tissue originally collected and/or user input. In certain embodiments, this step may be repeated either automatically or through user input. For example, the composition is subjected to a load of approximately 400 times the force of gravity for a period of approximately 5 minutes. The output chamber 50 is constructed such that the outer extremes of the chamber form a small reservoir for the dense particles and cells. The output chamber 50 retains the dense particles in what is termed a 'cell pellet', while allowing the lighter supernatant to be removed through a fluid path, e.g., a fluid path which is along the axis of rotation of the rotating seal network 30.1 and travels from the low point in the center of the processing chamber 30 through the rotating seal network 30.1 to the waste container 40. The valves 14 and pumps 34 signal the processing device to activate steps to remove the supernatant to the waste container 40 without disturbing the cell pellet present in the output chamber 50.

The cell pellet that is obtained using the system shown in FIG. 4 comprises the concentrated regenerative cells of the invention. In some embodiments, after the supernatant is removed and directed to the waste chamber 40, a fluid path 30.5 may be used to re-suspend the cell pellet that is formed after centrifugation with additional solutions and/or other additives. Re-suspension of the cell pellet in this manner allows for further washing of the regenerative cells to remove unwanted proteins and chemical compounds as well as increasing the flow of oxygen to the cells. The resulting suspension may be subjected to another load of approximately 400 times the force of gravity for another period of approximately 5 minutes. After a second cell pellet is formed, and the resulting supernatant is removed to the waste chamber 40, a final wash in the manner described above may be performed with saline or some other appropriate buffer solution. This repeated washing can be performed multiple times to enhance the purity of the regenerative cell solution. In certain embodiments, the saline can be added at any step as deemed necessary to enhance processing. The concentrations of regenerative cells obtained using the system shown in FIG. 4 may vary depending on amount of tissue collected, patient age, patient profile etc. Exemplary yields are provided in Table I.

The final pellet present in the output chamber 50 may then be retrieved in an aseptic manner using an appropriate syringe after the output chamber 50 is positioned in the orientation appropriate for cell removal. In other embodiments, the final pellet may be automatically moved to a container in the in the output chamber 50 which may be removed and stored in or used as needed. This container may be in any appropriate form or size. For example, the container may be a syringe. In certain embodiments, the output container 50 itself may be heat sealed (either automatically or manually) and isolated from the other components of the processing chamber for subsequent retrieval and use of the regenerative cells in therapeutic applications as described herein including re-infusion into the patient. The cells may also be subject to further processing as described herein either prior to retrieval from the output chamber or after transfer to a second system or device. The re-usable component shown in FIG. 14 is constructed such that it can be connected to one or more additional systems or devices for further processing as needed.

Methods of Treating Renal Diseases and Disorders Using Regenerative Cells (ADC)

As described herein, the regenerative cells obtained using the systems and methods of the present invention can be used to treat renal diseases and disorders based on their properties as described in the Examples. For example, the regenerative cells have the ability to synthesize and secrete growth factors stimulating new blood vessel formation, the ability to synthesize and secrete growth factors stimulating cell survival and proliferation and the ability to proliferate and differentiate into cells directly participating in new blood vessel formation. Accordingly, in one aspect of the present invention, regenerative cells are extracted from a donor's adipose tissue using the systems and methods of the present invention and are used to elicit a therapeutic benefit to damaged or degenerated renal tissue through one or more of the mechanisms demonstrated herein. In a preferred embodiment the cells are extracted from the adipose tissue of the person into whom they are to be implanted, thereby reducing potential complications associated with antigenic and/or immunogenic responses to the transplant. Patients are typically evaluated to assess renal damage or disease by one or more of the following procedures performed by a physician or other clinical provider: patient's health history, physical examination, and objective data including but not limited to serum creatinine, serum blood urea nitrogen, serum chemistry profiles, urinalysis, glomerular filtration rate and ultrasound.

In one embodiment, the harvesting procedure is performed prior to the patient receiving any products designed to reduce blood clotting in connection with treatment of the renal disorder. However, in certain embodiments, the patient may have received aspirin prior to the harvesting procedure. In addition, one preferred method includes collection of adipose tissue prior to any attempted procedure. However, as understood by persons skilled in the art, the timing of collection is expected to vary and will depend on several factors including, among other things, patient stability, patient coagulation profile, provider availability, and quality care standards. Ultimately, the timing of collection will be determined by the practitioner responsible for administering care to the affected patient.

The volume of adipose tissue collected from the patient can vary from about 0 cc to about 2000 cc and in some embodiments up to about 3000 cc. The volume of fat removed will vary from patient to patient and will depend on a number of factors including but not limited to: age, body habitus, coagulation profile, hemodynamic stability, severity of disease, co-morbidities, and physician preference.

Cells may be administered to a patient in any setting in which renal function is compromised. Examples of such settings include, but are not limited to post-surgical traumatic injury, hypovolemic shock and renal artery thrombosis among other things. The cells may be extracted in advance and stored in a cryopreserved fashion or they may be extracted at or around the time of defined need. As disclosed herein, the cells may be administered to the patient, or applied directly to the damaged tissue, or in proximity of the damaged tissue, without further processing or following additional procedures to further purify, modify, stimulate, or otherwise change the cells. For example, the cells obtained from a patient may be administered to a patient in need thereof without culturing the cells before administering them to the patient. In one embodiment, the collection of adipose tissue will be performed at a patient's bedside. Hemodynamic monitoring may be used to monitor the patient's clinical status.

In accordance with the invention, the regenerative cells can be delivered to the patient soon after harvesting the adipose tissue from the patient. For example, the cells may be administered immediately after the processing of the adipose tissue to obtain a composition of regenerative cells. In one embodiment, the preferred timing of delivery should take place on the order of hours to days after the renal failure. In another embodiment, the timing for delivery may be relatively longer if the cells to be re-infused to the patient are subject to additional modification, purification, stimulation, or other manipulation, as discussed herein. Furthermore, the regenerative cells may be administered multiple times. For example, the cells may be administered continuously over an extended period of time (e.g., hours), or may be administered in multiple bolus injections extended over a period of time. In certain embodiments, an initial administration of cells will be administered within about 12 hours after renal failure, such as at 6 hours, and one or more doses of cells will be administered at 12 hour intervals.

The number of cells administered to a patient may be related to, for example, the cell yield after adipose tissue processing. A portion of the total number of cells may be retained for later use or cyropreserved. In addition, the dose delivered will depend on the route of delivery of the cells to the patient. In one embodiment of the invention, to the number of regenerative cells to be delivered to the patient is expected to be about $5.5 \times 10^4$ cells. However, this number can be adjusted by orders of magnitude to achieve the desired therapeutic effect.

The cells may also be applied with additives to enhance, control, or otherwise direct the intended therapeutic effect. For example, in one embodiment, and as described herein, the cells may be further purified by use of antibody-mediated positive and/or negative cell selection to enrich the cell population to increase efficacy, reduce morbidity, or to facilitate ease of the procedure. Similarly, cells may be applied with a biocompatible matrix which facilitates in vivo tissue engineering by supporting and/or directing the fate of the implanted cells. In the same way, cells may be administered following genetic manipulation such that they express gene products that are believed to or are intended to promote the therapeutic response(s) provided by the cells. Examples of manipulations include manipulations to control (increase or decrease) expression of factors promoting angiogenesis or vasculogenesis (for example VEGF. The cells may also be subjected to cell culture on a scaffold material prior to being implanted as described herein.

In one embodiment, direct administration of cells to the site of intended benefit is preferred. This may be achieved by intravenous injection. Routes of administration known to one of ordinary skill in the art, include but are not limited to, intravenous, intraarterial, intraparenchymal and may or may not include a catheter based mechanism of delivery. Cells may be injected in a single bolus, through a slow infusion, or through a staggered series of applications separated by several hours or, provided cells are appropriately stored, several days or weeks. As set forth above, the regenerative cells may also be applied by use of catheterization such that the cells are delivered directly into the renal parenchyma through the renal artery. As with peripheral venous access, cells may be injected through the catheters in a single bolus or in multiple smaller aliquots. Cells may also be applied directly to the renal parenchyma at the time of open exploration or via percutaneous catheter delivery.

In one embodiment, the route of delivery will include intravenous delivery through a standard peripheral intravenous catheter or a central venous catheter. The flow of cells may be controlled by serial inflation/deflation of distal and proximal balloons located within the patient's vasculature, thereby creating temporary no-flow zones which promote cellular engraftment or cellular therapeutic action. Furthermore, cells could be delivered through the following routes, alone, or in combination with one or more of the approaches identified above: subcutaneous, intramuscular, sublingual, or via a dialysis machine. In one embodiment, cells are administered to the patient as an intra-vessel bolus or timed infusion. In another embodiment, cells may be resuspended in an artificial or natural medium or tissue scaffold prior to being administered to the patient.

The cell dose administered to the patient will be dependent on the amount of adipose tissue harvested and the body mass index of the donor (as a measure of the amount of available adipose tissue). The amount of tissue harvested will also be determined by the extent of the renal disease or degeneration. Multiple treatments using multiple tissue harvests or using a single harvest with appropriate storage of cells between applications are within the scope of this invention.

Portions of the processed lipoaspirate may be stored before being administered to a patient. For short term storage (less than 6 hours) cells may be stored at or below room temperature in a sealed container with or without supplementation with a nutrient solution. Medium term storage (less than 48 hours) is preferably performed at 2-8° C. in an isosmotic, buffered solution (for example Plasmalyte®) in a container composed of or coated with a material that prevents cell adhesion. Longer term storage is preferably performed by appropriate cryopreservation and storage of cells under conditions that promote retention of cellular function, such as disclosed in commonly owned and assigned PCT application number PCT/US02/29207, filed Sep. 13, 2002 and U.S. Provisional application No. 60/322,070, filed Sep. 14, 2001, the contents of both of which are hereby incorporated by reference.

In accordance with one aspect of the invention, the adipose-tissue derived cells that are administered to a patient can act as growth factor delivery vehicles. For example, by engineering the cells to express one or more growth factors suitable for alleviating symptoms associated with a renal disorder or disease, the cells can be administered to a patient, and engineered to release one or more of the growth factors. The release can be provided in a controlled fashion for extended periods of time. For example, the release can be controlled so that the growth factor(s) are released in a pulsed or periodic manner such that there are local elevations in growth factor, and/or local recessions in the amount of growth factor in proximity to an injured area of tissue.

The cells that are administered to the patient not only help restore function to damaged or otherwise unhealthy tissues, but also facilitate remodeling of the damaged tissues.

Cell delivery may take place but is not limited to the following locations: clinic, clinical office, emergency department, hospital ward, intensive care unit, operating room, catheterization suites, and radiologic suites.

In one embodiment, the effects of cell delivery therapy would be demonstrated by, but not limited to, one of the following clinical measures: acute decrease in serum creatinine and blood urea nitrogen, and evidence of increased perfusion to the renal parenchyma as evidenced by increasing urine output, and increased GFR. The effects of cellular therapy can be evident over the course of days to weeks after the procedure. However, beneficial effects may be observed as early as several hours after the procedure, and may persist for several years.

Patients are typically monitored prior to and during the deliver of the cells. Monitoring procedures include, and are not limited to: coagulation studies, oxygen saturation and hemodynamic monitoring. After delivery of cells, patients may require an approximate 24 hour period of monitoring for adverse events.

The following examples are provided to demonstrate particular situations and settings in which this technology may be applied and are not intended to restrict the scope of the invention and the claims included in this disclosure.

EXAMPLES

The ADC or regenerative cells used throughout the examples set forth below can be obtained by the method(s) described in the instant disclosure and/or the method(s) described in U.S. application Ser. No. 10/316,127, entitled SYSTEMS AND METHODS FOR TREATING PATIENTS WITH PROCESSED LIPOASPIRATE CELLS, filed Dec. 9, 2002, which claims priority to U.S. Provisional Application Ser. No. 60/338,856, filed Dec. 7, 2001, as well as well as the methods described in U.S. application Ser. No. entitled, SYSTEMS AND METHODS FOR SEPARATING AND CONCENTRATING REGENERATIVE CELLS FROM TISSUE, filed Jun. 25, 2004, which claims priority to U.S. application Ser. No. 10/316,127, entitled SYSTEMS AND METHODS FOR TREATING PATIENTS WITH PROCESSED LIPOASPIRATE CELLS, filed Dec. 9, 2002, which are all commonly assigned and the contents of all of which are expressly incorporated herein by this reference.

Example 1

Expression of Angiogenic Growth Factor, VEGF, by Regenerative Cells

Vascular Endothelial Growth Factor (VEGF) is one of the key regulators of angiogenesis (Nagy et al., 2003; Folkman, 1995). Placenta Growth Factor, another member of the VEGF family, plays a similar role in both angiogenesis as well as arteriogenesis. Specifically, transplant of wild-type (PIGF+/+) cells into a PIGF knockout mouse restores ability to induce rapid recovery from hind limb ischemia (Scholz et al., 2003).

Figure 16A:
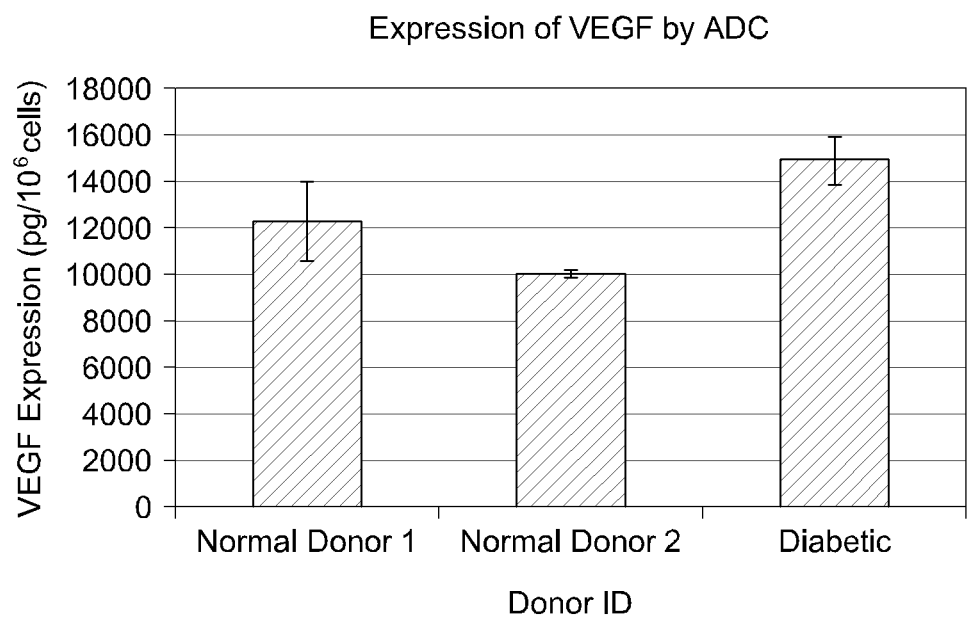
FIGS. 16A and 16B depict the expression of VEGF (5A) and PIGF (5B) protein by cultured adipose derived stem cells.
Figure 16B:
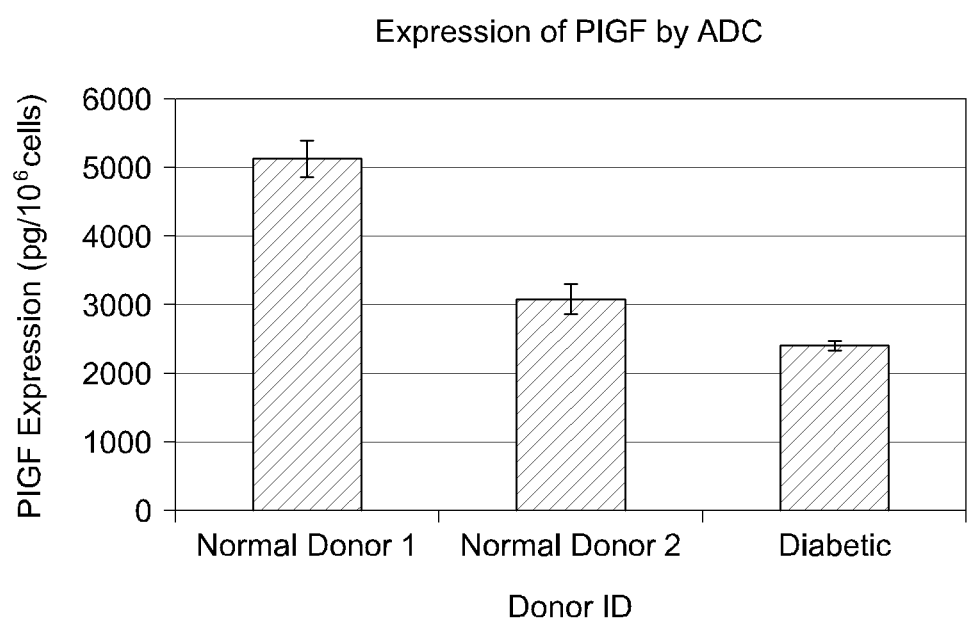

Given the importance of angiogenesis and arteriogenesis to the revascularization process, PIGF and VEGF expression by the regenerative cells of the present invention was examined using an ELISA assay (R&D Systems, Minneapolis, Minn.) using adipose derived regenerative cells from three donors. One donor had a history of hyperglycemia and Type 2 diabetes (a condition highly associated with microvascular and macrovascular disease). Regenerative cells from each donor were plated at 1,000 cells/cm$^2$ in DMEM/F-12 medium supplemented with 10% FCS and 5% HS and grown until confluent. Supernatant samples were taken and assayed for expression of PIGF and VEGF protein. As shown in FIGS. 16A and 16B, the results demonstrate robust expression of both VEGF (FIG. 16A) and PIGF (FIG. 16B) by the adipose derived regenerative cells of the invention.

In a separate study, the relative quantity of angiogenic related cytokines secreted by cultured regenerative cells from normal adult mice was measured. The regenerative cells were cultured in alpha-MEM with 10% FBS to five days beyond cell confluence, at which time the cell culture medium was harvested and evaluated by antibody array analysis (RayBio® Mouse Cytokine Antibody Array II (RayBiotech, Inc.). The following angiogenic related growth factors were detected: Vascular Endothelial Growth Factor (VEGF), bFGF, IGF-II, Eotaxin, G-CSF, GM-CSF, IL-12 p40/p70, IL-12 p70, IL-13, IL-6, IL-9, Leptin, MCP-1, M-CSF, MIG, PF-4, TIMP-1, TIMP-2, TNF-α, and Thrombopoetin. The following angiogenic related growth factors or cytokines were elevated at least twice compare to blank control medium with 10% FBS: Vascular Endothelial Growth Factor (VEGF), Eotaxin, G-CSF, IL-6, MCP-1 and PF-4.

These data demonstrate that the regenerative cells of the present invention express a wide array of angiogenic and arteriogenic growth factors. Moreover, the finding that a diabetic patient expressed VEGF and PIGF at equivalent levels to those of normal patients suggest that diabetic patients may be candidates for angiogenic therapy by autologous adipose derived regenerative cells.

Example 2

Regenerative Cells Contain Cell Populations that Participate in Angiogenesis

Endothelial cells and their precursors, endothelial progenitor cells (EPCs), are known to participate in angiogenesis. To determine whether EPCs are present in adipose derived regenerative cells, human adipose derived regenerative cells were evaluated for EPC cell surface markers, e.g., CD-34.

ADCs were isolated by enzymatic digestion of human subcutaneous adipose tissue. ADCs (100 μl) were incubated in phosphate saline buffer (PBS) containing 0.2% fetal bovine serum (FBS), and incubated for 20 to 30 minutes at 4° C. with fluorescently labeled antibodies directed towards the human endothelial markers CD-31 (differentiated endothelial cell marker) and CD-34 (EPC marker), as well as human ABCG2 (ATP binding cassette transporter), which is selectively expressed on multipotent cells. After washing, cells were analyzed on a FACSAria Sorter (Beckton Dickenson—Immunocytometry). Data acquisition and analyses were then performed by FACSDiva software (BD-Immunocytometry, Calif.). The results (not shown) showed that the adipose derived regenerative cells from a healthy adult expressed the EPC marker CD-34 and ABCG2, but not the endothelial cell marker CD-31. Cells expressing the EPC marker CD-34 and ABCG2 were detected at similar frequency in regenerative cells derived from a donor with a history of diabetes.

Figure 17:
FIG. 17 depicts detection of endothelial progenitor cells within adipose derived stem cell populations.

To determine the frequency of EPCs in human adipose derived regenerative cells after their culture in endothelial cell differentiation medium, regenerative cells were plated onto fibronectin-coated plates and cultured in endothelial cell medium for three days to remove mature endothelial cells. Nonadherent cells were removed and re-plated. After 14 days, colonies were identified by staining with FITC-conjugated Ulex europaeus Agglutinin-1 (Vector Labs, Burlingame, Calif.) and DiI-labeled acetylated LDL (Molecular Probes, Eugene, Oreg.). As shown in FIG. 17, the results indicate an EPC frequency of approximately 500 EPC/$10^6$ ADC cells.

The presence of EPCs within the adipose tissue derived regenerative cells indicates that these cells can participate directly in development of new blood vessels and enhance angiogenesis and reperfusion.

Example 3

In Vitro Development of Vascular Structures in Regenerative Cells

Figures 18A, 18B:
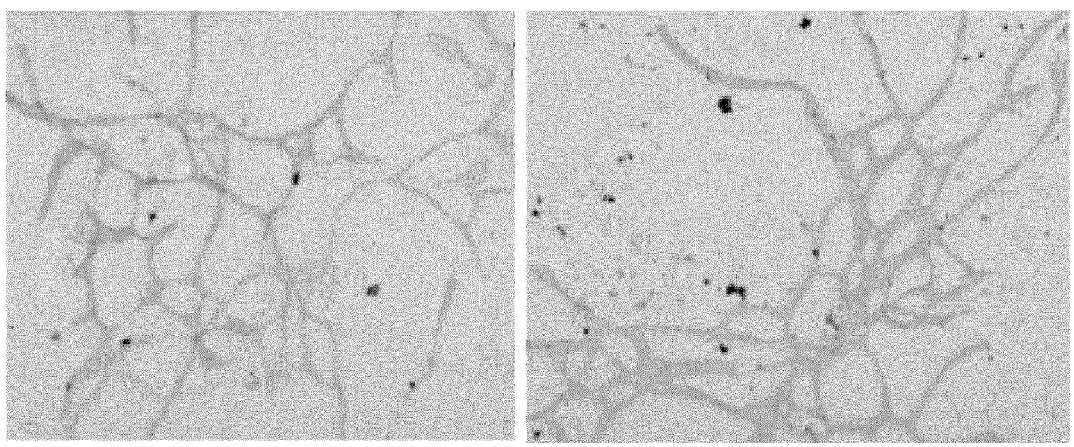
FIGS. 18A and 18B depict the in vitro development of vascular structures in both normal (7A) and streptozotocin-treated (7B) mice.
Figure 19:
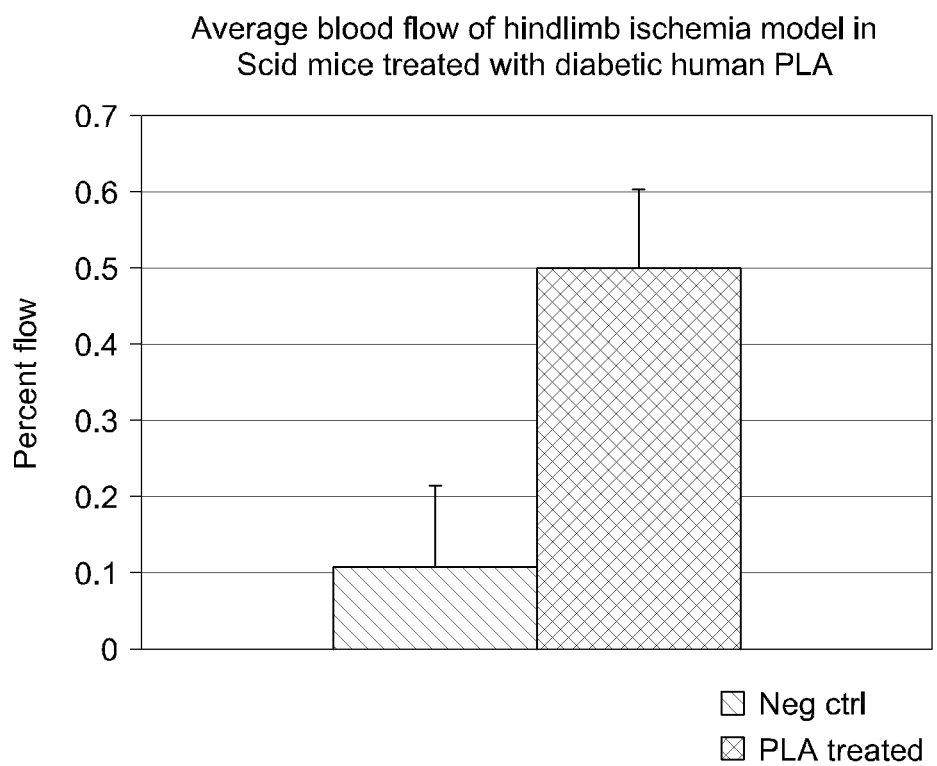
FIG. 19 depicts the increased average restoration of blood flow in hindlimb ischemia mice treated with adipose derived stem cell compared to a negative control.

An art-recognized assay for angiogenesis is one in which endothelial cells grown on a feeder layer of fibroblasts develop a complex network of CD31-positive tubes reminiscent of a nascent capillary network (Donovan et al., 2001). Since adipose derived regenerative cells contain endothelial cells, EPCs and other stromal cell precursors, we tested the ability of these regenerative cells to form capillary-like structures in the absence of a feeder layer. Regenerative cells obtained from inguinal fat pads of normal mice developed capillary networks two weeks after culture (FIG. 18A). Notably, regenerative cells from hyperglycemic mice with streptozotocin (STZ)-induced Type 1 diabetes eight weeks following administration of STZ formed equivalent capillary networks as those formed by cells from normal mice (FIG. 18B).

In a subsequent study, adipose derived regenerative cells were cultured in complete culture medium (α-MEM supplemented with 10% FCS) and no additional growth factors. These regenerative cells also formed capillary networks. Furthermore, the vascular structures formed stained positive for the endothelial cell markers CD31, CD34, VE-cadherin and von Willebrand factor/Factor VIII, but not the pan-lymphocyte marker, CD45.

To compare the ability of regenerative cells from young vs. elderly mice to form capillary networks, regenerative cells from normal young and elderly mice (aged 1, 12, or 18 months) were cultured for 2 weeks in complete culture medium (α-MEM supplemented with 10% FCS) and no additional growth factors. Equivalent capillary-like networks were observed in cultures of regenerative cells from all donors (not shown).

The foregoing data demonstrates that adipose derived regenerative cells from normal and diabetic, as well as young and elderly patients can form vascular structures consistent with the formation of nascent capillary networks. Accordingly, the regenerative cells of the invention may be used to treat angiogenic insufficiencies.

Example 4

In Vivo Development of Vascular Structures in Regenerative Cells

In vitro angiogenic potential, while promising, is of little value if the cells do not exert in vivo angiogenic activity. Surgically inducing hind limb ischemia is an in vivo model capable of identifying the angiogenic potential of a given therapy. This model was developed in immunodeficient (NOD-SCID) mice in which the ability of human cells to drive reperfusion could be observed.

Pre-operative blood flow values were determined for both hind limbs as described below. The vasculature of anesthetized mice was tied off with a 4-0 silk ligature at the following sites: 1) iliac artery proximal to its bifurcation, 2) just distal to the origin of deep femoral artery, 3) just proximal to branching of the superficial femoral artery. After ligation, the vasculature was removed en bloc. Prior to wound closure, grossly observable collaterals branching from the ligated femoral arteries were also ligated. Twenty four hours later, 129S mice were injected with $5 \times 10^6$ syngeneic mouse adipose derived regenerative cells and NOD SCID mice were injected with human adipose derived regenerative cells through the tail vein. Flow was imaged immediately after surgery and at intervals following treatment using a Laser Doppler Flow Imager (Moor Instruments Inc., Wilmington, Del.). Measurements, taken three times per week for 24 days, were normalized to the pre-operative value for that limb and presented relative to the control (unoperated) limb.

The model of hind limb ischemia is extremely sensitive to the strain of mouse used. NOD SCID mice are immunodeficient animals, lacking the ability to ignite an acute inflammatory response. For these mice, this surgical approach generates severe ischemia such that two thirds of untreated animals lost hind limb structures below the site of femoral excision. No cell-treated animal lost any structures above the toe. Yet, for immunocompetent 129S mice, no untreated animals lost any structures above the phalanges and displayed an endogenous ability to partially regenerate reperfusion. This could be due to the intrinsic angiogenesis associated with an acute inflammatory response. This may explain why reperfusion was less extreme when comparing the treated versus control animals of different strains.

However, the results showed that mice treated with adipose derived regenerative cells showed significantly improved perfusion as compared to untreated mice of both strains. By Day 12, blood flow was restored to 50±11% in NOD-SCID mice treated with human regenerative cells, as compared to 10±10% in untreated mice (p<0.05). Similarly, immunocompetent 129 S mice exhibited 80±12% restoration of flow at day 14, as compared to 56±4% in untreated mice In addition, gross dissection of mice revealed the appearance of collateral vessels in the hind limbs of mice treated with regenerative cells, but not in those from untreated mice or in the healthy limbs of any mice.

Example 5

Increasing ADC Dose is Associated with Improved Graft Survival and Angiogenesis

Transplant of autologous adipose tissue is a relatively common procedure in plastic and reconstructive surgery {Fulton, 1998; Shiffman, 2001}. However, this procedure is limited by the fact that the adipose tissue fragments are transferred without a vascular supply and, as a result, graft survival is dependent upon neovascularization (Coleman, 1995; Eppley et al., 1990). Thus, in a limited way, the transplanted tissue represents an ischemic tissue.

A study in Fisher rats was performed in which adipose tissue fragments were transplanted into the subcutaneous space over the muscles of the outer thigh. The right leg was transplanted with 0.2 g of adipose tissue fragments alone, the left leg with 0.2 g of adipose tissue fragments supplemented by addition of adipose derived stem cells at three different doses ($1.7 \times 10^5$-$1.3 \times 10^6$ cells/graft; three animals per dose); in this way the contralateral leg acted as a control. Animals were then maintained for one month after which the animals were euthanized and the grafts recovered, weighed, fixed in formalin and embedded in paraffin for histologic analysis.

Figure 20A:
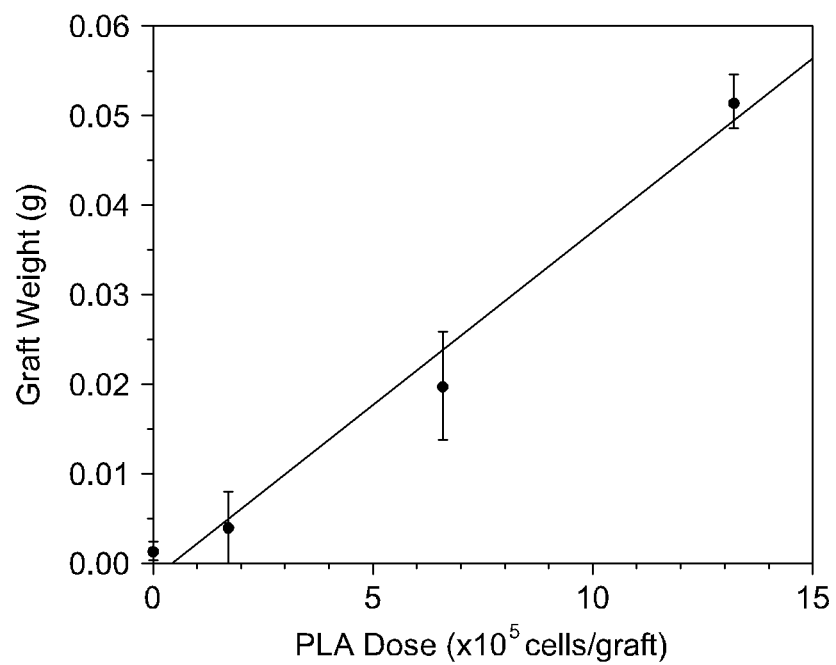
FIGS. 20A and 20B shows that increasing adipose derived stem cell dose improves graft survival and angiogenesis (20A) and depicts the retention of adipose tissue architecture in histologic specimen (20B).
Figure 20B:
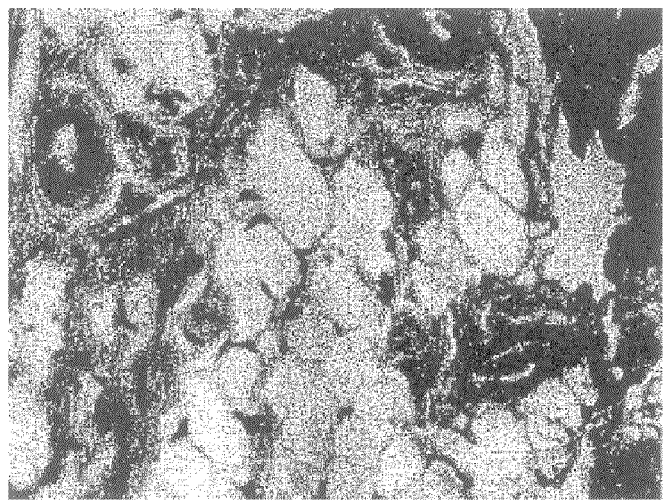

As shown in FIG. 9A, the results show minimal retention of grafted tissue in the control leg and a dose-dependent increase in retention of graft weight in the treated leg. Further, immunohistochemical analysis of the grafts showed considerable neoangiogenesis and perfusion in the adipose derived stem cell treated grafts (FIG. 20B, arrows). This was also associated with retention of adipose tissue morphology (FIG. 20B).

Accordingly, Examples 1-5 demonstrate that the adipose derived regenerative cells of the invention secrete angiogenic and arteriogenic growth factors; form nascent capillary networks in vitro; enhance survival of fat grafts; and enhance ischemic reperfusion. Thus, the regenerative cells of the invention are capable of promoting angiogenesis and arteriogenesis. And may be functional in treating multiple diseases with underlying circulatory insufficiencies.

Example 6

Treatment of Acute Renal Failure

Acute renal failure results in ischemic injury to the renal parenchyma. Tissue damage can be minimized by reperfusion of the damaged tissue and by regeneration of renal tissue (Sujata K, Karihaloo A, Clark P R, Kashgarian M, et al. Bone Marrow Stem Cells Contribute to Repair of the Ischemically Injured Renal Tubule. JCI. 112:4249, 2003; Poulsom R, et al. Bone marrow contributes to renal parenchymal turnover and regeneration. J. Pathol. 195:229-235. 2001).

Adipose derived regenerative cell therapy, as disclosed herein, seeks to provide a superior source of regenerative cells relative to non-adipose derived cellular therapies, due to, e.g., the use of a greater number of non-cultured cells and more pure cells with attenuated morbidity than that associated with non-adipose derived therapies, such as bone marrow harvesting.

A patient is suspected of acute tubular necrosis and is demonstrating beginning or established signs and symptoms consistent with acute renal failure. The patient is typically already admitted to the hospital. The patient is prescribed regenerative cell therapy. The patient's habitus is examined for a site suitable for adipose tissue collection. Harvest sites are characterized by at least one of the following: potential space(s) limited by normal anatomical structures, no major vascular or visceral structures at risk for damage, and ease of access. Virgin harvest sites are preferred, but a previous harvest site does not preclude additional adipose tissue harvest. Potential harvest sites include, but are not limited to, the following: lateral and medial thigh regions of bilateral lower extremities, and anterior abdominal wall pannus.

The patient receives a subcutaneous injection of a tumescent fluid solution containing a combination of lidocaine, saline, and epinephrine in for example different standardized dosing regimens. Using a scalpel (e.g., an 11-blade scalpel), a small puncture wound is made in the patient's medial thigh region of his right and/or left legs in order to transverse the dermis. The blade is turned 360 degrees to complete the wound. A blunt tip cannula (e.g., 14-guage cannula) is inserted into the subcutaneous adipose tissue plane below the incision. The cannula is connected to a power assisted suction device. The cannula is moved throughout the adipose tissue plane to disrupt the connective tissue architecture. Approximately 500 cc of aspirate is obtained. After removal of the adipose tissue, homeostasis is achieved with standard surgical techniques and the wound is closed.

The lipoaspirate is processed in accordance with the methods disclosed hereinabove to obtain a unit of concentrated adipose derived stem cells. Approximately six hours after the prescribed adipose derived cell therapy, the patient is administered the stem cells. Based on the processing of the lipoaspirate, it is estimated that the patient receives an initial dose of stem cells in a range of between approximately $5.5 \times 10^4$ stem cells and $5.5 \times 10^5$ stem cells. The patient receives two supplemental dosages at 12 hour intervals after the initial administration. The stem cells are administered to the patient through a central venous catheter. To promote cellular engraftment in the target region, the flow of stem cells may be controlled by a balloon located downstream of the target site (via endovascular delivery)

and by a balloon upstream of the target site to create regions of low or minimal blood flow.

Improvements in the patient are noted within approximately six hours after the cell administration procedure. Several days after the cell administration procedure further improvement of the patient is noted evidenced by increased urine output, decreased creatinine, improved excretion of nitrogen, decreased need for CVVH (Continuous veno-veno hemodialysis) or HD (hemodialysis).

A number of publications and patents have been cited hereinabove. Each of the cited publications and patents are hereby incorporated by reference in their entireties.

Equivalents

Those skilled in the art will recognize, or be able to ascertain using no more than routine experimentation, many equivalents to the specific embodiments of the invention described herein. Such equivalents are intended to be encompassed by the following claims.

What is claimed is:

1. A method for treating a renal disorder associated with ischemia in a subject, comprising:
   identifying a subject with impaired renal function; and
   administering to the subject an amount of a concentrated population of adipose-derived regenerative cells comprising adipose-derived stem cells and endothelial progenitor cells sufficient to improve function of the kidney of said patient, wherein at least 0.1% of the concentrated population of adipose-derived cells are stem cells, and wherein said concentrated population of adipose-derived regenerative cells is obtained by acquiring an adipose tissue sample, separating away adipocytes and connective tissue, and washing and concentrating said adipose-derived regenerative cells.

2. The method of claim 1, wherein the renal disorder associated with ischemia is identified by assessing serum creatinine levels.

3. The method of claim 1, wherein the renal disorder associated with ischemia is identified by assessing blood urea nitrogen levels.

4. The method of claim 1, wherein the renal disorder associated with ischemia is identified by assessing serum chemistry profiles.

5. The method of claim 1, wherein the renal disorder associated with ischemia is identified by urinalysis.

6. The method of claim 1, wherein the renal disorder associated with ischemia is identified by assessing glomerular filtration rate.

7. The method of claim 1, wherein the subject is provided the concentrated population of adipose-derived regenerative cells within 12 hours after renal failure.

8. The method of claim 1, wherein the subject has post-surgical traumatic injury.

9. The method of claim 1, wherein the concentrated population of adipose-derived regenerative cells is not cultured before being provided to the patient.

10. The method of claim 1, wherein the concentrated population of adipose-derived regenerative cells is autologous.

11. The method of claim 1, wherein the renal disorder associated with ischemia comprises acute tubular necrosis.

12. The method of claim 1, wherein the renal disorder associated with ischemia comprises atherosclerotic renal artery stenosis.

13. The method of claim 1, wherein the administration comprises intravascular or intra-arterial administration.

14. The method of claim 1, wherein the administration comprises administration to the subject's renal vasculature.

15. The method of claim 1, wherein the concentrated population of adipose-derived regenerative cells is allogeneic.

16. The method of claim 1, wherein said concentrated population of adipose-derived regenerative cells further comprises an additive.

17. The method of claim 16, wherein said additive is selected from the group consisting of a disaggregation agent, an immunosuppressive agent, and an angiogenic factor.

18. The method of claim 16, wherein the additive reduces the likelihood of adverse reaction on infusion of the concentrated population of adipose-derived regenerative cells into the subject.

19. The method of claim 1, wherein said concentrated population of cells comprising adipose-derived stem cells is cryopreserved.

* * * * *